(12) United States Patent
Stemniski et al.

(10) Patent No.: US 8,808,303 B2
(45) Date of Patent: Aug. 19, 2014

(54) ORTHOPEDIC SURGICAL GUIDE

(75) Inventors: Paul Stemniski, Arlington, TN (US); Richard Obert, Germantown, TN (US); Sarah Lancianese, Orlando, FL (US)

(73) Assignee: Microport Orthopedics Holdings Inc., Tiel (NL)

( * ) Notice: Subject to any disclaimer, the term of this patent is extended or adjusted under 35 U.S.C. 154(b) by 274 days.

(21) Appl. No.: 13/330,091

(22) Filed: Dec. 19, 2011

(65) Prior Publication Data

US 2012/0130434 A1 May 24, 2012

Related U.S. Application Data

(63) Continuation-in-part of application No. 12/711,307, filed on Feb. 24, 2010.

(60) Provisional application No. 61/154,845, filed on Feb. 24, 2009, provisional application No. 61/425,054, filed on Dec. 20, 2010, provisional application No. 61/482,657, filed on May 5, 2011.

(51) Int. Cl.
| | | |
|---|---|---|
| A61B 17/58 | (2006.01) | |
| A61B 17/60 | (2006.01) | |
| A61F 2/00 | (2006.01) | |
| A61B 17/15 | (2006.01) | |
| A61B 17/17 | (2006.01) | |
| A61F 2/42 | (2006.01) | |
| A61B 19/00 | (2006.01) | |
| A61B 17/56 | (2006.01) | |

(52) U.S. Cl.
CPC ..... *A61B 17/1717* (2013.01); *A61B 2017/1775* (2013.01); *A61F 2/4202* (2013.01); *A61B 2019/508* (2013.01); *A61B 17/15* (2013.01); *A61B 2017/568* (2013.01)

USPC .......................................................... 606/96

(58) Field of Classification Search
USPC ................... 606/87, 90, 96–98, 105
See application file for complete search history.

(56) References Cited

U.S. PATENT DOCUMENTS

| | | |
|---|---|---|
| 3,314,420 A | 4/1967 | Smith et al. |
| 3,605,123 A | 9/1971 | Hahn |

(Continued)

FOREIGN PATENT DOCUMENTS

| | | |
|---|---|---|
| CN | 101111197 | 1/2008 |
| DE | 2306552 | 8/1974 |

(Continued)

OTHER PUBLICATIONS

International Search Report for International Application No. PCT/US2011/066025.

(Continued)

*Primary Examiner* — Andrew Yang
*Assistant Examiner* — Diana S Jones
(74) *Attorney, Agent, or Firm* — Duane Morris LLP

(57) ABSTRACT

A system for establishing an intramedullary path includes a body sized and configured to be received within a resected bone space. The body defines a first aperture that extends through the body and is sized and configured to receive a surgical tool therethrough. A first bone engaging structure extends from the body in a first direction and includes a first surface that is complementary to a surface topography of a first bone. When the first surface of the bone engaging structure engages the surface topography of the first bone to which the first surface is complementary, an axis defined by the first aperture is substantially collinear with a mechanical axis of the first bone.

18 Claims, 47 Drawing Sheets

(56) References Cited

U.S. PATENT DOCUMENTS

| | | |
|---|---|---|
| 3,798,679 A | 3/1974 | Ewald |
| 3,808,606 A | 5/1974 | Tronzo |
| 3,843,975 A | 10/1974 | Tronzo |
| 3,855,638 A | 12/1974 | Pilliar |
| 3,938,198 A | 2/1976 | Kahn et al. |
| 3,987,499 A | 10/1976 | Scharbach et al. |
| 4,052,753 A | 10/1977 | Dedo |
| 4,055,862 A | 11/1977 | Farling |
| 4,085,466 A | 4/1978 | Goodfellow et al. |
| 4,098,626 A | 7/1978 | Graham et al. |
| 4,203,444 A | 5/1980 | Bonnell et al. |
| 4,213,816 A | 7/1980 | Morris |
| 4,340,978 A | 7/1982 | Buechel et al. |
| 4,368,040 A | 1/1983 | Weissman |
| 4,436,684 A | 3/1984 | White |
| 4,501,266 A | 2/1985 | McDaniel |
| 4,502,161 A | 3/1985 | Wall |
| 4,586,496 A | 5/1986 | Keller |
| 4,594,380 A | 6/1986 | Chapin et al. |
| 4,601,290 A | 7/1986 | Effron et al. |
| 4,609,551 A | 9/1986 | Caplan et al. |
| 4,627,853 A | 12/1986 | Campbell et al. |
| 4,715,860 A | 12/1987 | Amstutz et al. |
| 4,721,104 A | 1/1988 | Kaufman et al. |
| 4,759,350 A | 7/1988 | Dunn et al. |
| 4,769,040 A | 9/1988 | Wevers |
| 4,841,975 A | 6/1989 | Woolson |
| 4,846,835 A | 7/1989 | Grande |
| 4,865,607 A | 9/1989 | Witzel et al. |
| 4,880,429 A | 11/1989 | Stone |
| 4,936,862 A | 6/1990 | Walker et al. |
| 4,979,949 A | 12/1990 | Matsen, III et al. |
| 5,002,547 A | 3/1991 | Poggie et al. |
| 5,041,138 A | 8/1991 | Vacanti et al. |
| 5,059,216 A | 10/1991 | Winters |
| 5,067,964 A | 11/1991 | Richmond et al. |
| 5,122,144 A | 6/1992 | Bert et al. |
| 5,129,908 A | 7/1992 | Petersen |
| 5,133,759 A | 7/1992 | Turner |
| 5,154,717 A | 10/1992 | Matsen, III et al. |
| 5,162,430 A | 11/1992 | Rhee et al. |
| 5,171,322 A | 12/1992 | Kenny |
| 5,197,985 A | 3/1993 | Caplan et al. |
| 5,206,023 A | 4/1993 | Hunziker |
| 5,226,914 A | 7/1993 | Caplan et al. |
| 5,234,433 A | 8/1993 | Bert et al. |
| 5,250,050 A | 10/1993 | Poggie et al. |
| 5,258,032 A | 11/1993 | Bertin |
| 5,270,300 A | 12/1993 | Hunziker |
| 5,288,797 A | 2/1994 | Khalil et al. |
| 5,303,148 A | 4/1994 | Mattson et al. |
| 5,306,311 A | 4/1994 | Stone et al. |
| 5,314,482 A | 5/1994 | Goodfellow et al. |
| 5,344,459 A | 9/1994 | Swartz |
| 5,360,446 A | 11/1994 | Kennedy |
| 5,368,858 A | 11/1994 | Hunziker |
| 5,380,332 A | 1/1995 | Ferrante |
| 5,387,216 A | 2/1995 | Thornhill et al. |
| 5,462,550 A * | 10/1995 | Dietz et al. .................. 606/86 R |
| 5,468,787 A | 11/1995 | Braden et al. |
| 5,474,559 A | 12/1995 | Bertin et al. |
| 5,478,739 A | 12/1995 | Slivka et al. |
| 5,486,180 A | 1/1996 | Dietz et al. |
| 5,501,687 A | 3/1996 | Willert et al. |
| 5,503,162 A | 4/1996 | Athanasiou et al. |
| 5,523,843 A | 6/1996 | Yamane et al. |
| 5,540,696 A | 7/1996 | Booth, Jr. et al. |
| 5,542,947 A | 8/1996 | Treacy |
| 5,554,190 A | 9/1996 | Draenert |
| 5,556,432 A | 9/1996 | Kubein-Meesenburg et al. |
| 5,571,205 A | 11/1996 | James |
| 5,575,793 A | 11/1996 | Carls et al. |
| 5,578,037 A | 11/1996 | Sanders et al. |
| 5,593,450 A | 1/1997 | Scott et al. |
| 5,597,379 A | 1/1997 | Haines et al. |
| 5,601,563 A | 2/1997 | Burke et al. |
| 5,613,970 A | 3/1997 | Houston et al. |
| 5,616,146 A | 4/1997 | Murray |
| 5,630,820 A | 5/1997 | Todd |
| 5,632,745 A | 5/1997 | Schwartz |
| 5,649,929 A | 7/1997 | Callaway |
| 5,658,291 A | 8/1997 | Techeira |
| 5,671,741 A | 9/1997 | Lang et al. |
| 5,682,886 A | 11/1997 | Delp et al. |
| 5,683,466 A | 11/1997 | Vitale |
| 5,684,562 A | 11/1997 | Fujieda |
| 5,688,282 A | 11/1997 | Baron et al. |
| 5,728,162 A | 3/1998 | Eckhoff |
| 5,735,277 A | 4/1998 | Schuster |
| 5,749,874 A | 5/1998 | Schwartz |
| 5,749,876 A | 5/1998 | Duvillier et al. |
| 5,768,134 A | 6/1998 | Swaelens et al. |
| 5,769,899 A | 6/1998 | Schwartz et al. |
| 5,786,217 A | 7/1998 | Tubo et al. |
| 5,800,438 A | 9/1998 | Tuke et al. |
| 5,827,289 A | 10/1998 | Reiley et al. |
| 5,830,216 A | 11/1998 | Insall et al. |
| 5,835,619 A | 11/1998 | Morimoto et al. |
| 5,842,477 A | 12/1998 | Naughton et al. |
| 5,847,804 A | 12/1998 | Sarver et al. |
| 5,853,746 A | 12/1998 | Hunziker |
| 5,860,981 A | 1/1999 | Bertin et al. |
| 5,871,018 A | 2/1999 | Delp et al. |
| 5,871,542 A | 2/1999 | Goodfellow et al. |
| 5,871,546 A | 2/1999 | Colleran et al. |
| 5,879,390 A | 3/1999 | Kubein-Meesenburg et al. |
| 5,880,976 A | 3/1999 | DiGioia, III et al. |
| 5,885,296 A | 3/1999 | Masini |
| 5,885,297 A | 3/1999 | Matsen, III |
| 5,885,298 A | 3/1999 | Herrington et al. |
| 5,897,559 A | 4/1999 | Masini |
| 5,899,859 A | 5/1999 | Votruba et al. |
| 5,900,245 A | 5/1999 | Sawhney et al. |
| 5,906,934 A | 5/1999 | Grande et al. |
| 5,911,723 A | 6/1999 | Ashby et al. |
| 5,916,220 A | 6/1999 | Masini |
| 5,939,323 A | 8/1999 | Valentini et al. |
| 5,961,523 A | 10/1999 | Masini |
| 5,968,051 A | 10/1999 | Luckman et al. |
| 5,972,385 A | 10/1999 | Liu et al. |
| 5,995,738 A | 11/1999 | DiGioia, III et al. |
| 6,001,895 A | 12/1999 | Harvey et al. |
| 6,002,859 A | 12/1999 | DiGioia, III et al. |
| 6,007,537 A | 12/1999 | Burkinshaw et al. |
| 6,010,509 A | 1/2000 | Delgado et al. |
| 6,013,103 A | 1/2000 | Kaufman et al. |
| 6,046,379 A | 4/2000 | Stone et al. |
| 6,056,754 A | 5/2000 | Haines et al. |
| 6,056,756 A | 5/2000 | Eng et al. |
| 6,057,927 A | 5/2000 | Lévesque et al. |
| 6,077,270 A | 6/2000 | Katz |
| 6,082,364 A | 7/2000 | Balian et al. |
| 6,090,144 A | 7/2000 | Letot et al. |
| 6,093,204 A | 7/2000 | Stone |
| 6,096,043 A | 8/2000 | Techiera et al. |
| 6,102,916 A | 8/2000 | Masini |
| 6,106,529 A | 8/2000 | Techiera |
| 6,110,209 A | 8/2000 | Stone |
| 6,120,541 A | 9/2000 | Johnson |
| 6,126,690 A | 10/2000 | Ateshian et al. |
| 6,139,578 A | 10/2000 | Lee et al. |
| 6,156,069 A | 12/2000 | Amstutz |
| 6,161,080 A | 12/2000 | Aouni-Ateshian et al. |
| 6,187,010 B1 | 2/2001 | Masini |
| 6,200,606 B1 | 3/2001 | Peterson et al. |
| 6,203,546 B1 | 3/2001 | MacMahon |
| 6,203,576 B1 | 3/2001 | Afriat et al. |
| 6,205,411 B1 | 3/2001 | DiGioia, III et al. |
| 6,206,927 B1 | 3/2001 | Fell et al. |
| 6,214,369 B1 | 4/2001 | Grande et al. |
| 6,217,894 B1 | 4/2001 | Sawhney et al. |
| 6,219,571 B1 | 4/2001 | Hargreaves et al. |
| 6,224,632 B1 | 5/2001 | Pappas et al. |
| 6,235,060 B1 | 5/2001 | Kubein-Meesenburg et al. |

(56) References Cited

U.S. PATENT DOCUMENTS

| | | |
|---|---|---|
| 6,251,143 B1 | 6/2001 | Schwartz et al. |
| 6,277,151 B1 | 8/2001 | Lee et al. |
| 6,281,195 B1 | 8/2001 | Rueger et al. |
| 6,283,980 B1 | 9/2001 | Vibe-Hansen et al. |
| 6,296,646 B1 | 10/2001 | Williamson |
| 6,299,905 B1 | 10/2001 | Peterson et al. |
| 6,322,588 B1 | 11/2001 | Ogle et al. |
| 6,328,765 B1 | 12/2001 | Hardwick et al. |
| 6,344,043 B1 | 2/2002 | Pappas |
| 6,344,059 B1 | 2/2002 | Krakovits et al. |
| 6,352,558 B1 | 3/2002 | Spector |
| 6,358,253 B1 | 3/2002 | Torrie et al. |
| 6,365,405 B1 | 4/2002 | Salzmann et al. |
| 6,371,958 B1 | 4/2002 | Overaker |
| 6,373,250 B1 | 4/2002 | Tsoref et al. |
| 6,375,658 B1 | 4/2002 | Hangody et al. |
| 6,379,367 B1 | 4/2002 | Vibe-Hansen et al. |
| 6,382,028 B1 | 5/2002 | Wooh et al. |
| 6,383,228 B1 | 5/2002 | Schmotzer |
| 6,387,131 B1 | 5/2002 | Miehlke et al. |
| 6,429,013 B1 | 8/2002 | Halvorsen et al. |
| 6,443,988 B2 | 9/2002 | Felt et al. |
| 6,443,991 B1 | 9/2002 | Running |
| 6,444,222 B1 | 9/2002 | Asculai et al. |
| 6,459,948 B1 | 10/2002 | Ateshian et al. |
| 6,468,314 B2 | 10/2002 | Schwartz et al. |
| 6,478,799 B1 | 11/2002 | Williamson |
| 6,479,996 B1 | 11/2002 | Hoogeveen et al. |
| 6,510,334 B1 | 1/2003 | Schuster et al. |
| 6,520,964 B2 | 2/2003 | Tallarida et al. |
| 6,558,421 B1 | 5/2003 | Fell et al. |
| 6,560,476 B1 | 5/2003 | Pelletier et al. |
| 6,575,980 B1 | 6/2003 | Robie et al. |
| 6,620,168 B1 | 9/2003 | Lombardo et al. |
| 6,626,945 B2 | 9/2003 | Simon et al. |
| 6,626,948 B2 | 9/2003 | Storer et al. |
| 6,632,225 B2 | 10/2003 | Sanford et al. |
| 6,632,235 B2 | 10/2003 | Weikel et al. |
| 6,652,587 B2 | 11/2003 | Felt et al. |
| 6,673,077 B1 | 1/2004 | Katz |
| 6,679,917 B2 | 1/2004 | Ek |
| 6,712,856 B1 | 3/2004 | Carignan et al. |
| 6,905,514 B2 | 6/2005 | Carignan et al. |
| 6,916,341 B2 | 7/2005 | Rolston |
| 6,928,742 B2 | 8/2005 | Broers et al. |
| 6,969,393 B2 | 11/2005 | Pinczewski et al. |
| 7,008,430 B2 | 3/2006 | Dong et al. |
| 7,060,074 B2 | 6/2006 | Rosa et al. |
| 7,104,997 B2 | 9/2006 | Lionberger et al. |
| 7,115,131 B2 | 10/2006 | Engh et al. |
| 7,117,027 B2 | 10/2006 | Zheng et al. |
| 7,141,053 B2 | 11/2006 | Rosa et al. |
| 7,184,814 B2 | 2/2007 | Lang et al. |
| 7,239,908 B1 | 7/2007 | Alexander et al. |
| 7,245,697 B2 | 7/2007 | Lang |
| 7,282,054 B2 | 10/2007 | Steffensmeier et al. |
| 7,292,674 B2 | 11/2007 | Lang |
| 7,379,529 B2 | 5/2008 | Lang |
| 7,467,892 B2 | 12/2008 | Lang et al. |
| 7,468,075 B2 | 12/2008 | Lang et al. |
| 7,534,246 B2 | 5/2009 | Reiley et al. |
| 7,534,263 B2 | 5/2009 | Burdulis, Jr. et al. |
| 7,618,451 B2 | 11/2009 | Berez et al. |
| 7,747,305 B2 | 6/2010 | Dean et al. |
| 7,806,896 B1 | 10/2010 | Bonutti |
| 7,881,768 B2 | 2/2011 | Lang et al. |
| 7,981,158 B2 | 7/2011 | Fitz et al. |
| 7,983,777 B2 | 7/2011 | Melton et al. |
| 8,036,729 B2 | 10/2011 | Lang et al. |
| 8,062,302 B2 | 11/2011 | Lang et al. |
| 8,066,708 B2 | 11/2011 | Lang et al. |
| 8,083,745 B2 | 12/2011 | Lang et al. |
| 8,105,330 B2 | 1/2012 | Fitz et al. |
| 8,112,142 B2 | 2/2012 | Alexander et al. |
| 8,122,582 B2 | 2/2012 | Burdulis, Jr. et al. |
| RE43,282 E | 3/2012 | Alexander et al. |
| 2001/0001120 A1 | 5/2001 | Masini |
| 2001/0010023 A1 | 7/2001 | Schwartz et al. |
| 2001/0039455 A1 | 11/2001 | Simon et al. |
| 2002/0013626 A1 | 1/2002 | Geistlich et al. |
| 2002/0029038 A1 | 3/2002 | Haines |
| 2002/0045940 A1 | 4/2002 | Giannetti et al. |
| 2002/0059049 A1 | 5/2002 | Bradbury et al. |
| 2002/0068979 A1 | 6/2002 | Brown et al. |
| 2002/0072821 A1 | 6/2002 | Baker |
| 2002/0079601 A1 | 6/2002 | Russell et al. |
| 2002/0082703 A1 | 6/2002 | Repicci |
| 2002/0087274 A1 | 7/2002 | Alexander et al. |
| 2002/0106625 A1 | 8/2002 | Hung et al. |
| 2002/0115647 A1 | 8/2002 | Halvorsen et al. |
| 2002/0120274 A1 | 8/2002 | Overaker et al. |
| 2002/0120281 A1 | 8/2002 | Overaker |
| 2002/0127264 A1 | 9/2002 | Felt et al. |
| 2002/0133230 A1 | 9/2002 | Repicci |
| 2002/0143402 A1 | 10/2002 | Steinberg |
| 2002/0151986 A1 | 10/2002 | Asculai et al. |
| 2002/0156150 A1 | 10/2002 | Williams et al. |
| 2002/0173852 A1 | 11/2002 | Felt et al. |
| 2002/0183850 A1 | 12/2002 | Felt et al. |
| 2003/0028196 A1 | 2/2003 | Bonutti |
| 2003/0055500 A1 | 3/2003 | Fell et al. |
| 2003/0055501 A1 | 3/2003 | Fell et al. |
| 2003/0055502 A1 | 3/2003 | Lang et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0100907 A1 | 5/2003 | Rosa et al. |
| 2003/0100953 A1 | 5/2003 | Rosa et al. |
| 2003/0120347 A1 | 6/2003 | Steinberg |
| 2003/0158558 A1 | 8/2003 | Horn |
| 2003/0158606 A1 | 8/2003 | Coon et al. |
| 2003/0163137 A1 | 8/2003 | Smucker et al. |
| 2003/0173695 A1 | 9/2003 | Monkhouse et al. |
| 2003/0216669 A1 | 11/2003 | Lang et al. |
| 2003/0225457 A1 | 12/2003 | Justin et al. |
| 2003/0236521 A1 | 12/2003 | Brown et al. |
| 2004/0098133 A1 | 5/2004 | Carignan et al. |
| 2004/0102852 A1 | 5/2004 | Johnson et al. |
| 2004/0122521 A1 | 6/2004 | Lee et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0153162 A1 | 8/2004 | Sanford et al. |
| 2004/0153164 A1 | 8/2004 | Sanford et al. |
| 2004/0167390 A1 | 8/2004 | Alexander et al. |
| 2004/0167630 A1 | 8/2004 | Rolston |
| 2004/0193280 A1 | 9/2004 | Webster et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2004/0249386 A1 | 12/2004 | Faoro |
| 2005/0015153 A1 | 1/2005 | Goble et al. |
| 2005/0021039 A1 | 1/2005 | Cusick et al. |
| 2005/0043807 A1 | 2/2005 | Wood |
| 2005/0055028 A1 | 3/2005 | Haines |
| 2005/0085920 A1 | 4/2005 | Williamson |
| 2005/0107883 A1 | 5/2005 | Goodfried et al. |
| 2005/0107884 A1 | 5/2005 | Johnson et al. |
| 2005/0119664 A1 | 6/2005 | Carignan et al. |
| 2005/0143745 A1 | 6/2005 | Hodorek et al. |
| 2005/0148843 A1 | 7/2005 | Roose |
| 2005/0171545 A1 | 8/2005 | Walsh et al. |
| 2005/0171612 A1 | 8/2005 | Rolston |
| 2005/0192588 A1 | 9/2005 | Garcia |
| 2005/0216305 A1 | 9/2005 | Funderud |
| 2005/0234461 A1 | 10/2005 | Burdulis, Jr. et al. |
| 2005/0267584 A1 | 12/2005 | Burdulis et al. |
| 2006/0052795 A1 | 3/2006 | White |
| 2006/0111722 A1 | 5/2006 | Bouadi |
| 2006/0149283 A1 | 7/2006 | May et al. |
| 2006/0200162 A1 | 9/2006 | Farling et al. |
| 2006/0235421 A1 | 10/2006 | Rosa et al. |

(56) References Cited

U.S. PATENT DOCUMENTS

| | | |
|---|---|---|
| 2007/0015995 A1 | 1/2007 | Lang |
| 2007/0073305 A1 | 3/2007 | Lionberger et al. |
| 2007/0118141 A1 | 5/2007 | Marchyn et al. |
| 2007/0198022 A1 | 8/2007 | Lang et al. |
| 2007/0203430 A1 | 8/2007 | Lang et al. |
| 2007/0233151 A1 | 10/2007 | Chudik |
| 2007/0233156 A1 | 10/2007 | Metzger |
| 2007/0276224 A1 | 11/2007 | Lang et al. |
| 2007/0293868 A1 | 12/2007 | Delfosse et al. |
| 2008/0004709 A1 | 1/2008 | O'Neill et al. |
| 2008/0015433 A1 | 1/2008 | Alexander et al. |
| 2008/0025463 A1 | 1/2008 | Lang |
| 2008/0031412 A1 | 2/2008 | Lang et al. |
| 2008/0058613 A1 | 3/2008 | Lang et al. |
| 2008/0058945 A1 | 3/2008 | Hajaj et al. |
| 2008/0114370 A1 | 5/2008 | Schoenefeld |
| 2008/0170659 A1 | 7/2008 | Lang et al. |
| 2008/0195216 A1 | 8/2008 | Philipp |
| 2008/0219412 A1 | 9/2008 | Lang |
| 2008/0243127 A1 | 10/2008 | Lang et al. |
| 2008/0255565 A1 | 10/2008 | Fletcher |
| 2008/0275452 A1 | 11/2008 | Lang et al. |
| 2008/0281328 A1 | 11/2008 | Lang et al. |
| 2008/0281329 A1 | 11/2008 | Lang et al. |
| 2008/0281426 A1 | 11/2008 | Fitz et al. |
| 2009/0024131 A1 | 1/2009 | Metzger et al. |
| 2009/0076371 A1 | 3/2009 | Lang et al. |
| 2009/0087276 A1 | 4/2009 | Rose |
| 2009/0088753 A1 | 4/2009 | Aram et al. |
| 2009/0088758 A1 | 4/2009 | Bennett |
| 2009/0099567 A1 | 4/2009 | Zajac |
| 2009/0131941 A1 | 5/2009 | Park et al. |
| 2009/0131942 A1 | 5/2009 | Aker et al. |
| 2009/0222014 A1 | 9/2009 | Bojarski et al. |
| 2009/0307893 A1 | 12/2009 | Burdulis, Jr. et al. |
| 2010/0121325 A1 | 5/2010 | Tyber et al. |
| 2010/0160917 A1 | 6/2010 | Fitz et al. |
| 2010/0281678 A1 | 11/2010 | Burdulis, Jr. et al. |
| 2010/0298894 A1 | 11/2010 | Bojarski et al. |
| 2010/0305573 A1 | 12/2010 | Fitz et al. |
| 2010/0305574 A1 | 12/2010 | Fitz et al. |
| 2011/0066193 A1 | 3/2011 | Lang et al. |
| 2011/0071581 A1 | 3/2011 | Lang et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0029520 A1 | 2/2012 | Lang et al. |
| 2012/0041446 A1 | 2/2012 | Wong et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0101503 A1 | 4/2012 | Lang et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |

FOREIGN PATENT DOCUMENTS

| | | |
|---|---|---|
| DE | 3516743 | 11/1986 |
| DE | 44 34 539 | 4/1996 |
| DE | 20303498 | 8/2003 |
| DE | 202008017199 | 3/2009 |
| DE | 202008017200 | 3/2009 |
| EP | 0337901 | 10/1989 |
| EP | 0528080 | 2/1993 |
| EP | 0530804 | 10/1993 |
| EP | 0626156 | 11/1994 |
| EP | 0 704 193 | 4/1996 |
| EP | 0896825 | 2/1999 |
| EP | 0938869 | 9/1999 |
| EP | 0613380 | 12/1999 |
| EP | 0993807 | 4/2000 |
| EP | 1074229 | 2/2001 |
| EP | 1077253 | 2/2001 |
| EP | 1120087 | 8/2001 |
| EP | 1129675 | 9/2001 |
| EP | 1132021 | 9/2001 |
| EP | 0732091 | 12/2001 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| FR | 2819714 | 7/2002 |
| GB | 1451283 | 9/1976 |
| GB | 2291355 | 1/1996 |
| GB | 2348373 | 10/2000 |
| JP | 8-173465 | 7/1996 |
| JP | 9-206322 | 8/1997 |
| JP | 2002-102236 | 4/2002 |
| WF | 98/12994 | 4/1998 |
| WO | 87/02882 | 5/1987 |
| WO | 90/09769 | 9/1990 |
| WO | 93/04710 | 3/1993 |
| WO | 93/09819 | 5/1993 |
| WO | 93/25157 | 12/1993 |
| WO | 95/27450 | 10/1995 |
| WO | 95/28688 | 10/1995 |
| WO | 95/30390 | 11/1995 |
| WO | 95/32623 | 12/1995 |
| WO | 96/24302 | 8/1996 |
| WO | 97/25942 | 7/1997 |
| WO | 97/26847 | 7/1997 |
| WO | 97/27885 | 8/1997 |
| WO | 97/38676 | 10/1997 |
| WO | 98/20816 | 5/1998 |
| WO | 98/30617 | 7/1998 |
| WO | 98/32384 | 7/1998 |
| WO | 99/02654 | 1/1999 |
| WO | 99/08598 | 2/1999 |
| WO | 99/08728 | 2/1999 |
| WO | 99/42061 | 8/1999 |
| WO | 99/47186 | 9/1999 |
| WO | 99/51719 | 10/1999 |
| WO | 99/56674 | 11/1999 |
| WO | 00/09179 | 2/2000 |
| WO | 00/15153 | 3/2000 |
| WO | 00/35346 | 6/2000 |
| WO | 00/48550 | 8/2000 |
| WO | 00/59411 | 10/2000 |
| WO | 00/74554 | 12/2000 |
| WO | 01/10356 | 2/2001 |
| WO | 01/17463 | 3/2001 |
| WO | 01/19254 | 3/2001 |
| WO | 01/35968 | 5/2001 |
| WO | 01/45764 | 6/2001 |
| WO | 01/68800 | 9/2001 |
| WO | 01/70142 | 9/2001 |
| WO | 01/91672 | 12/2001 |
| WO | 02/00270 | 1/2002 |
| WO | 02/00275 | 1/2002 |
| WO | 02/02158 | 1/2002 |
| WO | 02/22013 | 3/2002 |
| WO | 02/22014 | 3/2002 |
| WO | 02/23483 | 3/2002 |

(56) References Cited

FOREIGN PATENT DOCUMENTS

| WO | 02/34310 | 5/2002 |
|---|---|---|
| WO | 02/36147 | 5/2002 |
| WO | 02/096268 | 12/2002 |
| WO | 03/007788 | 1/2003 |
| WO | WO 03/017822 | 3/2003 |
| WO | 03/037192 | 5/2003 |
| WO | 03/047470 | 6/2003 |
| WO | 03/051210 | 6/2003 |
| WO | 03/055400 | 7/2003 |
| WO | 2004/043305 | 5/2004 |
| WO | 2004/049981 | 6/2004 |
| WO | 2005/051239 | 6/2005 |
| WO | 2005/051240 | 6/2005 |
| WO | 2006/060795 | 6/2006 |
| WO | 2006/127283 | 11/2006 |
| WO | 2007/041375 | 4/2007 |
| WO | WO 2007/061983 | 5/2007 |
| WO | 2007/092841 | 8/2007 |
| WO | 2008/112996 | 9/2008 |
| WO | 2008/157412 | 12/2008 |
| WO | 2009/111639 | 9/2009 |
| WO | 2010/121147 | 10/2010 |
| WO | WO 2011/110374 | 9/2011 |

OTHER PUBLICATIONS

Andersson, et al., "MacIntosh Arthroplasty in Rheumatoid Arthritis," Acta. Orthrop. Scand., 1974, pp. 245-259, 45(2).
Argenson, et al., "Is There a Place for Patellofemoral Arthroplasty?," Clinical Orthopaedics and Related Research No. 321, 1995, pp. 162-167.
DeWinter, et al., "The Richards Type II Patellofemoral Arthroplasty," Acta Orthop Scand, 2001, pp. 487-490, 72(5).
Delp, et al., "A Graphics-Based Software System to Develop and Analyze Models of Musculoskeletal Structures," Comput. Biol. Med., 1995, pp. 21-34, vol. 25, No. 1.
Farrar, et al., "Computed Tomography Scan Scout Film for Measurement of Femoral Axis in Knee Arthroplasty," J. Arthroplasty, 1999, pp. 1030-1031, vol. 14, No. 8.
Kim, et al., "Measurement of Femoral Neck Anteversion in 3D. Part 1: 3D Imaging Method," Med. and Viol. Eng. and Computing, 2000, pp. 603-609, vol. 38, No. 6.
Lam, et al., "X-Ray Diagnosis: A Physician's Approach," 1998, Title page and Table of Contents pages Only, ISBN 9813083247, Springer-Verlag publishers.
Lam, et al., "Varus/Valgus Alignment of the Femoral Component in Total Knee Arthroplasty," The Knee, 2003, pp. 237-241, vol. 10.
Lu, et al., "In Vitro Degradation of Porous poly(L-lactic acid) Foams," Biomaterials, Aug. 2000, pp. 1595-1605, 21(15).
Mahaisavariya, et al., "Morphological Study of the Proximal Femur: A New Method of Geometrical Assessment Using 3 Dimensional Reverse Engineering," Med. Eng. and Phys., 2002, pp. 617-622, vol. 24.
Marler, et al., "Soft-Tissue Augmentation with Injectable Alginate and Synegeneic Fibroblasts," Plastic & Reconstructive Surgery, May 2000 pp. 2049-2058, 105(6).
Slone, et al., "Body CT: A Practical Approach," 1999, Title page and Table of Contents pages Only, ISBN 007058219, McGraw-Hill.
Stauffer, et al., "The MacIntosh Prosthesis. Prospective Clinical and Gait Evaluation," Arch. Surg., 1975, pp. 717-720, 110(6).
Stout, et al., "X-RAY Structure Determination: A Practical Guide," 1989, Title page and Table of Contents pages Only, ISBN 0471607118, John Wiley & Sons.
Wiese, et al., "Biomaterial Properties and Biocompatibility in Cell Culture of a Novel Self-Inflating Hydrogel Tissue Expander," J. Biomedical Materials Research Part A, Nov. 2000, pp. 179-188, 54(2).
Tamez-Pena, et al., "MRI Isotropic Resolution Reconstruction from Two Orthogonal Scans," Proceedings of the SPIE—The International Society for Optical Engineering SOIE-OMT, 2001, pp. 87-97, vol. 4322.
Testi, et al., "Border Tracing Algorithm Implementation for the Femoral Geometry Reconstruction," Comp. Meth. and Programs in Biomed., 2001, pp. 175-182, vol. 65.
Vandeberg, et al., "Assessment of Knee Cartilage in Cadavers with Dual-Detector Spiral CT Arthrography and MR Imaging," Radiology, Feb. 2002, pp. 430-435, 222(2).
Yusof, et al., "Preparation and Characterization of Chitin Beads as a Wound Dressing Precursor," J. Biomedical Materials Research Part A, Oct. 2000, pp. 59-68, 54(1).
International Searching Authority, International Search Report—International Application No. PCT/US2009/036189, dated Jul. 13, 2009, together with the Written Opinion of the International Searching Authority, 11 pages.
Sunstein Kann Murphy & Timbers LLP, Supplemental Amendment dated Sep. 18, 2009, pertaining to U.S. Appl. No. 09/882,363, 11 pages.
United States Patent and Trademark Office, Office Action dated May 5, 2008, pertaining to U.S. Appl. No. 10/724,010, 13 pages.
Bromberg & Sunstein LLP, Request for Continued Examination and Response dated Nov. 4, 2008, pertaining to U.S. Appl. No. 10/724,010, 15 pages.
United States Patent and Trademark Office, Office Action dated Jan. 29, 2009, pertaining to U.S. Appl. No. 10/724,010, 9 pages.
Bromberg & Sunstein LLP, Response to Office Action dated Jan. 29, 2009, pertaining to U.S. Appl. No. 10/724,010, 16 pages.
United States Patent and Trademark Office, Office Action dated Nov. 26, 2007, pertaining to U.S. Appl. No. 11/002,753, 15 pages.
Bromberg & Sunstein LLP, Request for Continued Examination and Response dated Feb. 27, 2008, pertaining to U.S. Appl. No. 11/002,573, 19 pages.
United States Patent and Trademark Office, Office Action dated May 9, 2008, pertaining to U.S. Appl. No. 11/002,573, 17 pages.
Bromberg & Sunstein LLP, Amendment dated Aug. 12, 2008, pertaining to U.S. Appl. No. 11/002,573, 25 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
United States Patent and Trademark Office, Office Action dated Jan. 26, 2010, pertaining to U.S. Appl. No. 11/671,745, 9 pages.
United States Patent and Trademark Office, Office Action dated Oct. 20, 2010, pertaining to U.S. Appl. No. 12/135,719, 10 pages.
Sunstein Kann Murphy & Timbers LLP, Response to Office Action dated Aug. 26, 2010, pertaining to U.S. Appl. No. 12/361,213, 22 pages.
United States Patent and Trademark Office, Office Action dated Feb. 28, 2011, pertaining to U.S. Appl. No. 12/048,764, 12 pages.
European Patent Office, Extended European Search Report—European Application No. 10181743.5-2310, dated Mar. 11, 2011, 6 pages.
United States Patent and Trademark Office, Office Action dated Apr. 20, 2011, pertaining to U.S. Appl. No. 12/135,612, 13 pages.
United States Patent and Trademark Office, Office Action dated Sep. 26, 2011, pertaining to U.S. Appl. No. 12/048,764, 9 pages.
Birnbaum, et al., "Computer-Assisted Orthopedic Surgery with Individual Templates and Comparison to Conventional Operation Method," Spine, Feb. 2001, pp. 365-369, vol. 26, No. 4.
Chelule, et al., "Computer Aided Design of Personalized Jigs in Total Knee Replacement," 3rd Annual Meeting of CAOS Int'l Proc., Jun. 18-21, 2003, pp. 58-59, Spain.
Froemel, et al., "Computer Assisted Template Based Navigation for Total Knee Replacement," Documents presented at CAOS on Jun. 17, 2001, 4 pages.

(56) References Cited

OTHER PUBLICATIONS

Hafez, et al., "Computer Assisted Total Knee Replacement: Could a Two-Piece Custom Template Replace the Complex Conventional Instrumentations?", 4th Annual Meeting of CAOS Int'l Proc., Jun. 16-19, 2004, pp. 63-64, Chicago.
Hafez, et al., "Computer-Assisted Total Hip Arthroplasty: The Present and the Future," Future Rheumatol., 2006, pp. 121-131, vol. 1.
Portheine, et al., "Potentials of CT-based Planning and Template-based Procedure in Hip and Knee Surgery," Orth. Prac., 2000, pp. 786-791, vol. 36, in German.
Portheine, et al., "Potentials of CT-based Planning and Template-based Procedure in Hip and Knee Surgery," Orth. Prac., 2000, pp. 786-791, vol. 36, English Translation with Certification.
Portheine, "Model-Based Operation Planning in Orthopedic Surgery," Thesis, Apr. 22, 2004, 90 pages, RWTH Aachen University, in German.
Portheine, "Model-Based Operation Planning in Orthopedic Surgery," Thesis, Apr. 22, 2004, 170 pages, RWTH Aachen University, English Translation with Certification.
Radermacher, et al., "Computer Integrated Surgery—Connecting Planning and Execution of Surgical Intervention in Orthopedics," Surgical Therapy Technology, Helmholtz-Institut Aachen Research Report, 1991-1992, pp. 187, 196-202.
Radermacher, et al., "Computer Assisted Matching of Planning and Execution in Orthopedic Surgery," IEEE, EMBS, 1993, pp. 946-947, San Diego.
Radermacher, "Computer Assisted Matching of Planning and Execution in Orthopedic Surgery," Slide Presentation, Nov. 29, 1993, 22 pages.
Radermacher, et al., "Computer Integrated Advanced Orthopedics (CIAO)," 2nd European Conference on Eng. and Med., Apr. 26, 1993, 12 pages.
Radermacher, et al., "Surgical Therapy Technology," Helmholtz-Institut Aaachen Research Report, 1993-1994, pp. 189-219.
Radermacher, "Image Guided Orthopedic Surgery with Individual Templates," Helmholtz-Institute for Biomed. Eng., 1997, 2 pages.
Radermacher, et al., "Computer-Assisted Operative Interventions in Orthopedics—Are There Prospects for Endoprosthetics As Well?", Prac. Ortho., 1997, pp. 149-164, vol. 27, in German.
Radermacher, et al., "Computer-Assisted Operative Interventions in Orthopedics—Are There Prospects for Endoprosthetics As Well?", Prac. Ortho., 1997, pp. 1-17, vol. 27, English Translation with Certification.
Radermacher, "Computer-Based Decision Support in the Selection and Evaluation of Contact Surfaces for Manual Referencing," Lecture presented at Helmholtz Meeting '98 and OSS '98, 7 pages, in German.
Radermacher, "Computer-Based Decision Support in the Selection and Evaluation of Contact Surfaces for Manual Referencing," Lecture presented at Helmholtz Meeting '98 and OSS '98, 8 pages, English Translation with Certification.
International Search Report for PCT/US2012/036830, Jun. 13, 2012.
Radermacher, et al., "Computer-Assisted Planning and Operation in Orthopedics," Orth. Prac. 36th Year, Dec. 2000, pp. 731-737, in German.
Radermacher, et al., "Computer-Assisted Planning and Operation in Orthopedics," Orth. Prac. 36th Year, Dec. 2000, pp. 731-737, English Translation with Certification.
Radermacher, "Template Based Navigation—An Efficient Technique for Hip and Knee Surgery," CAOS First Asian Meet, Mar. 27-28, 2004, pp. 45-50, India.
Rau, et al., "Small and Neat," Medical Tech. Int'l, 1993-94, pp. 65, 67 and 69.
Schkommadau, et al., "Clinical Application of Individual Templates for Pedicle Screw Placement in Comparison to Computer Navigation," Poster presented at CAOS, Feb. 18, 2000, 1 page.
Schkommadau, et al., "Clinical Experience With the Individual Template Technique," Orth. Prac., 2001, pp. 19-22, vol. 37, No. 1, in German.
Schkommadau, et al., "Clinical Experience With the Individual Template Technique," Orth. Prac., 2001, pp. 19-22, vol. 37, No. 1, English Translation with Certification.
Seel, et al., "Three-Dimensional Planning and Virtual Radiographs in Revision Total Hip Arthroplasty for Instability," Clinical Orthopaedics and Related Research, Jan. 2006, pp. 35-38, No. 442.
Staudte, et al., "Computer-Assisted Operation Planning and Technique in Orthopedics," North Rhine-Westphalia Acad. for Sciences, Lecture N.444, 2000, 17 pages, ISSN 0944-8799, in German.
Staudte, et al., "Computer-Assisted Operation Planning and Technique in Orthopedics," North Rhine-Westphalia Acad. for Sciences, Lecture N.444, 2000, 34 pages, ISSN 0944-8799, English Translation with Certification.
European Patent Office, European Search Report—Application No. 09716738.1 dated Feb. 6, 2012, 10 pages.
European Patent Office, Extended European Search Report—Application No. 10181149.5-1526 dated Apr. 19, 2012, 9 pages.
European Patent Office, Extended European Search Report—Application No. 10181198.2-1526 dated Apr. 19, 2012, 9 pages.
United States Patent and Trademark Office, Office Action dated Jan. 13, 2012, pertaining to U.S. Appl. No. 12/776,840, 10 pages.
United States Patent and Trademark Office, Office Action dated Jan. 26, 2012, pertaining to U.S. Appl. No. 12/139,324, 14 pages.
United States Patent and Trademark Office, Office Action dated May 31, 2012, pertaining to U.S. Appl. No. 12/398,753, 7 pages.
United States Patent and Trademark Office, Office Action dated Jun. 5, 2012, pertaining to U.S. Appl. No. 12/776,984, 7 pages.

\* cited by examiner

ORTHOPEDIC SURGICAL GUIDE

CROSS REFERENCE TO RELATED APPLICATIONS

This application is a continuation-in-part of U.S. patent application Ser. No. 12/711,307, which was filed on Feb. 24, 2010 claiming priority to U.S. Provisional Patent Application No. 61/154,845 filed on Feb. 24, 2009, and claims priority to U.S. Provisional Patent Application No. 61/425,054 filed on Dec. 20, 2010 and to U.S. Provisional Patent Application No. 61/482,657 filed on May 5, 2011, the entireties of which are herein incorporated by reference.

FIELD OF DISCLOSURE

The disclosed system and method generally relate to surgical guides. More specifically, the disclosed system and method relate to surgical guides for orthopedic procedures involving an ankle.

BACKGROUND

Total joint replacement prostheses typically include a specially designed jig or fixture to enable a surgeon to make accurate and precise bone resections in and around the joint being prepared to accept the prosthesis. The ultimate goal with any total joint prosthesis is to approximate the function and structure of the natural, healthy structures that the prosthesis is replacing. Should the prosthesis not be properly attached to the joint, i.e., an ankle or knee, the misalignment could result in discomfort to the patient, gait problems, or degradation of the prosthesis.

Many surgical procedures employ the use of intra-operative fluoroscopy to check the alignment of the intramedullary cavities that are prepared to receive the joint replacement prosthesis. However, the use of intra-operative fluoroscopy in the operating room has several drawbacks. One such drawback is that the use of fluoroscopy to check the alignment of intramedullary cavities formed during surgery increases the overall length of the surgical procedure as time is taken to acquire and evaluate the fluoroscopic images. Long surgery times lead to increased tourniquet time forth patient and therefore may increase recovery time.

Another drawback of fluoroscopy is exposing the patient and others in the operating room to the ionized radiation. For example, the U.S. Food and Drug Administration ("FDA") has issued several articles and public health advisories concerning the use of the fluoroscopy during surgical procedures. Consequently, even though steps are taken to protect the patient and other from the ionized radiation, it is virtually impossible to eliminate all risk associated with the ionized radiation.

SUMMARY

A system for establishing an intramedullary path is disclosed that includes a body sized and configured to be received within a resected bone space. The body defines a first aperture that extends through the body and is sized and configured to receive a surgical tool therethrough. A first bone engaging structure extends from the body in a first direction and includes a first surface that is complementary to a surface topography of a first bone. When the first surface of the bone engaging structure engages the surface topography of the first bone to which the first surface is complementary, an axis defined by the first aperture is substantially collinear with a mechanical axis of the first bone.

Also disclosed is a system for establishing an intramedullary path that includes a drill guide mount having a body sized and configured to be received within a resected bone space. The body defines a first aperture that extends through the body. A first bone engaging structure extends from the body in a first direction and includes a first surface that is complementary to a surface topography of a first bone. A drill guide is sized and configured to be received within the first aperture defined by the body of the drill guide mount. The drill guide defines a second aperture sized and configured to receive the surgical tool therethrough. When the first surface of the bone engaging structure engages the surface topography of the bone to which the first surface is complementary, an axis defined by the second aperture is substantially collinear with a mechanical axis of the first bone.

A method is also disclosed that includes inserting a drill guide into an aperture defined by a drill guide mount. The drill guide mount includes a first bone engaging structure extending from a body of the drill guide mount in a first direction and having a first surface that is complementary to a surface topography of a first bone. The drill guide mount and the drill guide disposed within the first aperture of the drill guide mount are inserted into a resected bone space such that the first surface of the bone engaging structure correspondingly engages the first bone. A surgical tool is extended through a second aperture defined by the drill guide to establish an intramedullary channel within the first bone that is substantially collinear with a mechanical axis of the first bone.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein.

DETAILED DESCRIPTION

Figure 1:
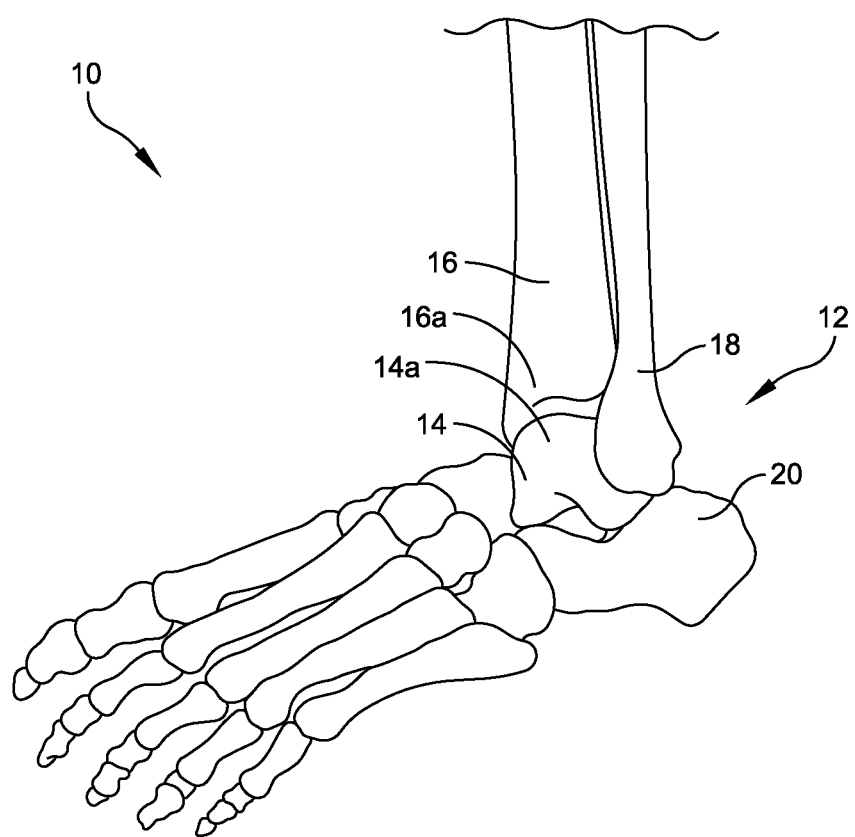
FIG. 1 illustrates the bones of a human foot and ankle.

This description of preferred embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The disclosed systems and methods advantageously utilize custom manufactured surgical instruments, guides, and/or fixtures that are based upon a patient's anatomy to reduce the use of fluoroscopy during a surgical procedure. In some instances, the use of fluoroscopy during a surgical procedure may be eliminated altogether. The custom instruments, guides, and/or fixtures are created by imaging a patient's anatomy with a computer tomography scanner ("CT"), a magnetic resonance imaging machine ("MRI"), or like medical imaging technology prior to surgery and utilizing these images to create patient-specific instruments, guides, and/or fixtures.

Although the following description of the custom patient-specific instruments are described with respect to a foot 10 and ankle 12 (FIG. 1), one skilled in the art will understand that the systems and methods may be utilized in connection with other joints including, but not limited to, knees, hips, shoulders, and the like. As shown in FIG. 1, a typical human foot 10 includes an ankle joint 12 formed between a talus 14, which is disposed on a calcaneus 20, and a tibia 16 and fibula 18.

A CT or MRI scanned image or series of images may be taken of a patient's ankle 12 (or other joint) and then converted from, e.g., a DICOM image format, to a solid computer model of the ankle including the calcaneus, talus, tibia, navicular, and fibula to determine implant alignment, type, and sizing using specialized modeling methods that are often embodied in computer software. Computer generated solid models that are derived from the data of the CT or MRI scan image will often include precise and accurate information regarding the surface contours surrounding the structures that have been imaged, e.g., the surface topography of the bones or contour of fascia that have been imaged. It will be understood that by surface topography it is meant the location, shape, size and distribution of surface features such as concavities and prominences or the like.

The methods disclosed in U.S. Pat. No. 5,768,134, issued to Swaelens et al., which is incorporated by reference herein in its entirety, have been found to yield adequate conversions of data of CT or MRI scan images to solid computer models. In some embodiments, images are made of a foot 10, i.e., the calcaneus 20, talus 14, tibia 16, and fibula 18 of a patient using a CT or MRI machine, or other digital image capturing and processing unit as is understood by one skilled in the art. The image data is processed in a processing unit, after which a model 50 is generated using the processed digitized image data as illustrated in FIGS. 2A and 2B.

Figure 2B:
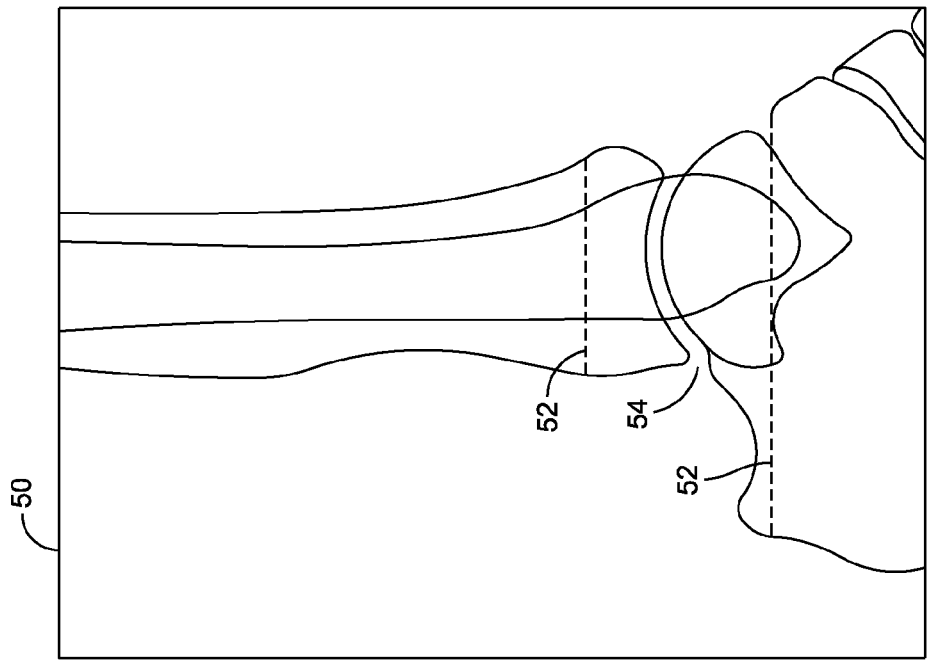
FIGS. 2A and 2B are schematic representations of a scanned image of a human foot and ankle joint.
Figure 2A:
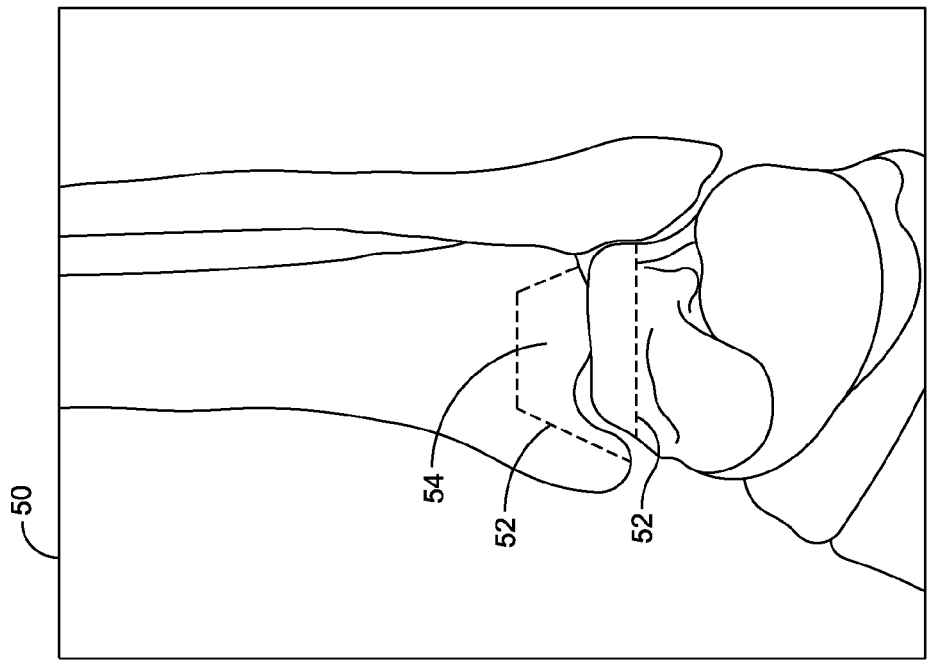

Interactive processing and preparation of the digitized image data is performed, which includes the manipulation and introduction of additional extrinsic digital information, such as, predefined reference locations 52 for component positioning and alignment so that adjustments to the surgical site 54, that will require resection during surgery, may be planned and mapped onto computer model 50 (FIGS. 2A and 2B). After the interactive processing of the digitized image data, it is possible to go back to original CAD data to obtain a higher resolution digital representation of the patient specific surgical instruments, prostheses, guides, or fixtures so as to add that digital representation to the patient's image data model.

Figure 3:
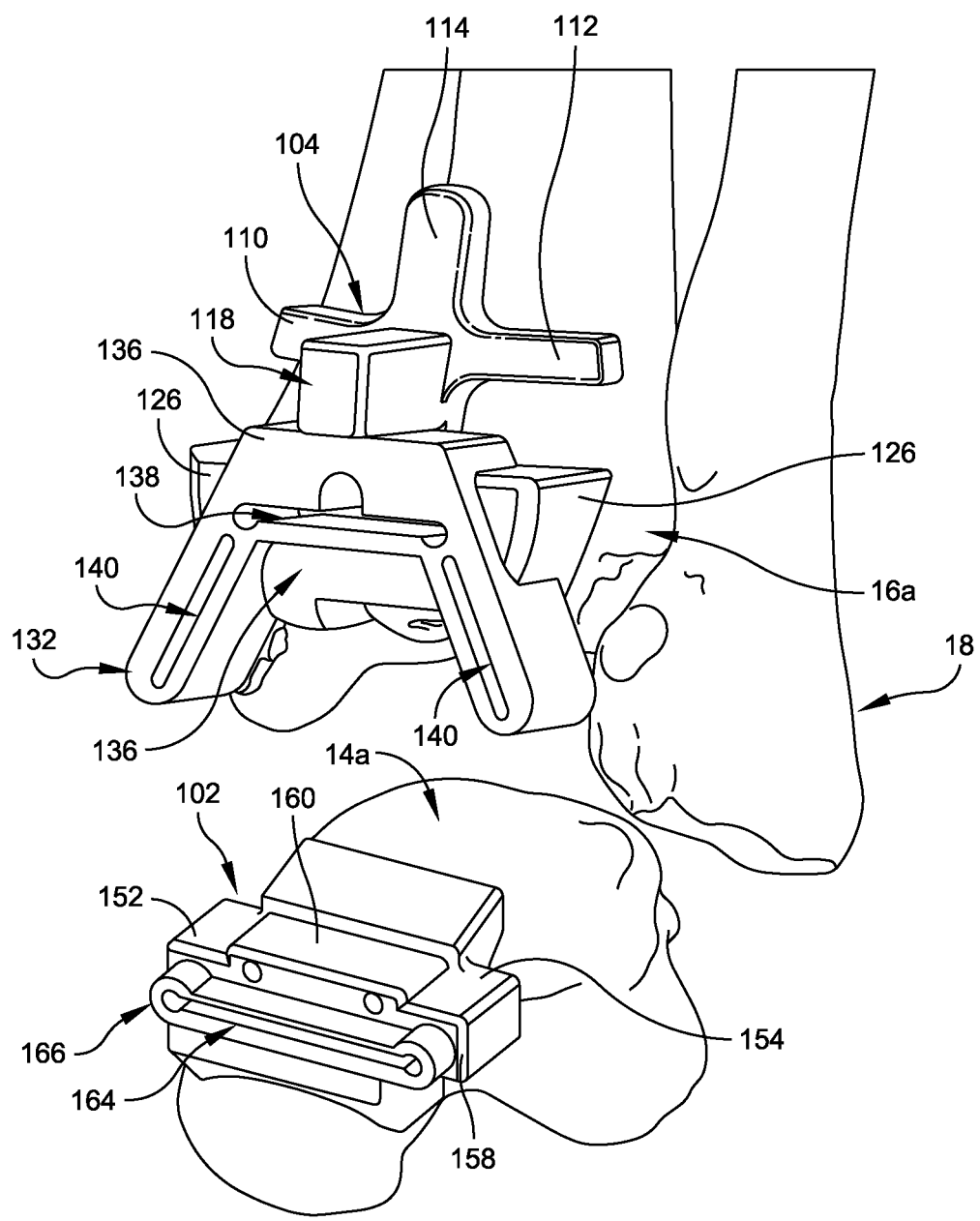
FIG. 3 is a perspective view of tibial and talar resection guides located upon portions of a tibia and a talus.

FIG. 3 illustrates a pair of custom cutting guides for an ankle replacement surgery including a tibial resection guide mount 100 and a talar resection guide mount 102, which are formed and mounted to the patient's lower tibia 16a and upper talus 14a. A custom tibial drill guide mount 200 (FIGS. 16-20) is also formed and configured to be received within ankle space created by using the custom tibial and talar resection guide mounts 100, 102. Although custom cutting guides are described for preparing a patient's talus, tibia, and femur, one skilled in the art will understand that other cutting guides may be implemented and that custom guides may be created for other joints including, but not limited to, the knee, hip, shoulder, or other joint.

Figure 4:
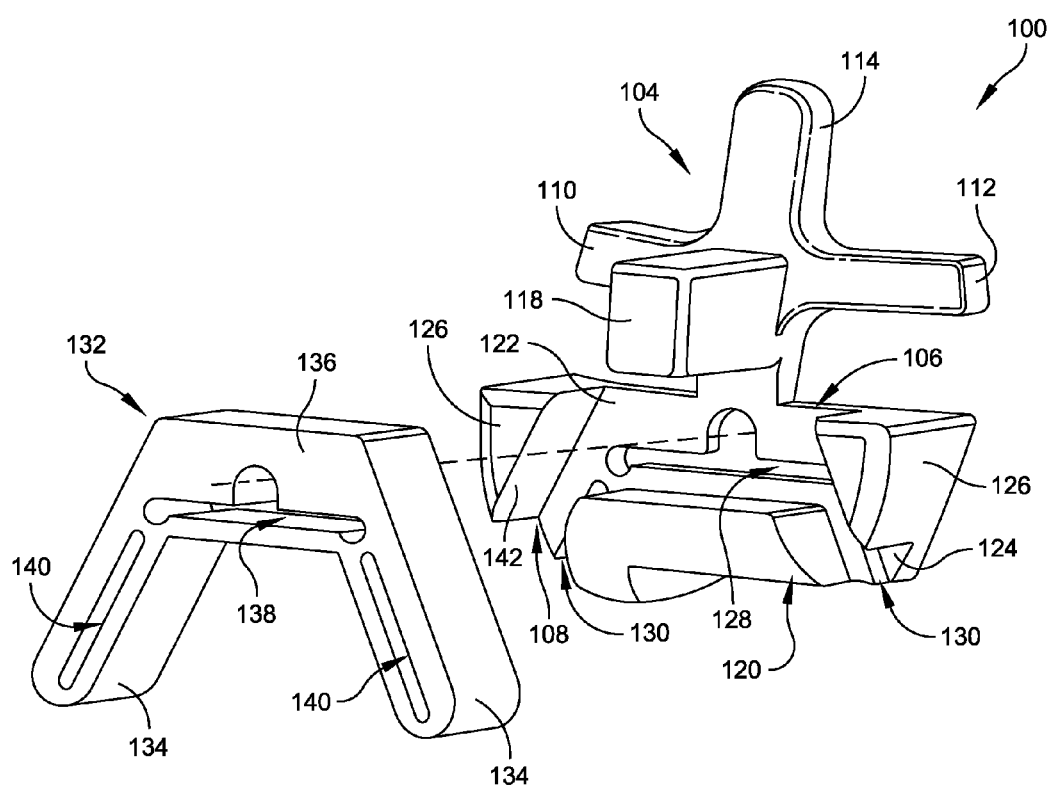
FIG. 4 is an exploded perspective view of a tibial cutting guide mount and tibial resection guide.
Figure 7:
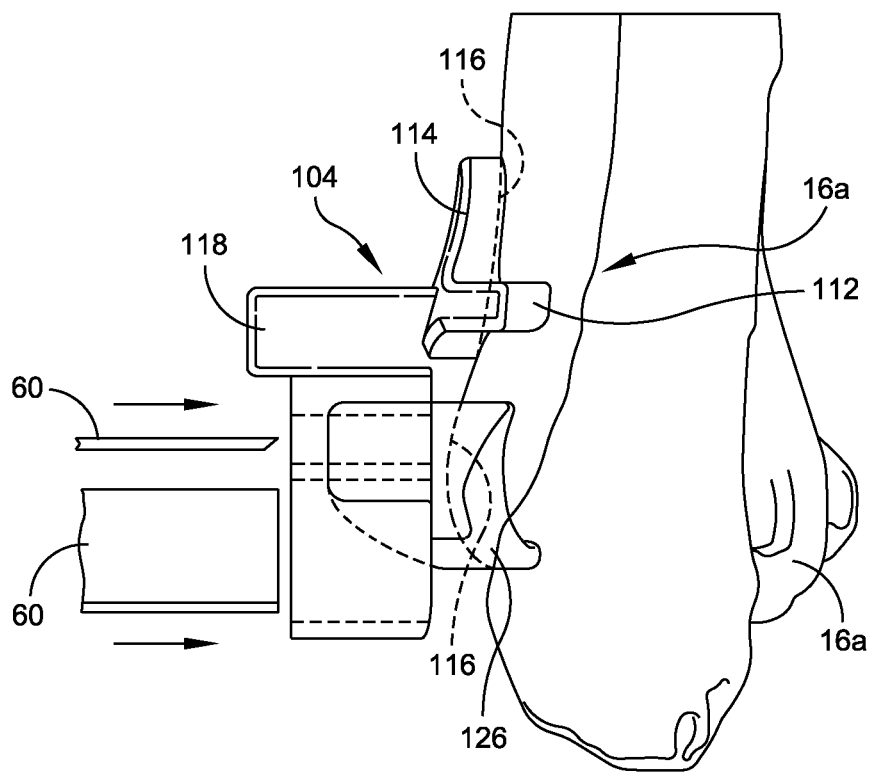
FIG. 7 is a side elevational view of a tibial cutting guide disposed within a tibial cutting guide mount located on an inferior portion of a tibia during resection of the tibia.

Tibial resection guide mount 100 illustrated in FIG. 3 is formed from a resilient polymer material of the type that is suitable for use in connection with stereo lithography, selective laser sintering, or like manufacturing equipment. Resection guide mount 100 includes a unitary body including a cruciform tibial yolk 104 projecting upwardly from a base 106 that further defines a guide receptacle recess 108 as best seen in FIG. 4. Cruciform yolk 104 includes a pair of spaced apart arms 110, 112 that project outwardly from a central post 114. Arms 110, 112 and central post 114 each have a conformal bone engaging surface 116 that is complementary to the contours of a corresponding portion of the patient's lower tibia 16a as illustrated in FIG. 7. Through the previously discussed imaging operations, conformal bone engaging surfaces 116 of arms 110, 112 and central post 114 are configured for complementary matching with anatomical surface features of a selected region of the patient's natural bone. For tibial resection guide mount 100, the selected bone region comprises the lower surfaces of the patient's tibia 16a.

Figure 5:
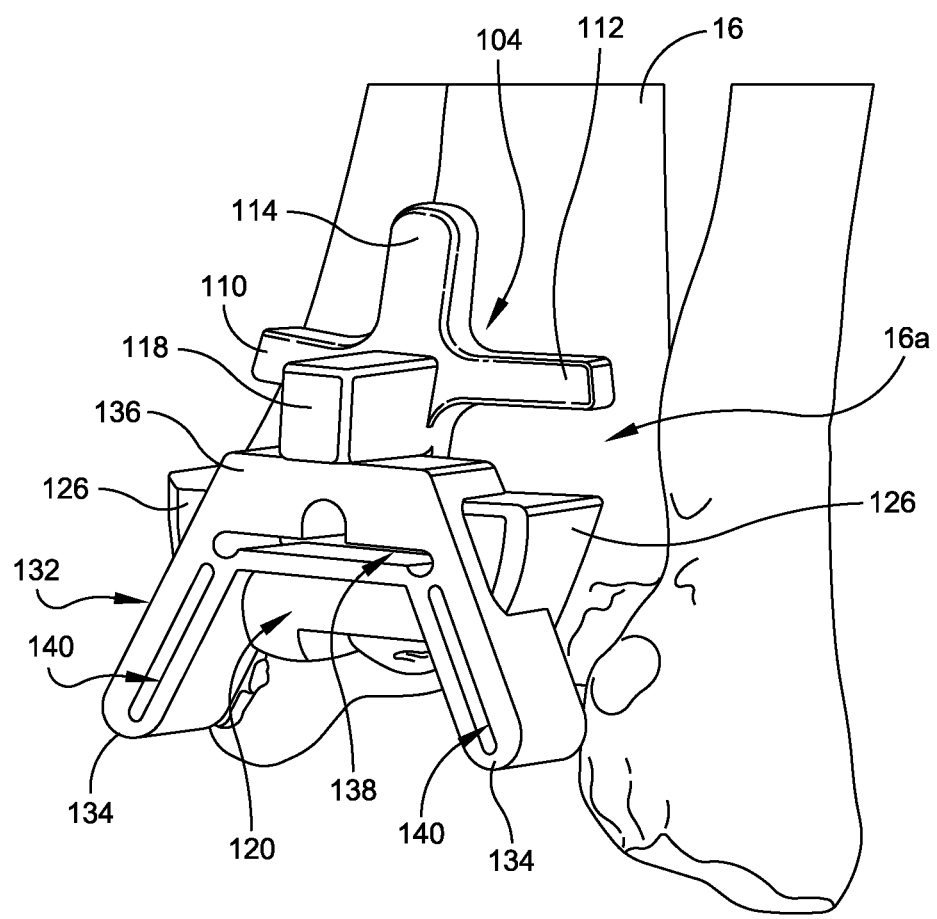
FIG. 5 is a perspective view of a tibial cutting guide disposed within a tibial cutting guide mount located on an inferior portion of a tibia.

As best seen in FIGS. 3-5, a pilot block 118 projects outwardly from central post 114, adjacent to the intersection of arms 110,112. A support block 120 (FIG. 4) is located on base 106 in spaced relation to pilot block 118. Guide receptacle recess 108 is defined by a pair of wings 122,124 that extend outwardly from either side of central post 114 in opposite directions on base 106, with support block 120 located between them. Each wing 122, 124 includes a respective pylon 126 projecting outwardly from base 106 so as to provide lateral support for tibial resection guide 132 (FIGS. 4 and 5). An elongate slot 128 is defined transversely in a central portion of base 106 below pilot block 118, but above support block 120. Each wing 122, 124 also defines a respective slot 130 that is oriented at an angle relative to central post 114. In some embodiments, slots 130 are disposed at a non-perpendicular angle relative to central post 114, although one skilled in the art will understand that slots 130 may be disposed at perpendicular angles with respect to the direction in which central post 114 extends. Slots 128 and 130 are sized and shaped to allow a typical surgical saw 60 (FIG. 7) of the type often used for bone resection, to pass through from a correspondingly positioned and sized slot in resection guide 132 without contact, or with only incidental contact with resection guide mount 100.

Referring again to FIG. 4, tibial resection guide 132 includes a pair of arms 134 that project downwardly and outwardly in diverging angular relation from the ends of a bridge beam 136. The shape of tibial resection guide 132 is complementary to the shape of guide receptacle recess 108 as defined by the inwardly facing surfaces of pilot block 118, support block 120, and pylons 126. Bridge beam 136 defines an elongate slot 138 that aligns with slot 128 when tibial resection guide is coupled to and supported by resection guide mount 100. Arms 134 each define a respective slot 140 that align with a respective slot 130.

The inwardly facing surfaces 142 of pilot block 118, support block 120, and pylons 126, that together define guide receptacle recess 108, have a shape that is complementary to the outer profile of tibial resection guide 132. Guide receptacle recess 108 is sized so as to accept tibial resection guide 132 with a "press-fit". By press-fit it should be understood that the inwardly facing surfaces 142 of pilot block 118, support block 120, and pylons 126 are sufficiently resilient to deflect or compress elastically so as to store elastic energy when tibial resection guide 132 is pushed into guide receptacle recess 108. Of course, it will also be understood that tibial resection guide 132 will have an outer peripheral shape that is complementary to the circumferential shape of guide receptacle recess 108, but slightly larger in size, for press-fit embodiments. Also, tibial resection guide 132 may be retained within guide receptacle recess 108 by only frictional engagement with the inwardly facing surfaces of pilot block 118, support block 120, and pylons 126. In some embodiments, tibial resection guide 132 can simply slide into guide receptacle recess 108 without operative contact or only incidental engagement with the inwardly facing surfaces of pilot block 118, support block 120, and pylons 126.

Figure 9:
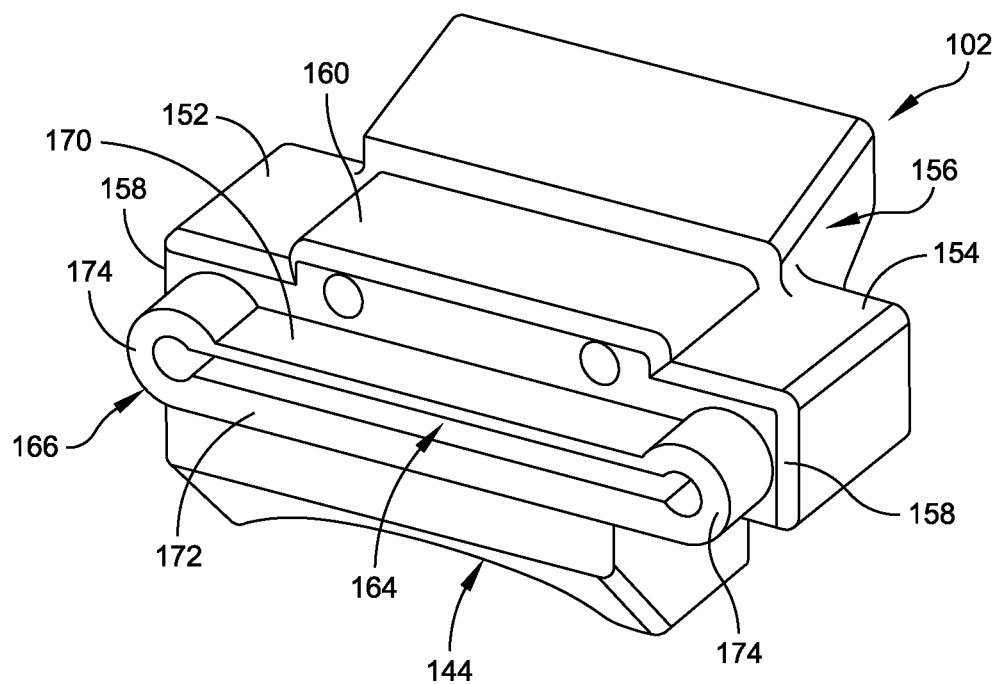
FIG. 9 is a perspective view of a talar cutting guide disposed within a talar cutting guide mount.
Figure 10:
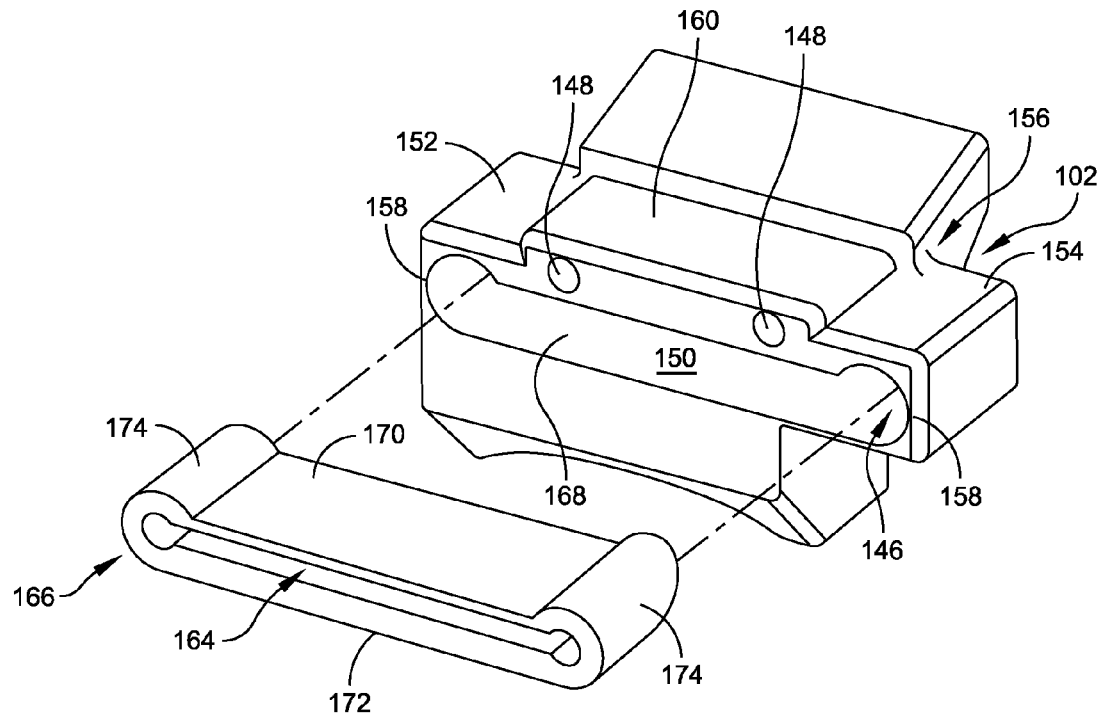
FIG. 10 is an exploded perspective view of the talar cutting guide mount and the talar cutting guide illustrated in FIG. 9.
Figure 11:
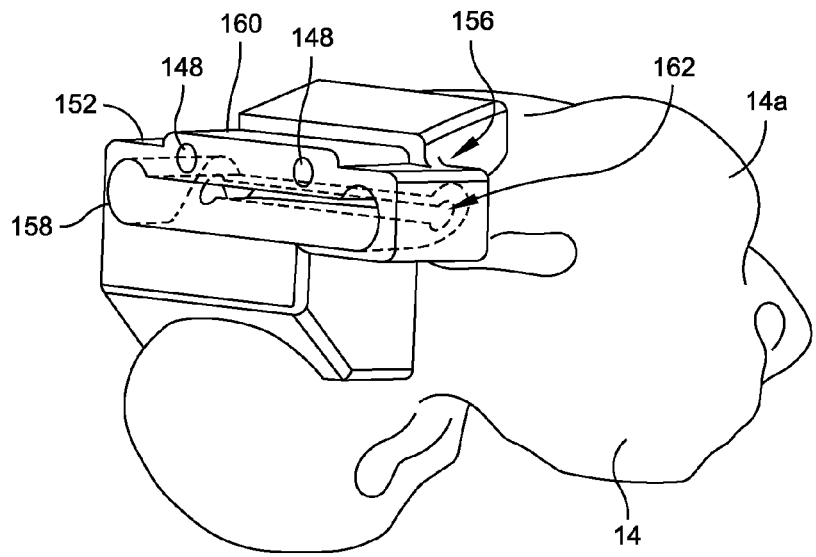
FIG. 11 is a perspective view of the talar cutting guide disposed within the talar cutting guide mount located on a superior portion of a talus.
Figure 13:
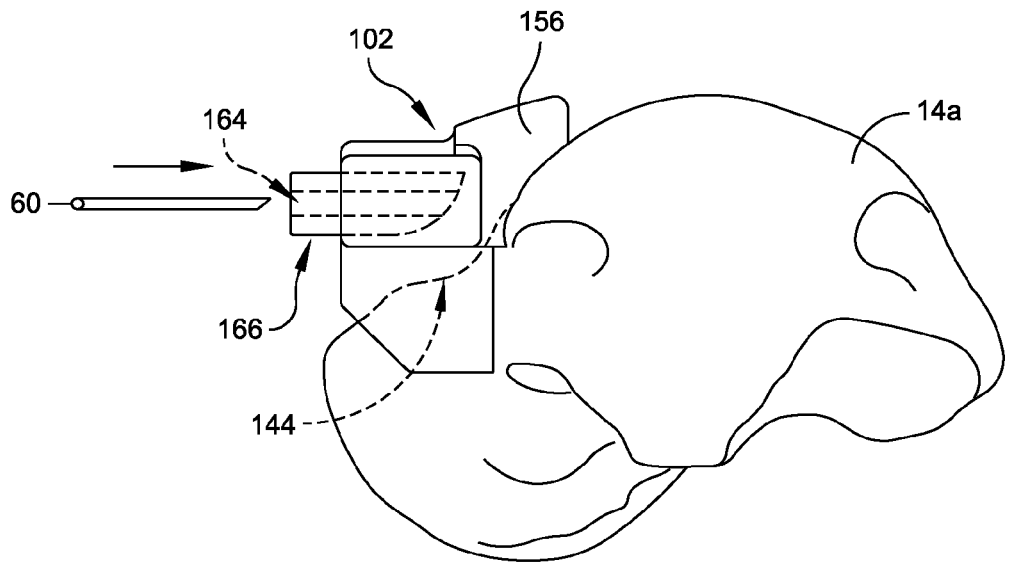
FIG. 13 is a side perspective view of the talar cutting guide disposed within the talar cutting guide mount located on a superior portion of a talus during resection of the talus.

Referring now to FIGS. 9 and 10, a talar resection guide mount 102 is formed from a resilient polymer material of the type that is suitable for use in connection with stereo lithography, selective laser sintering, or the like manufacturing equipment, e.g., a polyamide powder rapid prototype material is suitable for use in connection with selective laser sintering. Talar resection guide mount 102 also includes a conformal bone engaging surface 144 that is complementary to the contours of a corresponding portion of the patient's upper talus 14a (FIGS. 11 and 13). Through the previously discussed imaging operations, conformal bone engaging surface 144 of talar resection guide mount 102 is configured for complementary matching with anatomical surface features of a selected region of the patient's natural bone. For talar resection guide mount 102, the selected bone region comprises the outer, upper surfaces of the patient's talus.

Talar resection guide mount 102 comprises a unitary block that defines a central guide receptacle recess 146 and a pair of through-bores 148 (FIG. 10). Guide receptacle recess 146 is defined by the inwardly facing surfaces 150 of a pair of wings 152, 154 that project outwardly, in opposite directions from a base 156. Each wing 152,154 includes a pylon 158 projecting upwardly to support guide housing 160 such that an elongate slot 162 is defined within base 156 and below guide housing 160 (FIGS. 10 and 11). Slot 162 is sized and shaped to allow a typical surgical saw 60, of the type often used for bone resection, to pass through from a correspondingly positioned and sized slot 164 in talar resection guide 166 without contact, or with only incidental contact with talar resection guide locator 102 (FIGS. 11 and 13). An annular wall 168, having a shape that is complementary to the outer profile of talar resection guide 166, projects outwardly in substantially perpendicular relation to a back wall and so as to further defines guide receptacle recess 146.

Still referring to FIGS. 9 and 10, talar resection guide 166 includes a pair of confronting, parallel plates 170, 172 that define elongate slot 164 between them, and are joined to one another at their ends by wings 174. In this way, the shape of talar resection guide 166 is complementary to the shape of guide receptacle recess 146 as defined by the inwardly facing surfaces 150 of wings 152, 154, base 156, and pylons 158. Guide receptacle recess 146 is sized so as to accept talar resection guide 166 with a press-fit. Of course, it will also be understood that talar resection guide 166 will have an outer peripheral shape that is complementary to the circumferential shape of guide receptacle recess 146, but slightly larger in size, for press-fit embodiments. Also, talar resection guide 166 may be retained within guide receptacle recess 146 by only frictional engagement with the inwardly facing surfaces 150 of wings 152, 154, base 156, and pylons 158. In some embodiments, talar resection guide 166 can simply slide into guide receptacle recess 146 without operative contact or only incidental engagement with the inwardly facing surfaces 150 of wings 152, 154, base 156, and pylons 158.

Figure 8:
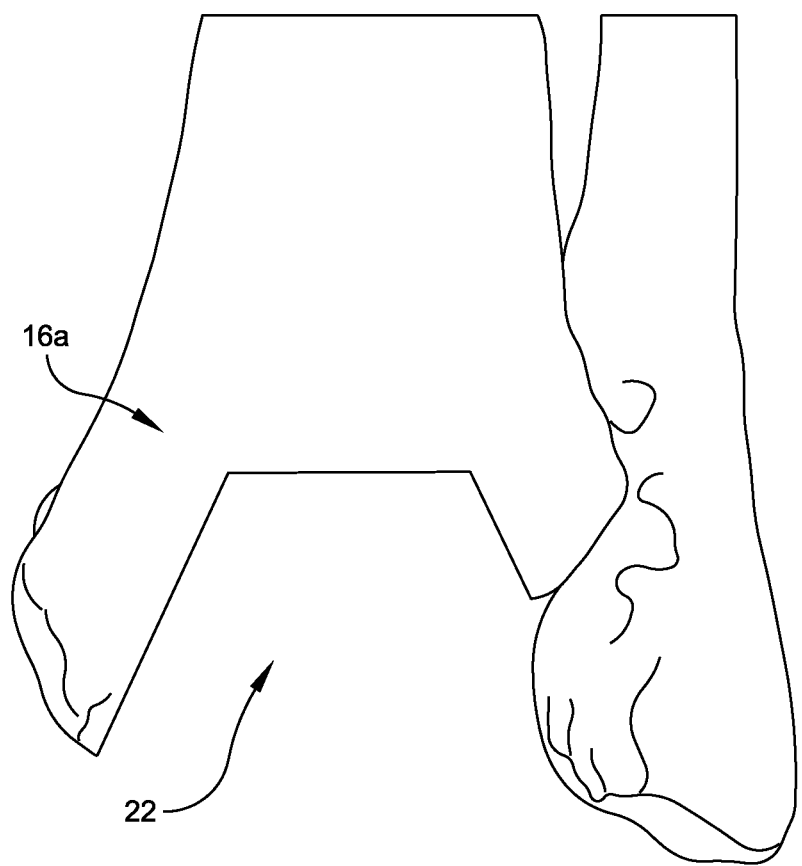
FIG. 8 is a schematic representation of a resected tibia following application and use of the tibial cutting guide and tibial cutting guide mount.

Tibial drill guide mount 200 illustrated in FIGS. 16-20 also may be fabricated from a resilient polymer material of the type that is suitable for use in connection with stereo lithography, selective laser sintering, or the like manufacturing equipment, e.g., a polyamide powder repaid prototype material is suitable for use in connection with selective laser sintering. As shown in FIGS. 16-20, tibial drill guide mount 200 includes a somewhat rectangular body 204 that defines an aperture 206 that extends from a top surface 208 of body 204 to a bottom surface 210 of body 204. Top surface 208 of body 204 may include a pair of chamfers 212 that are sized and configured to be mate against the resected surfaces of the lower tibia 16a (FIG. 8). Put another way, the top or upper surface 208 of body 204, including chamfers 212, is complementary to the geometry and locations of slots 138 and 140 of tibial resection guide 132.

Front side 214 of body 204 defines one or more blind holes 216. As illustrated in the embodiment shown in FIG. 17, body 204 may define three blind holes 216-1, 216-2, and 216-3. In some embodiments, blind holes 216-1 and 216-2 may be reamed holes that are sized and configured to receive a dowel pin, and blind hole 216-3 may also be a reamed hole for receiving a dowel pin or blind hole 216-3 may be threaded for engaging a screw as described below.

Figure 20:
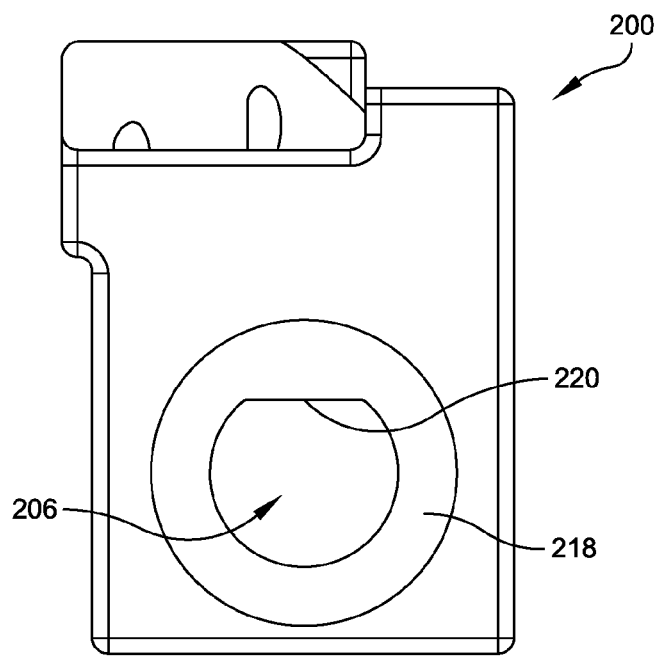
FIG. 20 is a top elevational view of the tibial drill guide mount illustrated in FIG. 16.

Aperture 206 may have a circular cross sectional area and include a shoulder 218 having a reduced diameter compared to aperture 206 and includes an anti-rotational feature 220 as best seen in FIG. 20. Anti-rotational feature 220 of shoulder 218 may include one or more flats or other geometric structure(s) to prevent tibial drill guide 202 from rotating with respect to tibial drill guide mount 200 when tibial drill guide 202 is disposed within aperture 206.

Extending from body 204 of tibial drill guide mount 200 are tibial engagement structure 222 and talar engagement structure 224. The outer surface 226 of tibial engagement structure 222 may have a rectangular shape that is substantially planar, and the internal and substantially conformal engagement surface 228 of tibial engagement structure 222 may be somewhat convex for engaging the tibia 16 of the patient. Tibial engagement structure 222 may define one or more holes 230 for receiving a k-wire or pin as described below.

Figure 14:
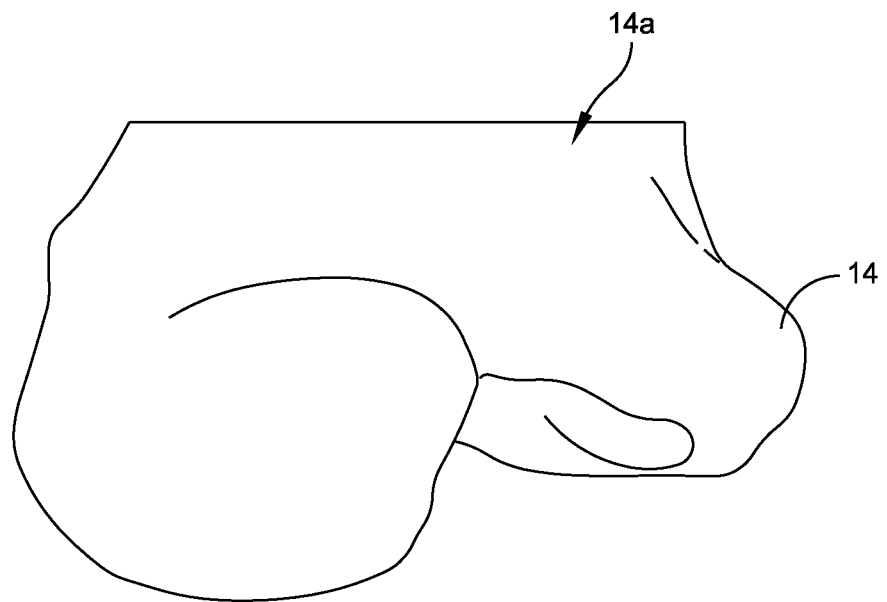
FIG. 14 is a schematic representation of a resected talus following application and use of the talar cutting guide and talar cutting guide mount.

Talar engagement structure 224 may also include a substantially planar and rectangular outer surface 232. The lower portion 234 of talar engagement structure 224 may be a conformal surface having a geometry that matches the geometry of the talar bone 14 (FIG. 14). Talar engagement structure 224 may also define one or more holes 236 sized and configured to receive a k-wire as described below.

Figure 21:
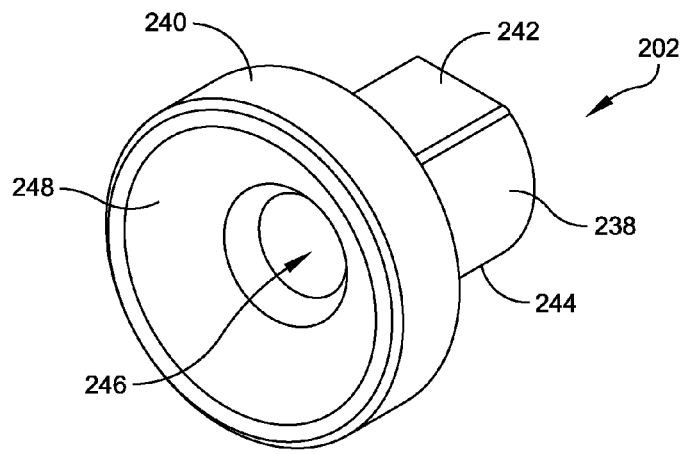
FIG. 21 is a perspective view of one example of a tibial drill guide.
Figures 22, 23:
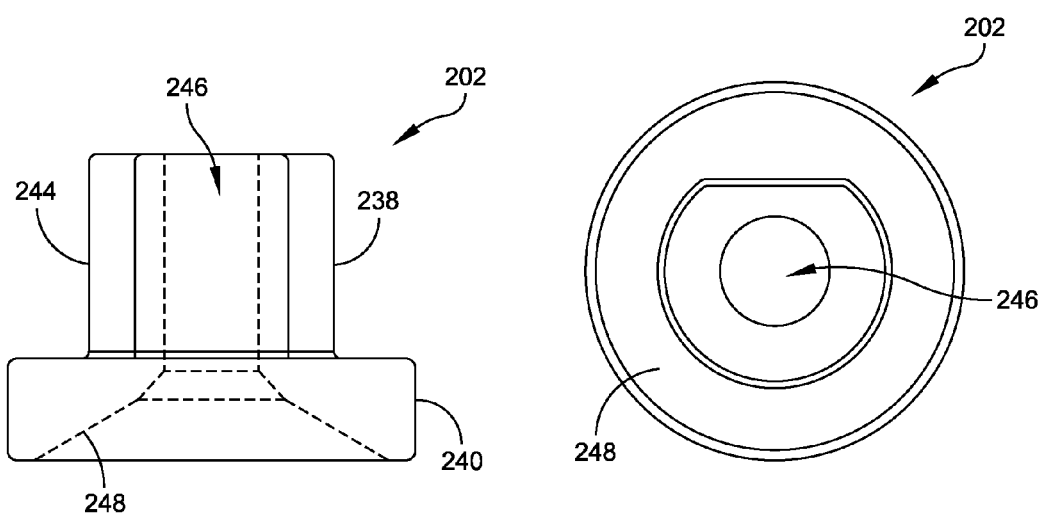
FIG. 22 is a side elevational view of the tibial drill guide illustrated in FIG. 21.
FIG. 23 is a top elevational view of the tibial drill guide illustrated in FIG. 21.

Tibial drill guide 202 illustrated in FIGS. 21-23 is preferably fabricated from a material having more structural integrity than tibial drill guide mount 200 to enable drill guide 202 to guide a drill bit without being damaged. Examples of materials include, but are not limited to, metals, ceramics, or the like. Drill guide 202 has a cylindrically shaped first portion 238 that is sized and configured to be received within the portion of aperture 206 that extends through the shoulder or reduced diameter area 218. A second portion 240 of drill guide 202 has a larger cross-sectional diameter than first portion 238 and is sized and configured to be received within aperture 206 of tibial drill guide mount 200. A flat 242, which is best seen in FIGS. 21 and 23, is formed along an exterior surface 244 of first portion 238 of drill guide 202. The internal surface 248 of second portion 240 of tibial drill guide 202 has a conical shape that intersects and communicates with aperture 246 such that a drill or reamer may be received through drill guide 202.

As with the digital image models 50 disclosed above, and considering a generalized digital model of a tibial resection guide mount 100 added to the patient's lower tibia image data, the anatomic surface features of the patient's lower tibia, e.g., the surface topography, may be complementarily mapped onto each of conformal bone engaging surfaces 116 of arms 110, 112, and central post 114, i.e., the surfaces that will engage the bones unique surface topography, of tibial resection guide mount 100. It will be understood that complementary mapping of the digital images results in localized prominences on the surface of a bone becoming localized concavities on conformal bone engaging surfaces 116 of arms 110, 112, and central post 114 of tibial resection guide mount 100, while localized concavities on the surface of a bone become localized prominences on conformal bone engaging surfaces 116 of arms 110, 112, and central post 114.

Each of conformal bone engaging surfaces 116 of arms 110, 112, and central post 114 of resection guide mount 100 is redefined with a complementary, substantially mirror image of the anatomic surface features of a selected region of the patient's lower tibia 16a. As a consequence of this complementary bone surface mapping, tibial resection guide mount 100 releasably "locks" on to the complementary topography of the corresponding portion of the patient's natural tibia without the need for other external or internal guidance fixtures. In other words, the mating of bone surface asperities in their corresponding concavities formed in conformal bone engaging surfaces 116 of tibial resection guide mount 100 ensures that little or no relative movement, e.g., slipping sideways, occurs between tibial resection guide mount 100 and the tibial surface.

A substantially identical mapping is carried out in connection with the design of a patient specific talar resection guide mount 102 and tibial drill guide mount 200. Notably, the mapping for the design of tibial drill guide mount 200 is performed by extrapolating where the resections to the tibia 16 and talus 14 will be made using tibial and talar resection guide mounts 100 and 102 and mapping the tibial drill guide mount 200 onto the extrapolated geometry of the tibia and talus.

A visual presentation of the virtual alignment results between the patient's lower tibia 16a and resection guide mount 100, the patient's upper talus 14a and resection guide mount 102, and the proposed resected area that that is to be created by resecting the talus 14 and tibia utilizing the tibial resection guide mount 100 and the talar resection guide mount 102 are created and forwarded to the surgeon to obtain approval of the results prior to manufacturing. Additionally, the surgeon may be provided with a visual representation of the virtual alignment results between the proposed resected joint space and tibial drill guide mount 200 are created and forwarded to the surgeon to obtain approval of the results prior to manufacturing. Upon receipt of the surgeon's approval, resection guide mount 100, resection guide mount 102, and tibial drill guide mount 200 are manufactured and returned to the surgeon for use in the surgery.

Figure 6:
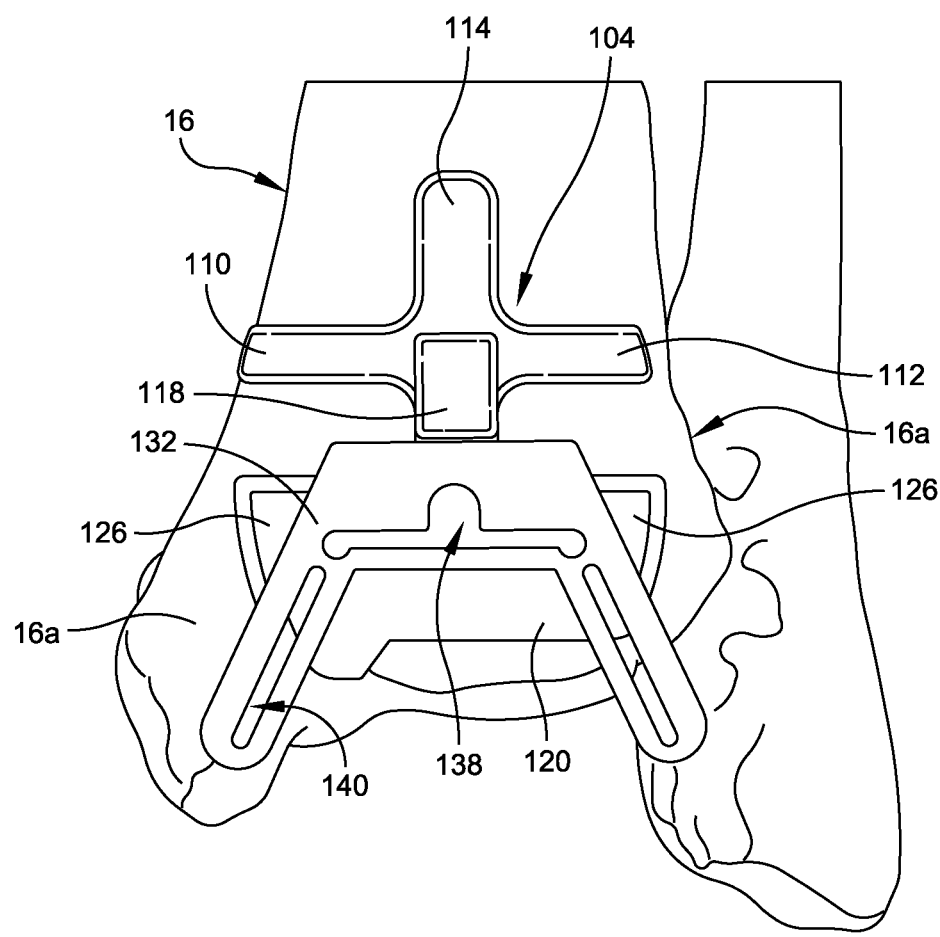
FIG. 6 is a front elevational view of a tibial cutting guide disposed within a tibial cutting guide mount located on an inferior portion of a tibia.

During a total ankle replacement, for example, the surgeon makes an anterior incision to gain initial access to the ankle joint. The surgeon orients tibia resection guide mount 100 on lower tibia 16a until the conformal bone engaging surfaces 116 of arms 110, 112 and central post 114 of tibial resection guide mount 100 securely engage one another so as to releasably "interlock" with the topography of the exposed surface of lower tibia 16a as best seen in FIGS. 5-7. With tibial resection guide mount 100 locked onto the patient's lower tibia 16a, a surgeon press-fits an appropriately configured distal resection guide 132 in guide receptacle recess 108 of tibial resection guide mount 100. This results in the resection guide mount 100 being sandwiched between the resection guide 132 and the patient's bone tibia 16a (FIGS. 5 and 6). With the resection guide mount 100 accurately positioned with respect to the selected bone region and resection guide mount 100 construct appropriately secured to the patient's bone by virtue of the mating of bone surface asperities in their corresponding concavities formed in conformal bone engaging surfaces 116, the surgeon uses a conventional surgical blade 60 and the resection slots 128 and 130 of resection guide 132 to resect the patient's bone 16 (FIGS. 7 and 8).

In a similar fashion, when talar resection guide mount 102 is added to the patient's talar image data, the anatomic surface features of the patient's upper talus, e.g., the surface topography, may be complementarily mapped onto conformal bone engaging surface 144. It will again be understood that complementary mapping of the digital images results in localized prominences on the surface of a bone becoming localized concavities on conformal bone engaging surface 144, while localized concavities on the surface of a bone become localized prominences on conformal bone engaging surface 144. In this way, conformal bone engaging surface 144 is redefined with a complementary, substantially mirror image of the anatomic surface features of a selected region of the patient's lower tibia. As a consequence of this complementary bone surface mapping, talar resection guide mount 102 releasably "locks" on to the complementary topography of the corresponding portion of the patient's natural talus without the need for other external or internal guidance fixtures.

Figure 12:
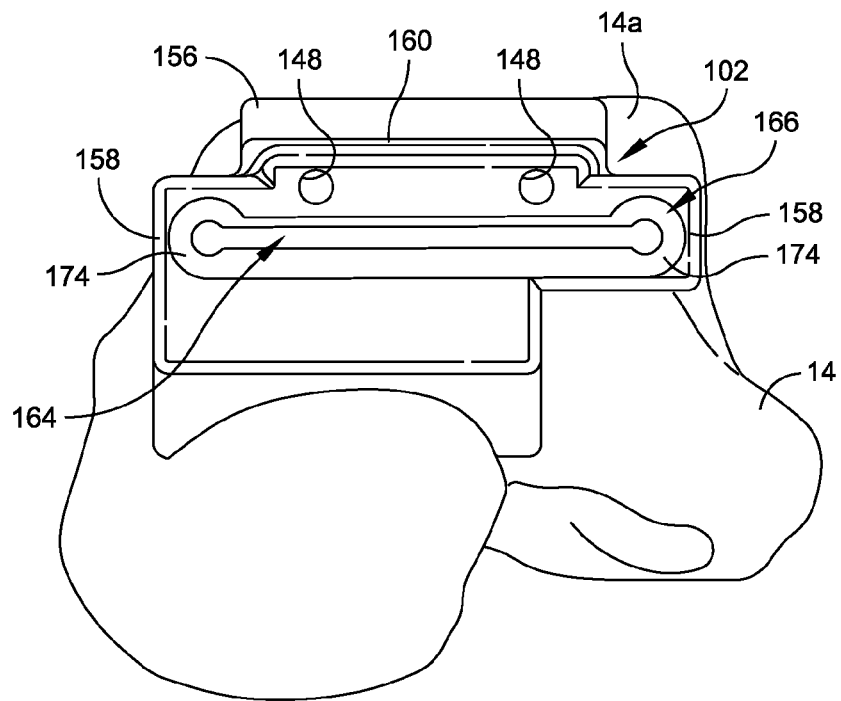
FIG. 12 is a front elevational view of the talar cutting guide disposed within the talar cutting guide mount located on a superior portion of a talus.

To continue the total ankle replacement the surgeon orients resection guide mount 102 on upper talus 14a until conformal bone engaging surface 144 of resection guide mount 102 "locks" to the topography of the exposed surface of upper talus 14a (FIG. 11). With resection guide mount 102 locked onto the patient's upper talus, a surgeon press-fits an appropriately configured distal resection guide 166 in guide receptacle recess 146 of talar resection guide mount 102. This results in resection guide mount 102 being sandwiched between resection guide 166 and the patient's bone 14 (FIGS. 12 and 13). With the resection guide mount 102 accurately positioned with respect to the selected bone region and resection guide 166 and guide mount 102 appropriately constructed and secured to the patient's bone, by virtue of the mating of bone surface asperities in their corresponding concavities formed in conformal bone engaging surfaces 144, the surgeon uses a conventional surgical blade 60 and the resection slot 164 of resection guide 166 to resect the patient's bone 14 (FIGS. 13 and 14).

Figure 15:
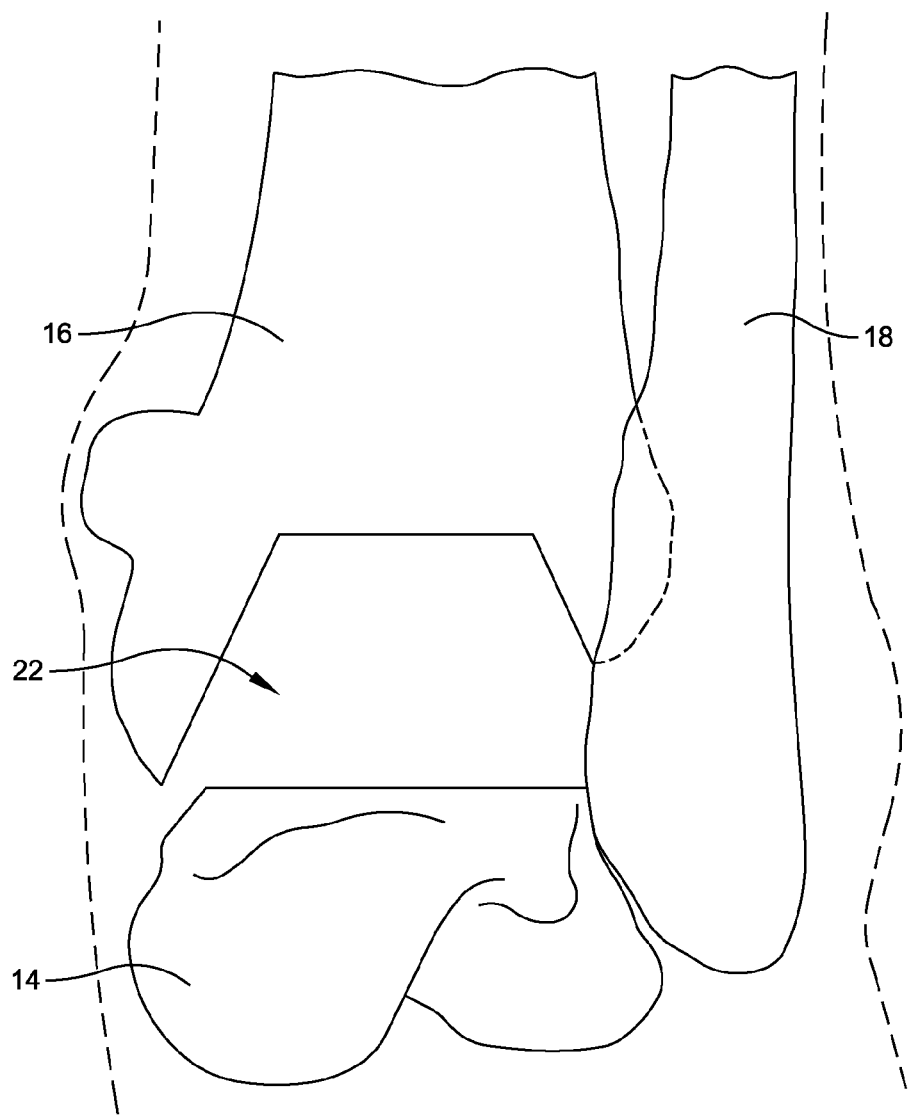
FIG. 15 is a schematic representation of a resected joint space following application and use of the talar and tibial cutting guide mounts and cutting guides.
Figure 16:
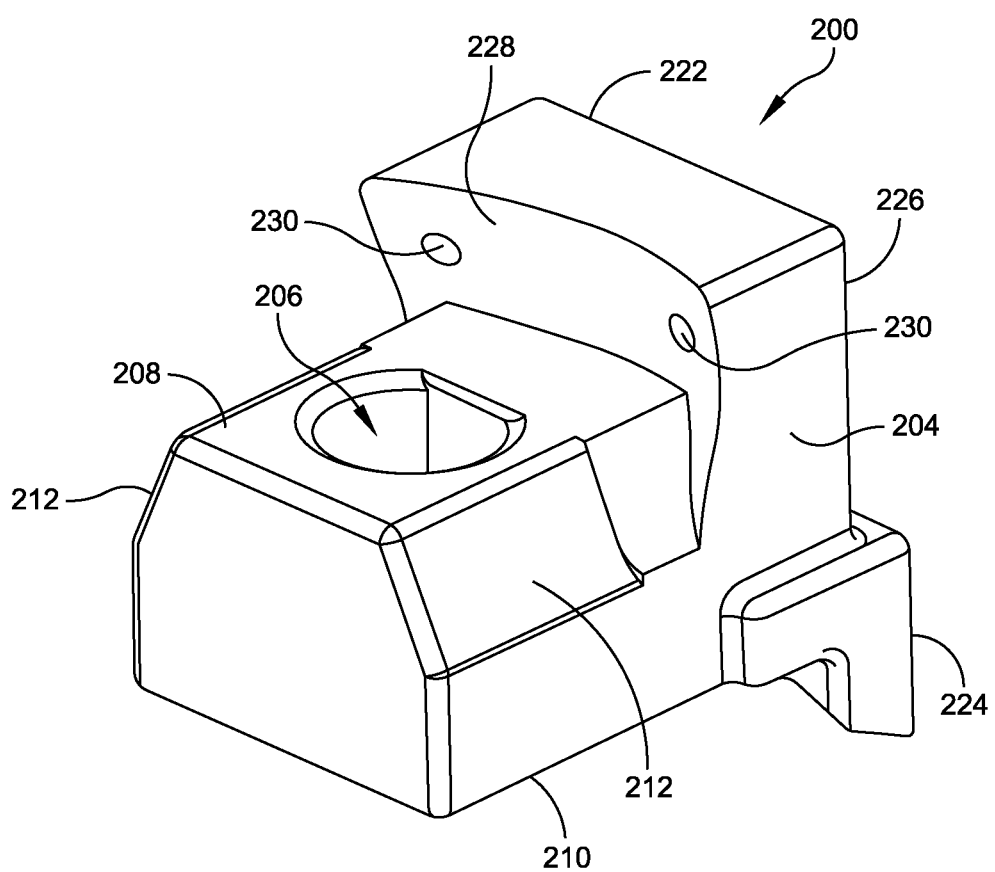
FIG. 16 is a perspective view of one example of a custom tibial drill guide mount.
Figure 17:
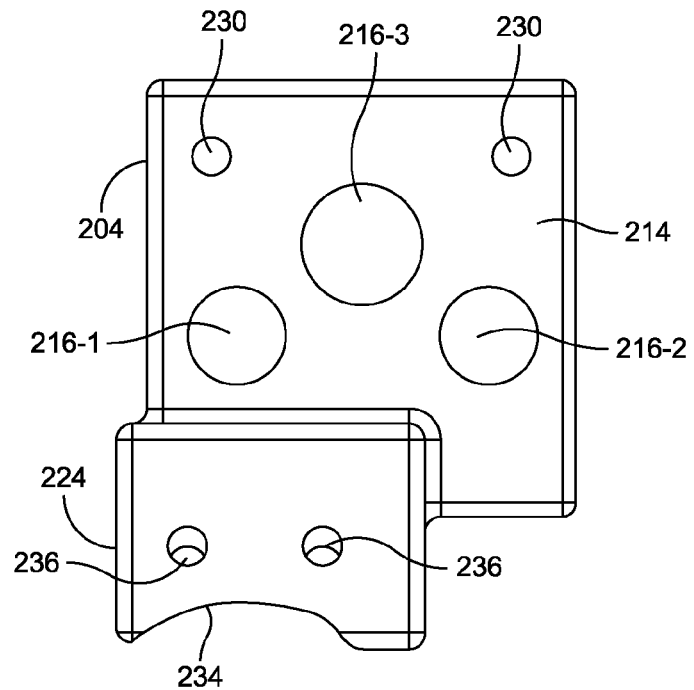
FIG. 17 is a front elevational view of the tibial drill guide mount illustrated in FIG. 16.
Figure 18:
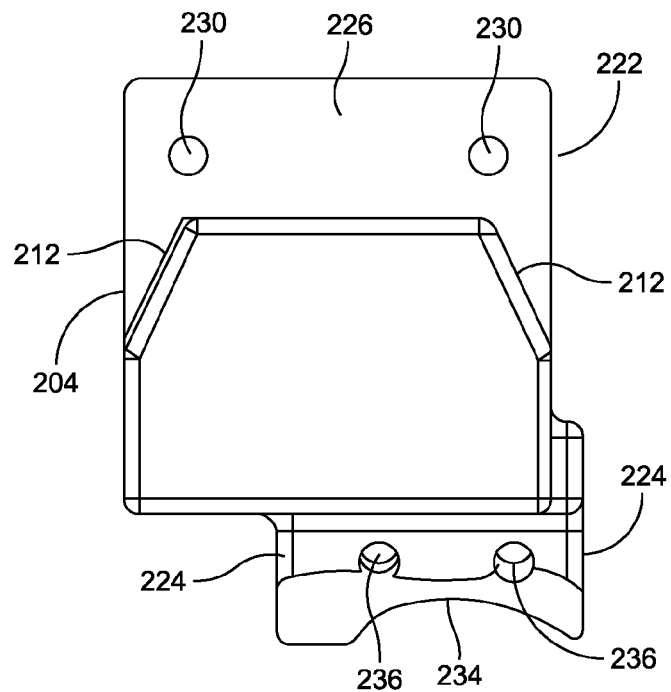
FIG. 18 is a rear elevation view of the tibial drill guide mount illustrated in FIG. 16.
Figure 19:
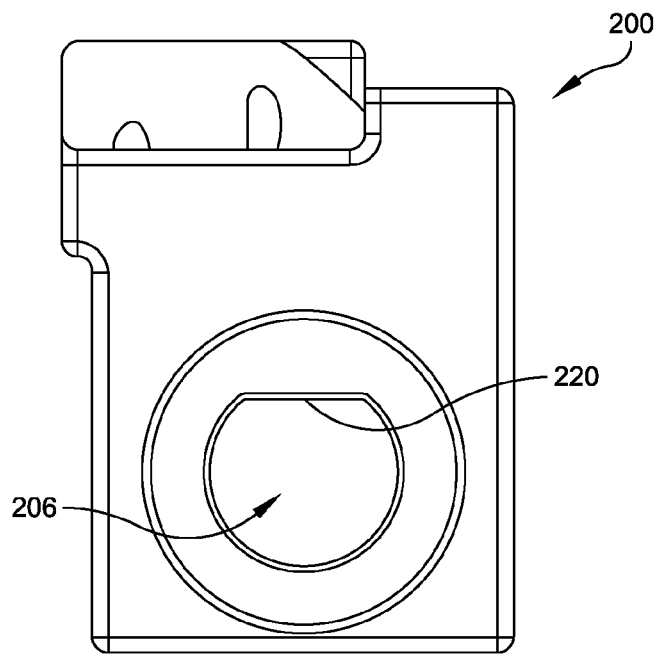
FIG. 19 is a bottom elevational view of the tibial drill guide mount illustrated in FIG. 16.
Figure 24:
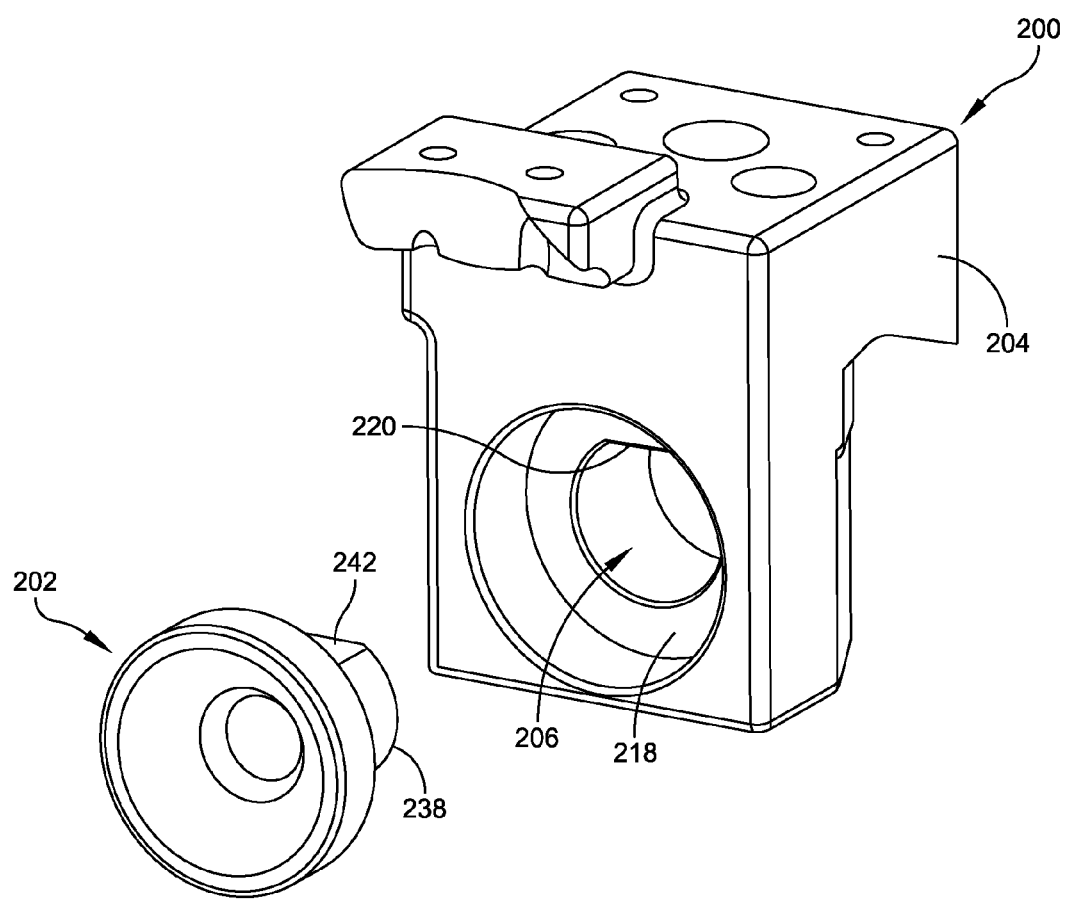
FIG. 24 is an exploded perspective view of the tibial drill guide mount and the tibial drill guide.

Once the tibia 16 and talus 14 have been resected, tibial drill guide mount 200 and tibial drill guide 202 are coupled together and installed into resected joint space 22 (FIG. 15). Tibial drill guide mount 200 and tibial drill guide 202 are coupled together by inserting first portion 238 of tibial drill guide 202 into aperture 206 defined by body 204 of tibial drill guide mount 200 (FIG. 24). Flat 242 formed on the first portion 238 of tibial drill guide 202 is aligned with anti-rotation feature 220 of shoulder 218 such that tibial drill guide 202 slides into aperture 206 until a lower surface 250 of second portion 240 of drill guide 202 contacts and abuts shoulder 218 of tibial drill guide mount 200.

Figure 25A:
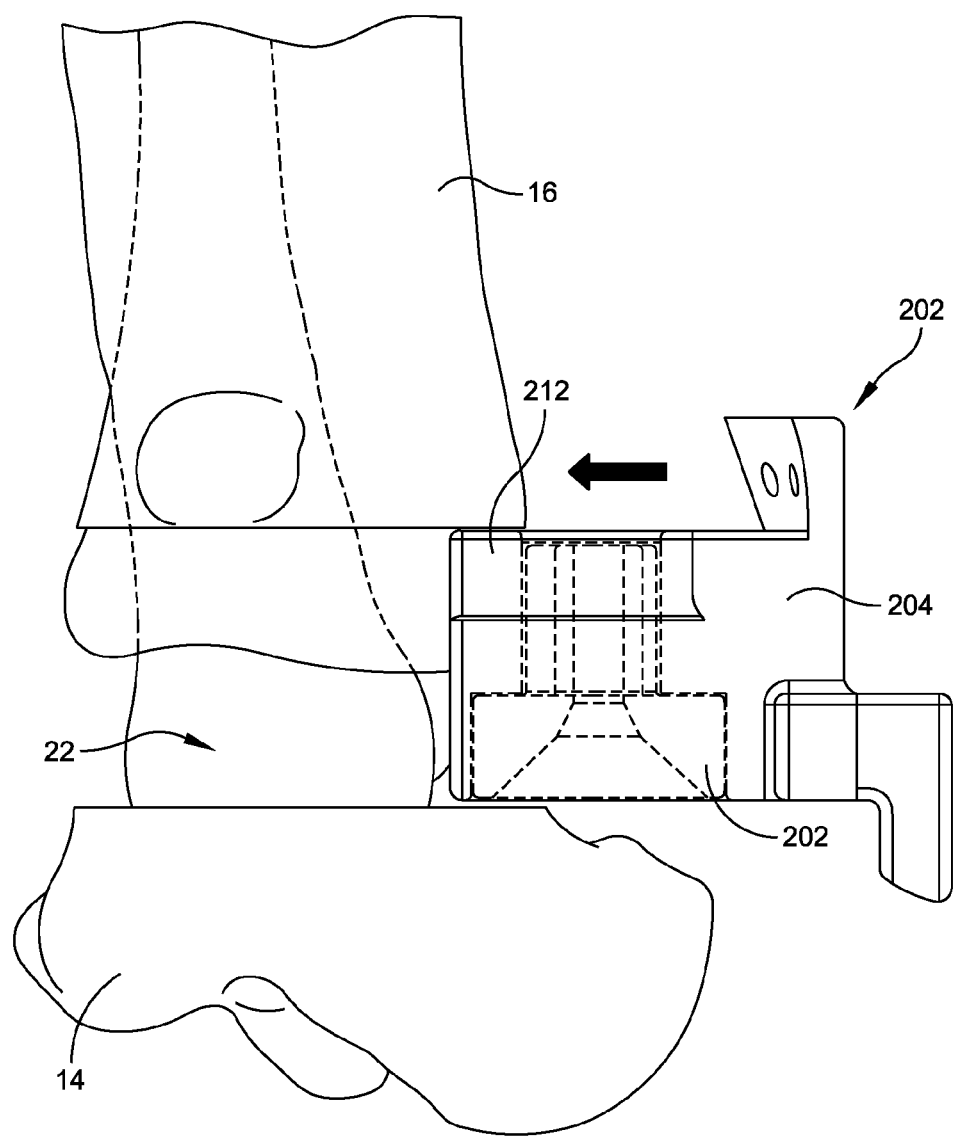
FIG. 25A is a side elevational view of the tibial drill guide disposed within the tibial drill guide mount being inserted into resected joint space.
Figure 25B:
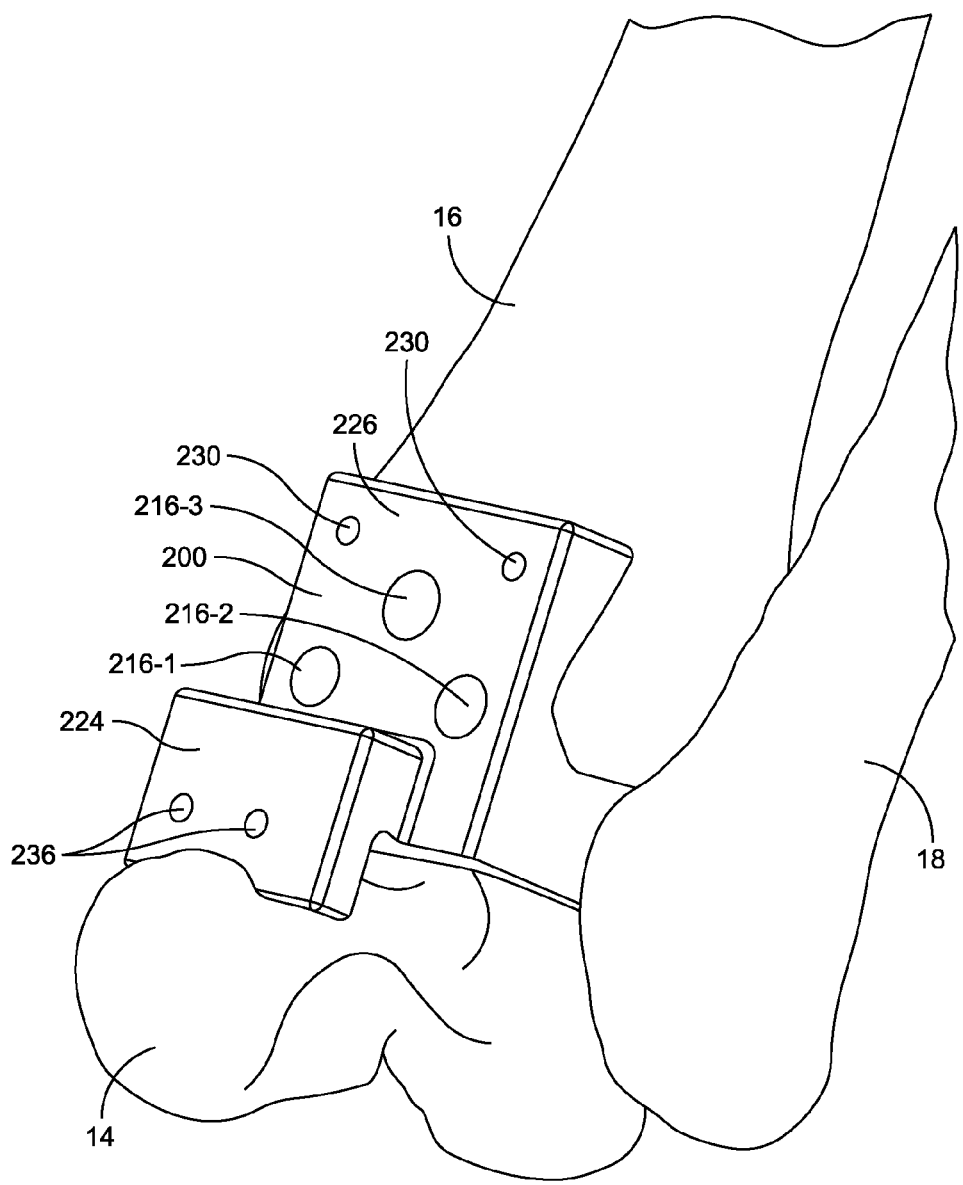
FIG. 25B is a perspective view of the assemblage of the tibial drill guide mount and tibial drill guide disposed within the resected joint space.
Figure 25C:
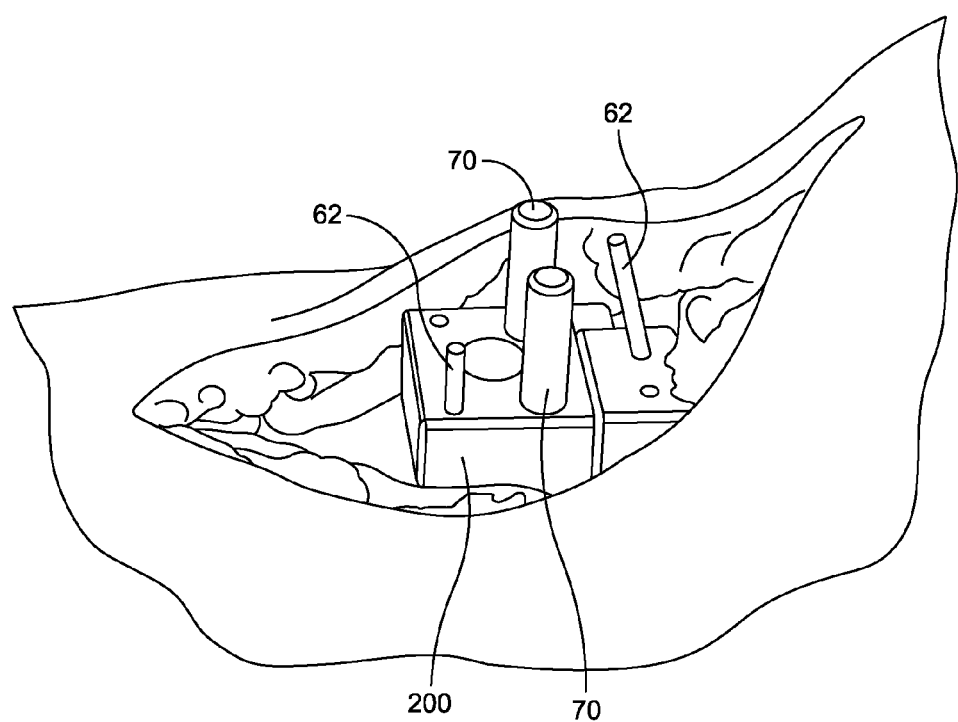
FIG. 25C is a perspective view of the assembly of the tibial drill guide mount and tibial drill guide disposed and pinned within the resected joint space.

Body 204 of tibial drill guide mount 200, in which tibial drill guide 202 is disposed, is inserted into resected joint space 22 in an anterior posterior direction with chamfers 212 sliding along resected areas of tibia 16 formed by utilizing slots 140 of tibial resection guide 132 as best seen in FIGS. 25A and 25B. The assemblage of tibial drill guide mount 200 and tibial drill guide 202 are slid into resected joint space 22 until talar engagement structure contacts talus 14. A surgeon may move tibial guide mount 200 within resected joint space until conformal surface 228 is appropriately secured to the patient's bone by virtue of the mating of bone surface asperities in their corresponding concavities formed in conformal bone engaging surface 228. Once properly located, k-wires 62 may be inserted into holes 230 and/or holes 236, respectively defined by tibial engagement structure 222 and talar engagement structure 224, to secure the assemblage of the tibial drill guide mount 200 and tibial drill guide 202 to the patient's tibia 16 and talus 14 as illustrated in FIG. 25C.

With tibial drill guide mount 200 and tibial drill guide 202 secured within resected joint space 22, the patient's leg is inserted into a foot holder and alignment tool 300. FIGS. 26-28B illustrate one example of an alignment tool 300, which serves the task of supporting the ankle joint during a prosthesis installation procedure. Alignment tool 300 includes a foot holder assembly 302 and a leg rest 304. Foot holder assembly 302 includes a foot rest 306, to which the foot is secured by a foot clamp 310 and heel clamps 308 during an prosthesis installation procedure. The calf of the leg is suitably secured to the leg rest 304 once the ankle joint has been resected and tibial drill guide mount 200 and tibial drill guide 200 have been installed. Together, foot holder assembly 302 and leg rest 304 hold the foot and ankle relative to the leg during an installation procedure.

Figure 26:
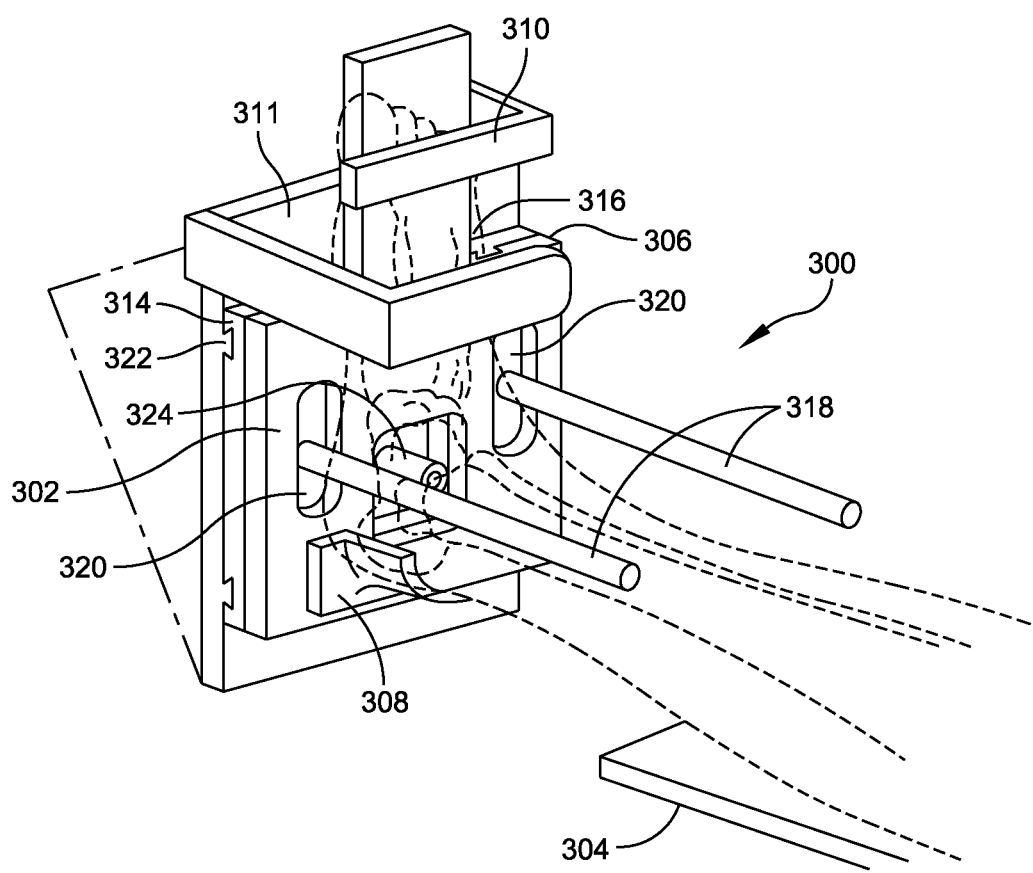
FIG. 26 is a perspective view of one example of an alignment tool.

As shown in FIG. 26, foot holder assembly 302 is sized and configured for pivoting, under control of the physician, from a vertical or upright condition (shown in solid lines in FIG. 26) toward a more horizontal or tilted condition (shown in phantom lines in FIG. 26). In the upright condition, assembly 302 serves to hold the ankle joint in a desired orientation with respect to the natural anterior-to-posterior and medial-to-lateral axes.

Figure 27:
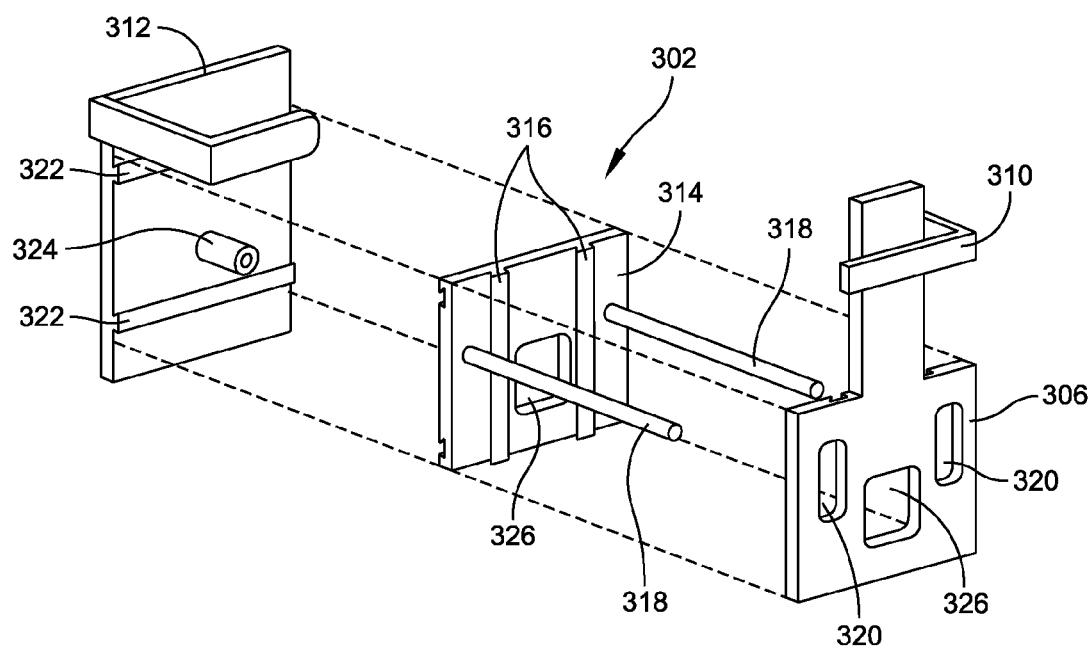
FIG. 27 is an exploded perspective view of the alignment tool illustrated in FIG. 26.

As best seen in FIG. 27, foot holder assembly 302 includes a back plate 312 and a mid-plate 314, which is sandwiched between foot rest 306 and back plate 312. Mid-plate 314 is coupled to the foot rest 306 by sliding dovetail couplings 316 for up-and-down (i.e., vertical) movement relative to foot rest 306. A pair of oppositely spaced alignment rods 318 is carried by the mid-plate 314.

Figure 28A:
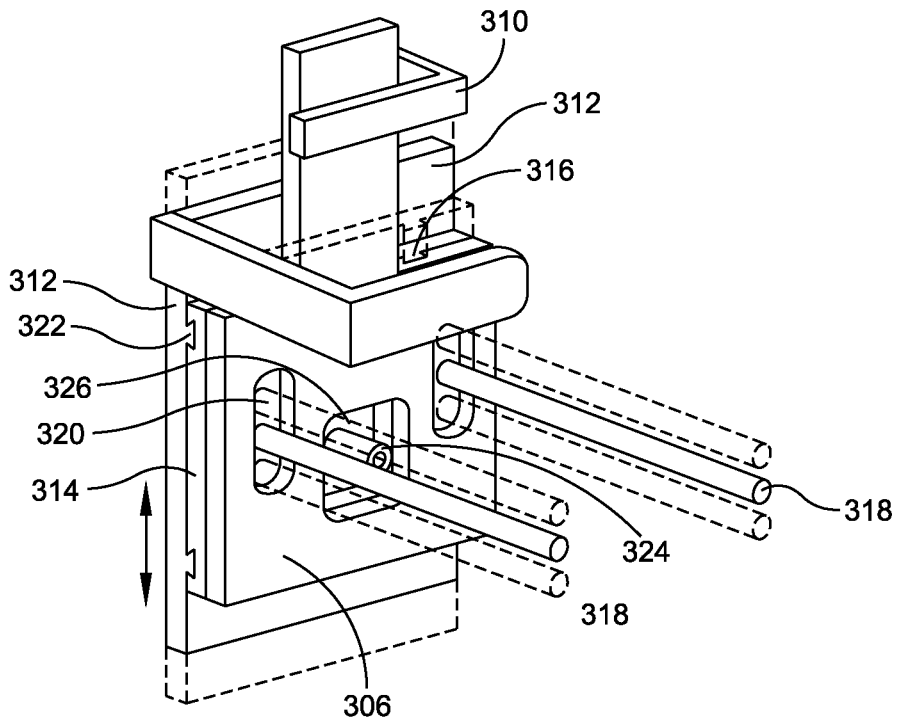
FIGS. 28A and 28B illustrate the relative movement permitted between each of the components of the alignment tool illustrated in FIG. 26.

Alignment rods 318 are disposed in the same horizontal plane and extend from mid-plate 314 through vertically elongated slots 320 defined by foot rest 306 such that rods 318 are disposed on opposite sides of the tibia in the medial-to-lateral plane when a foot is supported by foot holder assembly 302. Vertical movement of mid-plate 314 moves alignment rods 318 up-and-down in unison within slots 320 on opposite sides of the foot rest 306 (FIG. 28A).

Figure 28B:
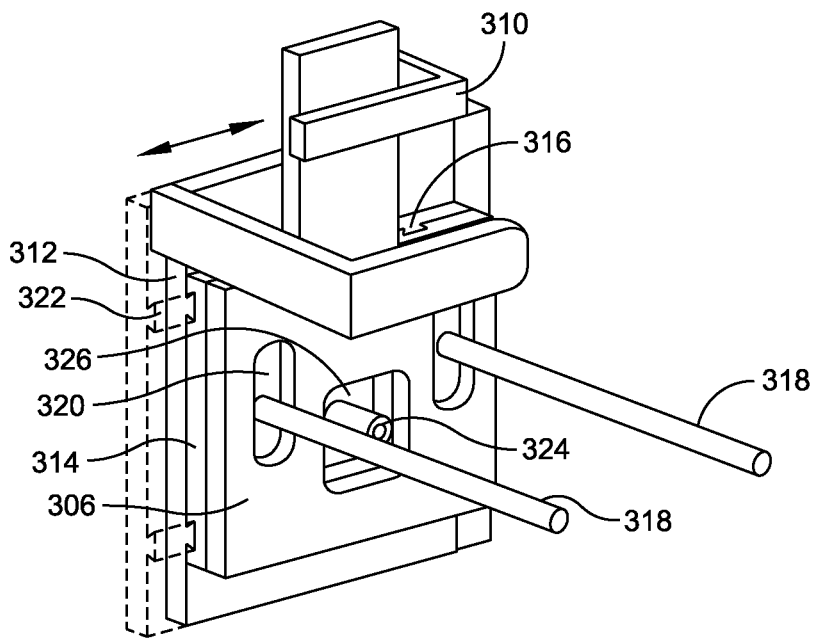

Back plate 312 is coupled to mid-plate 314 by sliding dovetail couplings 322 for side-to-side (i.e., horizontal) movement relative to foot rest 306 as illustrated in FIG. 28B. Back plate 312 also carries a bushing 324, which extends through openings 326 defined by mid-plate 314 and foot rest 306 and terminates at or near the plane of the foot rest 306 against which the bottom of the foot contacts. The center of the bushing 324 coincides with the intersection of the horizontal plane of the rods 318.

Figure 29:
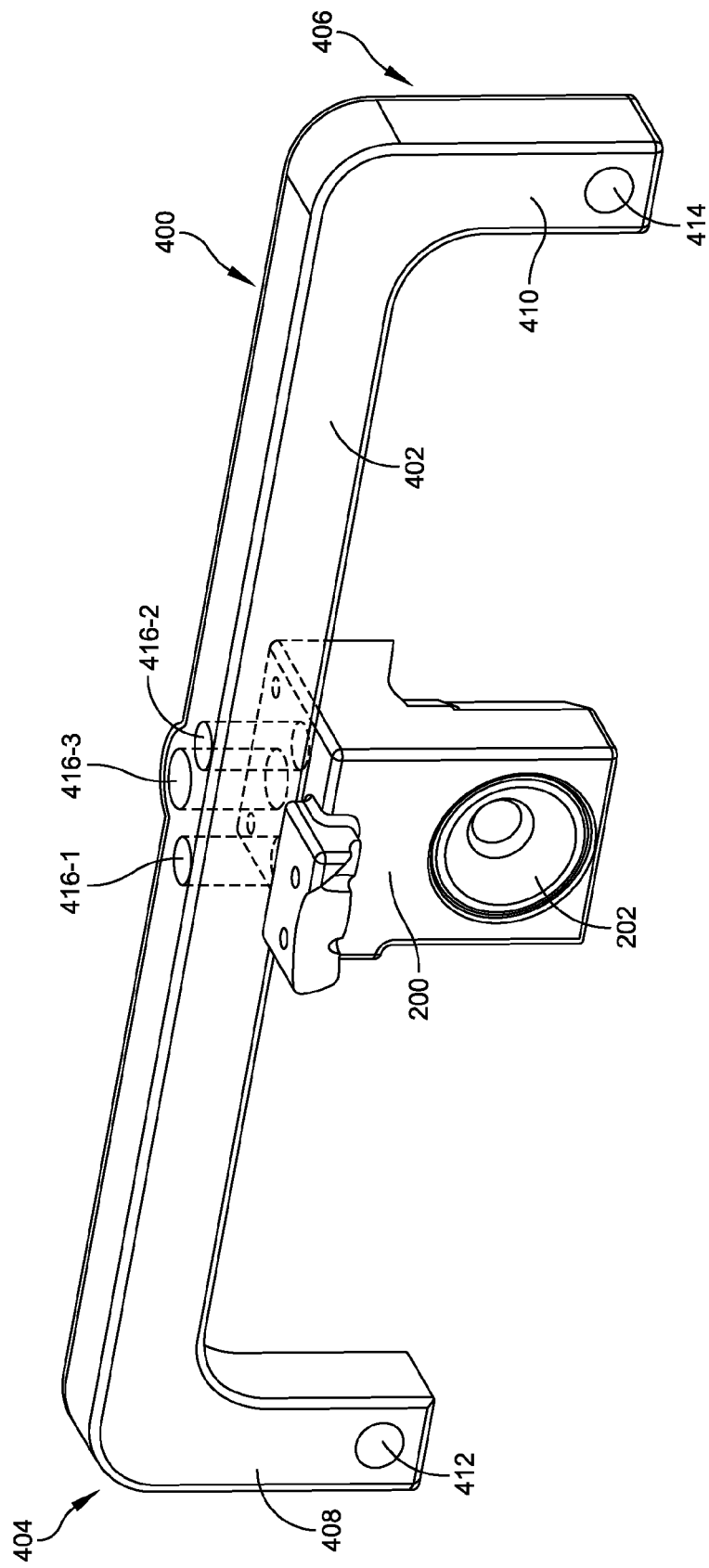
FIG. 29 is a perspective view of one example of an adapter bar for coupling the assemblage of the tibial drill guide mount and tibial drill guide to the alignment tool.

An adapter bar 400 for coupling tibial drill guide mount 200 to alignment tool 300 is illustrated in FIG. 29. Adapter bar 400 includes an elongate body 402 linearly extending from a first end 404 to a second end 406. Each of the ends 404, 406 includes a respective extension 408, 410 that extends from elongate body 402 at an angle. In some embodiments, extensions 408 and 410 orthogonally extend from elongate body 402, although one skilled in the art will understand that extensions 408 and 410 may diverge from elongate body 402 at other angles. In some embodiments, elongate body 402 may not have a linear shape, but may have a curved or arced shape as will be understood by one skilled in the art.

Each extension 408 and 410 defines a respective hole 412, 414 that is sized and configured to slidably receive alignment rods 318 that extend from alignment tool 300. Elongate body 402 defines one or more holes 416-1, 416-2, and 416-3 (collectively referred to as "holes 416") for coupling to adapter bar 400 to tibial drill guide mount 200. In some embodiments, the one or more holes 416 align with one or more holes 216 defined by body 204 of tibial drill guide mount 200 such that a pin or other device for maintaining the alignment and engagement of adapter bar 400 and tibial drill guide mount 200. For example, holes 216-1 and 216-2 of tibial drill guide mount 200 align with holes 416-1 and 416-2 of adapter bar 400, and hole 216-3 of drill guide mount 200 aligns with hole 416-3 of adapter bar 400. Dowel pins 70 (shown in FIG. 25C) may be inserted into holes 216-1 and 416-1 as well as into holes 216-2 and 416-2 to align tibial drill guide mount 200 with adapter bar 400 in both the horizontal and vertical directions (e.g., in the x- and y-directions), and a screw (not shown) may be inserted through hole 416-3 into threaded hole 216-3 to secure tibial drill guide mount 200 to adapter bar at the proper height or depth (e.g., in the z-direction).

Figure 30:
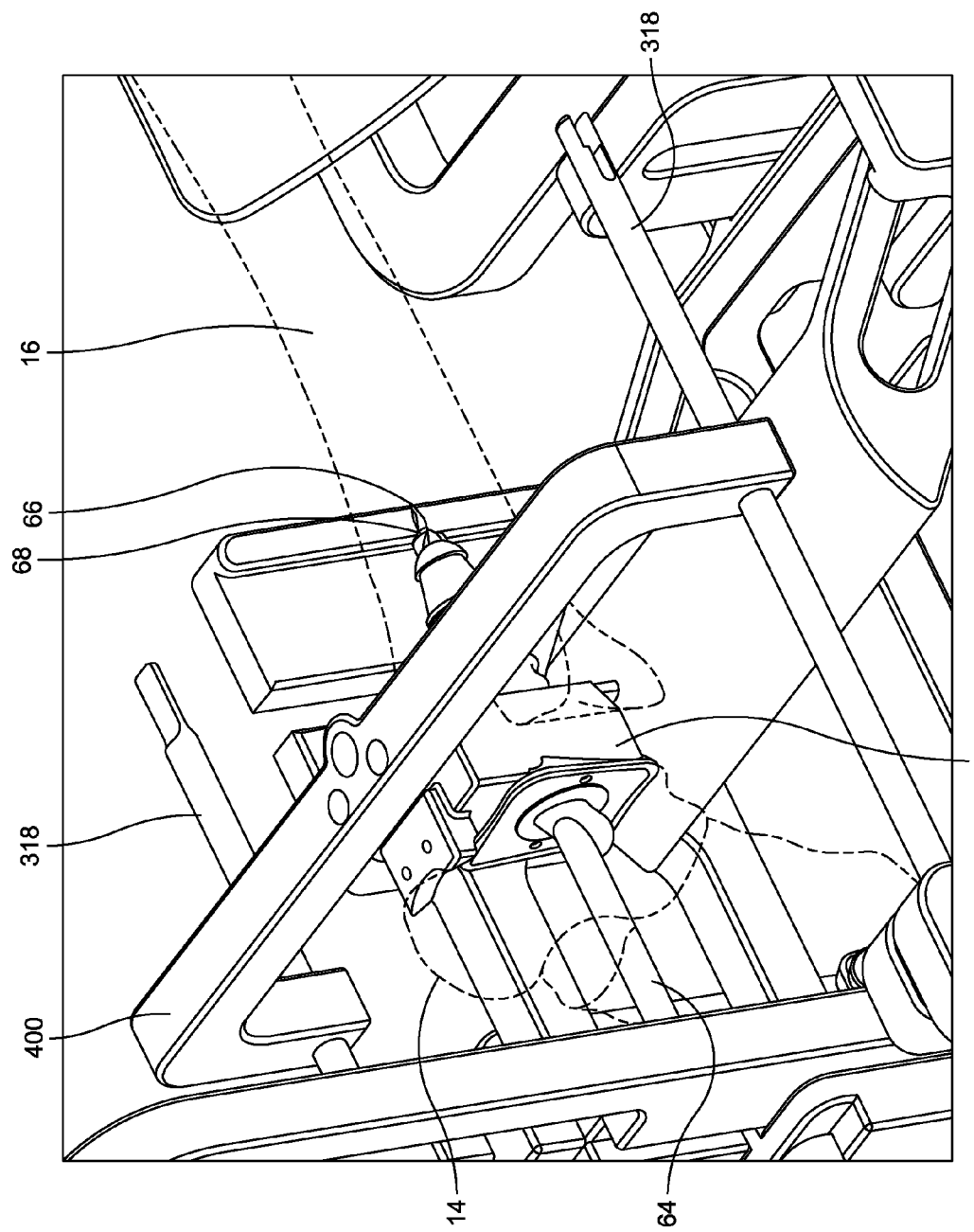
FIG. 30 is a perspective view of the adapter bar coupled to the assemblage of the tibial drill guide mount and tibial drill guide and to the alignment tool.

With tibial drill guide mount 200 and tibial drill guide 202 disposed within the resected ankle space 22, the foot and lower leg are placed in foot rest 306 and leg rest 304 (FIG. 30). The physician estimates the ankle's axis of dorsi-plantar rotation and visually aligns the ankle to the axis of rotation of the alignment tool 300. Foot rest 306 is adjusted to rotate the foot so that the big toe is essentially pointing in a vertical direction with respect to the leg that extends in a horizontal direction. The forefoot and heel are secured to foot rest 306 with clamps 308 and 310. Leg rest 304 is adjusted to the calf so that the tibia 16 is approximately parallel to the floor. The foot and calf are desirably aligned so that the anterior-posterior ("A-P") line of the talus's trochlea is essentially vertical.

Adapter bar 400 is coupled to alignment tool 300 by aligning holes 412 and 414 that are respectively defined by extensions 408 and 410 with alignment rods 318 of alignment tool 300. Adapter bar 400 is then slid along alignment rods 318 until holes 416 of adapter bar align with holes 216 defined by body 204 of tibial drill guide 200 (FIG. 30). As described above, dowel pins 70 are inserted into holes 416-1 and 416-2 of adapter bar 400 and holes 216-1 and 216-2 of tibial drill guide mount 200. With dowels 70 disposed within holes 216-1, 216-2, 416-1, and 416-2, tibial drill guide mount 200 is properly aligned with alignment tool 300 in the medial lateral (e.g., x-direction) and superior-inferior (e.g., y-direction) directions. A screw is inserted through hole 416-3 into threaded hole 216-3, which secures tibial drill guide mount 200 to adapter bar 400 and provides proper alignment in the anterior-posterior direction (e.g., the z-direction).

With the patient's foot disposed within alignment tool 300, bushing 324 on back plate 312 establishes alignment with the mechanical axis of tibia 16 and alignment of rods 318. Thus, after using adapter bar 400 to align tibial drill guide mount 200 with alignment tool 300 as described above, in line drilling of the center of the ankle and tibia for introduction of a bottom foot cannula is made possible without the use of fluoroscopy since aperture 246 of tibial drill guide 202 disposed within tibial drill guide mount 200 is aligned with an axis defined by bushing 324. Such arrangement enables an intramedullary channel to be formed that is substantially collinear with a mechanical axis defined by the tibia.

Various minimally invasive surgical techniques may be used to introduce a bottom foot cannula into the calcaneus 20, talus 14, and tibia 16. In one representative embodiment, bushing 324 is temporarily separated from the back plate 312 (e.g., by unscrewing) to provide access to the bottom of the foot. The physician uses a scalpel to make an initial incision in the bottom of the foot and replaces bushing 324. A cannulated trocar loaded with a k-wire (not shown) can be inserted through bushing 324, into the bottom of the foot, until the calcaneus 20 is contacted and the k-wire is firmly set within the calcaneus 20. The trocar can then be removed, and the k-wire lightly tapped further into the calcaneus 20. In a representative embodiment, the bushing 324 measures 6 mm in diameter, and the cannulated trocar can be 6 mm loaded with a 2.4 mm k-wire. The physician can now operate a cannulated first reamer (e.g., 6 mm) (not shown) over the k-wire up into the calcaneus 20 and talus 14. The first reamer opens an access path for insertion of a bottom foot cannula.

After withdrawing the first reamer and bushing 324, the physician then inserts a bottom foot cannula 64 as shown in FIG. 30. With the bottom foot cannula 64 in place, a second reamer 66 (e.g., 5 mm) can be operated through the cannula 64 to drill approximately another 100 mm through the talus 14 and up into the tibia 16 to establish an intramedullary guide path through the calcaneus 20 and talus 14 leading into the tibia 16 (FIG. 30). As second reamer 66 is advanced towards tibia 16, the tip 68 of reamer 66 is guided by the conical interior surface 248 of tibial drill guide 204, which is aligned with bushing 324 of alignment tool 300.

Once an intramedullary channel through the calcaneus 20, talus 14, and tibia 16 has been established, adapter bar 400 is decoupled from drill guide mount 200 and alignment rods 318. Drill guide mount 200 is removed from resected joint space 22 to expose the resected joint space to the surgeon.

With the resected ankle joint space 22 exposed to the surgeon, an ankle prosthesis is then installed. In one example, the ankle prosthesis includes a stem that may extend from the bottom of the calcaneus up to the top of the talus (i.e., a talo-calcaneal stem), although in some embodiment the stem is completely disposed within the talus (i.e., a talar stem). A convex dome is coupled to the stem and provides an articulating joint surface. A tibial stem may be monolithic or include a plurality of segments that may be coupled together in situ. A tibial platform couples to the tibial stem and either includes or is coupled to a convex joint surface for articulating with the articulating joint surface coupled to the talar/talo-calcaneal stem. Examples of such ankle prosthesis and methods of installing such prosthesis are disclosed in U.S. Pat. No. 7,534,246 issued to Reiley et al., the entirety of which is herein incorporated by reference.

Figure 31:
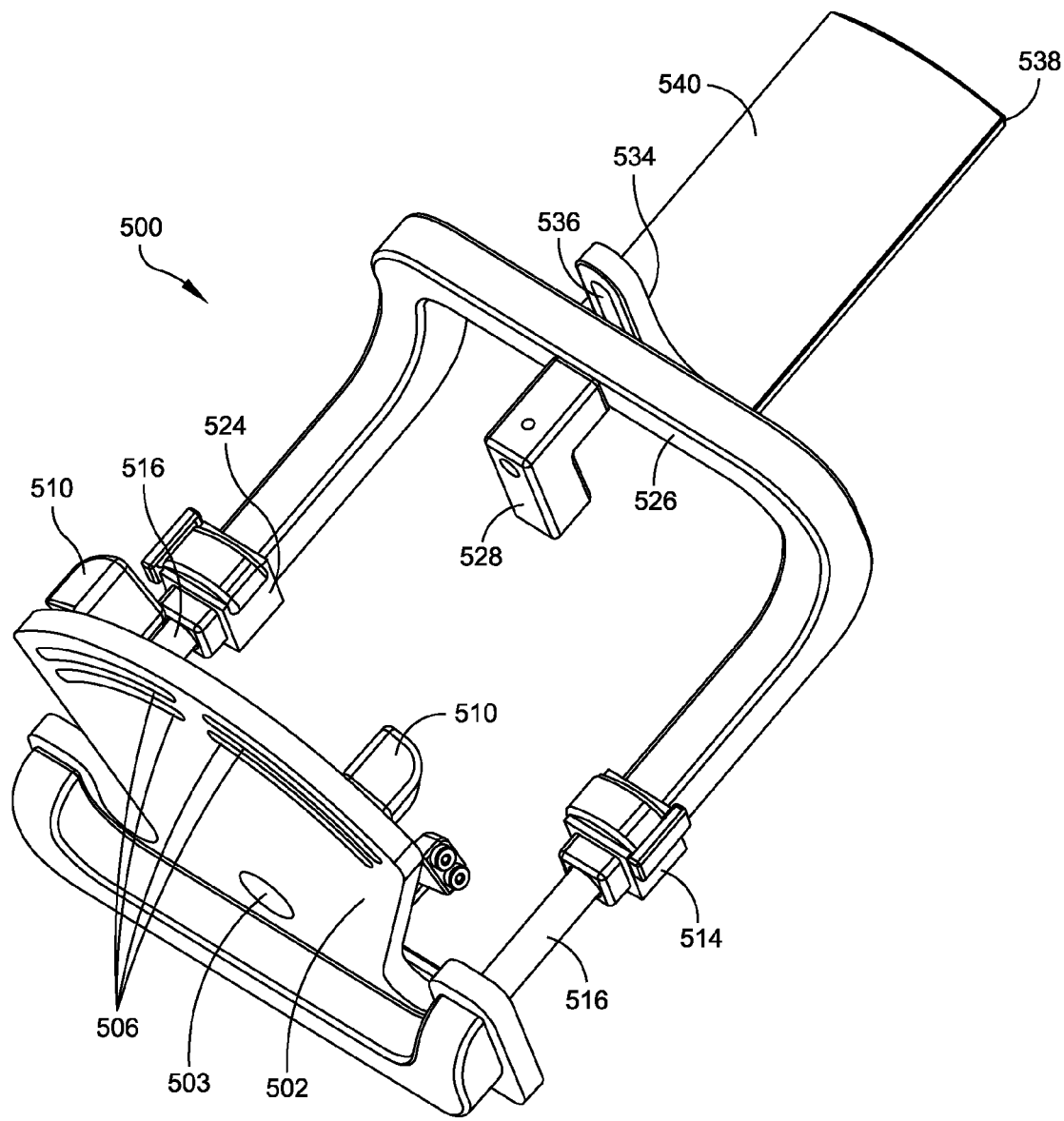
FIG. 31 is a top isometric view of another example of an alignment tool/foot holder assembly for use with a tibial drill guide mount and tibial drill guide.
Figure 32:
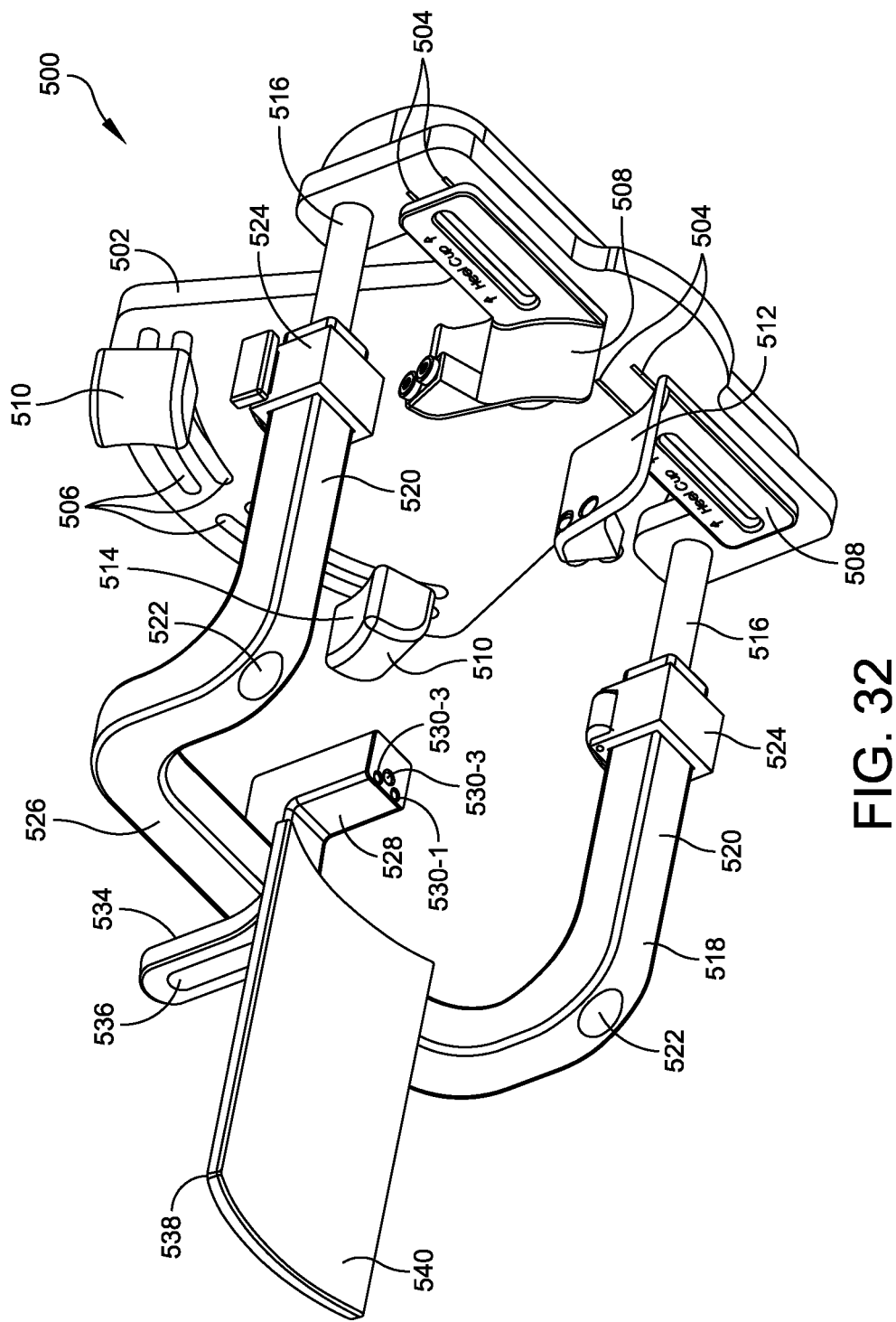
FIG. 32 is a bottom isometric view of the alignment tool/foot holder assembly illustrated in FIG. 31.
Figure 33:
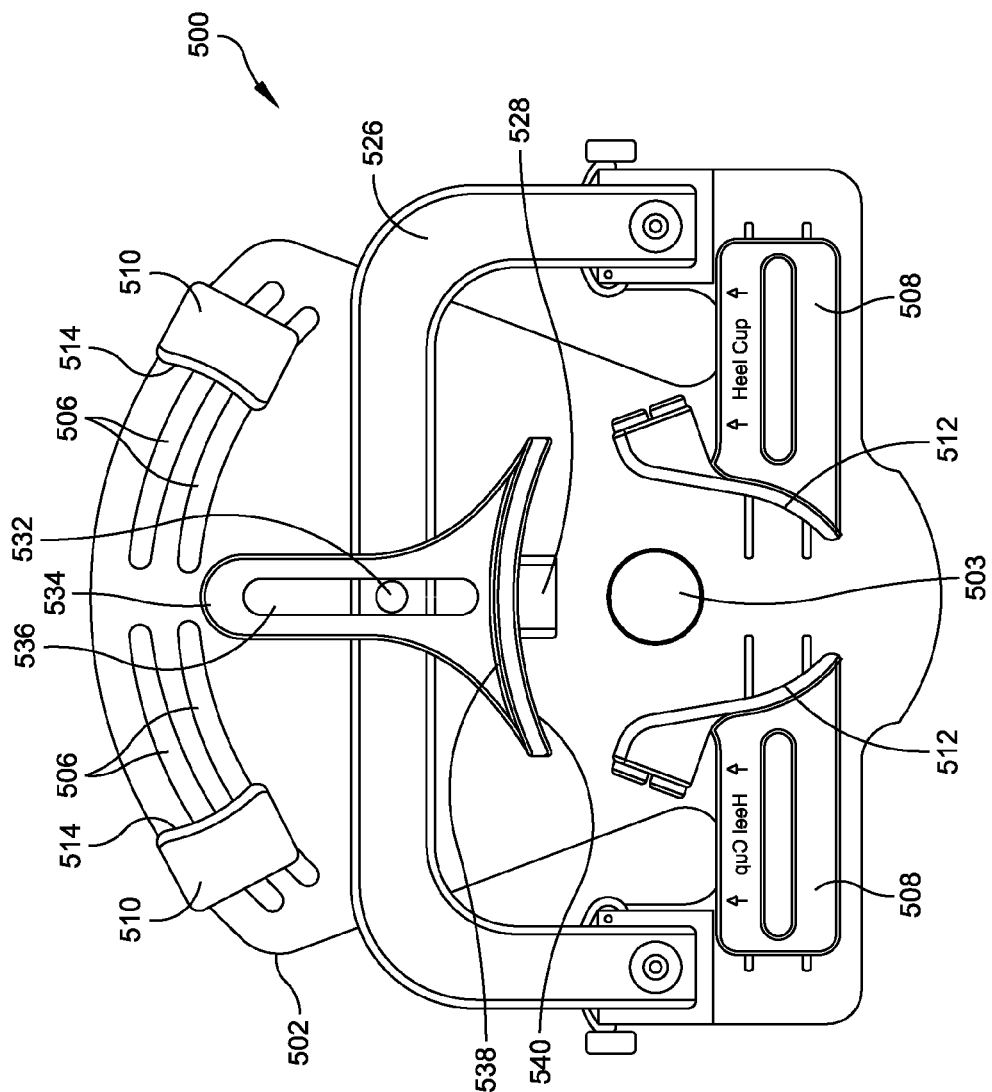
FIG. 33 is an elevational front view of the alignment tool/foot holder assembly illustrated in FIG. 31.

The disclosed tibial drill guide mount 200 and drill guide 202 may be used with a variety of alternative alignment tools. For example, FIGS. 31-34 illustrate another example of an alignment tool in the form of a foot holder assembly 500 to which tibial drill guide mount 200 may be directly coupled. As shown in FIGS. 31 and 32, foot holder assembly 500 includes a base plate 502 defining a plurality of slots 504 and 506 and an aperture 503.

Slots 504 are sized and configured to slidably receive a pair of heel clamps 508, and slots 506 are sized and configured to slidably receive a pair of forefoot clamps or guides 510. Heel clamps 508 and forefoot clamps 510 cooperate to maintain a foot of a patient in a desired position with respect to base plate 502 by utilizing a locking mechanism such as, for example, a set screw or other locking device, to fix the position of heel clamps 508 and forefoot clamps 510 to base plate 502. The respective foot engaging surfaces 512 and 514 of heel clamps 508 and forefoot clamps 510 may have a shape that complements the medial and lateral shape of a human foot.

Figure 34:
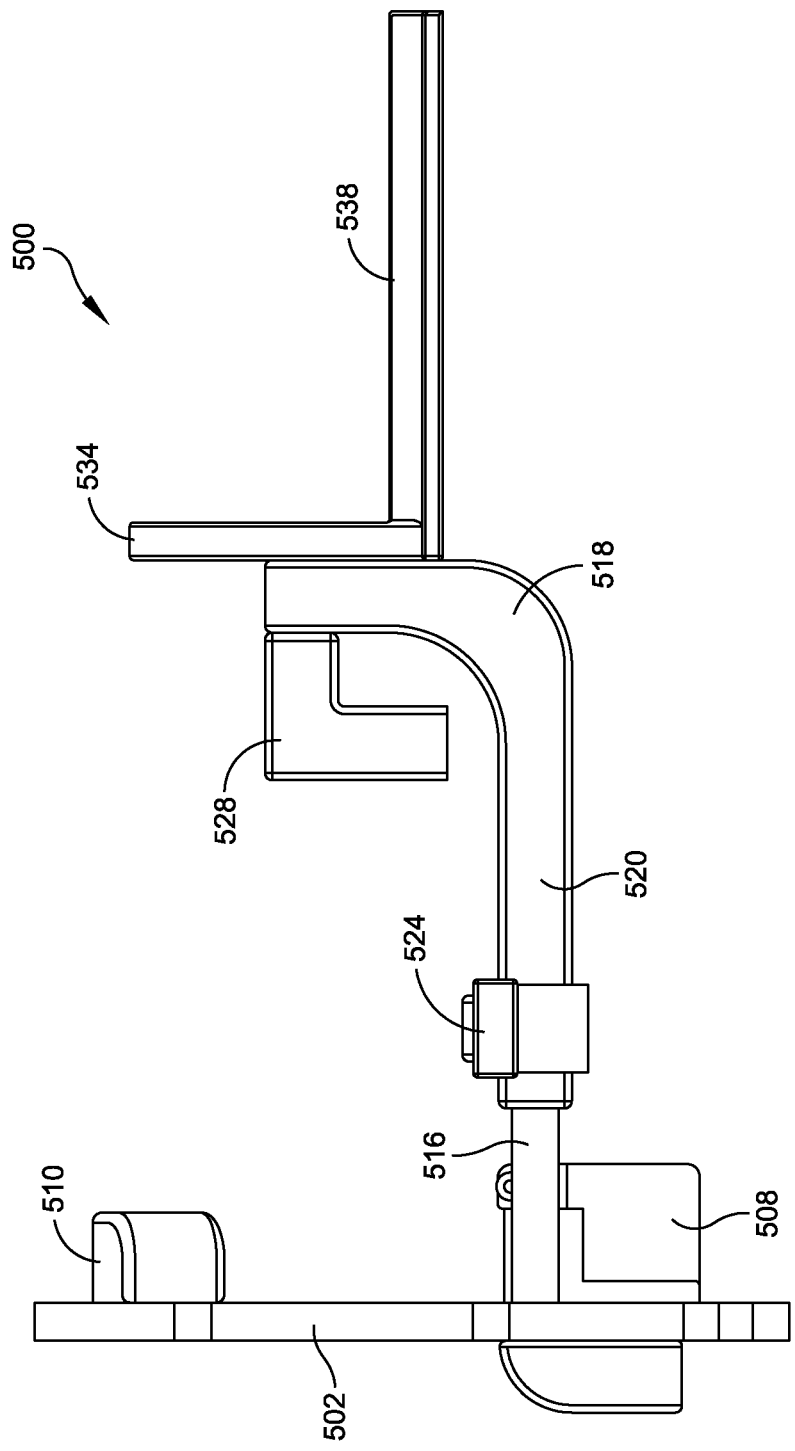
FIG. 34 is an elevational side view of the alignment tool/foot holder assembly illustrated in FIG. 31.

Extending from base plate 502 are a pair of alignment rods 516 that are arranged on base plate 502 such that one alignment rod is disposed on a medial side of a patient's foot and the other alignment rod is disposed on a lateral side of a patient's foot. A coupling bar 518 is sized and configured to slidably engage alignment rods 516 as best seen in FIGS. 32 and 34. Coupling bar 518 includes a pair of spaced apart legs 520 that define channels 522 (FIG. 32) in which alignment rods 516 are slidably received. One or both of legs 520 include a clamp or other locking mechanism 524 for increasing the friction between coupling bar 518 and alignment rods 516 in order to releasably lock coupling bar 518 at a certain position along the length of alignment rods 516.

Medial-lateral cross bar 526 couples together legs 520 of coupling bar 518. Extending from medial-lateral cross bar 526 is mount coupling member 528. Mount coupling member 528 includes one or more holes 530-1, 530-2, and 530-3 (collectively referred to as "holes 530") that are sized and configured to align with holes 216 defined by tibial drill guide mount 200.

A peg 532 (FIG. 33) extends from medial-lateral cross bar 526 for coupling shin engaging member 534 via slot 536 defined by shin engaging member 534. Shin engaging member 534 includes a shelf 538 having a concave surface 540 for abutting a shin of a patient. A nut or other locking mechanism (not shown) for engaging peg 532, which may be threaded, may be used to fix the position of shelf 538 relative to medial-lateral cross bar 526.

The use of foot holder assembly 500 in connection with the assemblage of tibial drill guide mount 200 and tibial drill guide 202 is similar to the use of alignment tool 300 described above. For example, once the assembly of tibial drill guide mount 200 and tibial drill guide 202 are disposed within resected joint space 22, the heel of the patient's foot is placed between heel clamps 508 and the patient's forefoot is placed between forefoot clamps 510. The locking mechanisms of heel and forefoot clamps 508 and 510 may be engaged to initially set positions of heel and forefoot clamps 508 and 510 relative to base plate 502.

Holes 530 of coupling member 528 are aligned with holes 216 defined by tibial drill guide mount 200 by sliding legs 520 of coupling bar 518 along alignment rods 516. Dowel pins 70 and/or a threaded screw (not shown) may be used to couple holes 530 of coupling member 528 to holes 216 of tibial drill guide mount 200. The surgeon may check to ensure that the patient's foot is firmly against base plate 502 and then engage clamps 524 such that coupling bar 518 is fixed to alignment rods 516.

Shin engaging member 534 is adjusted until concave surface 540 contacts the patient's shin. The adjustment of shin engaging member 534 is guided by the engagement between slot 536 and peg 532. With shin engaging member 534 in the desired position, the nut or other locking mechanism (not shown) locks shin engagement member 534 in place. The surgeon may make final adjustments to the heel and forefoot clamps 508 and 510 and then create the intramedullary channel as described above.

Figure 35:
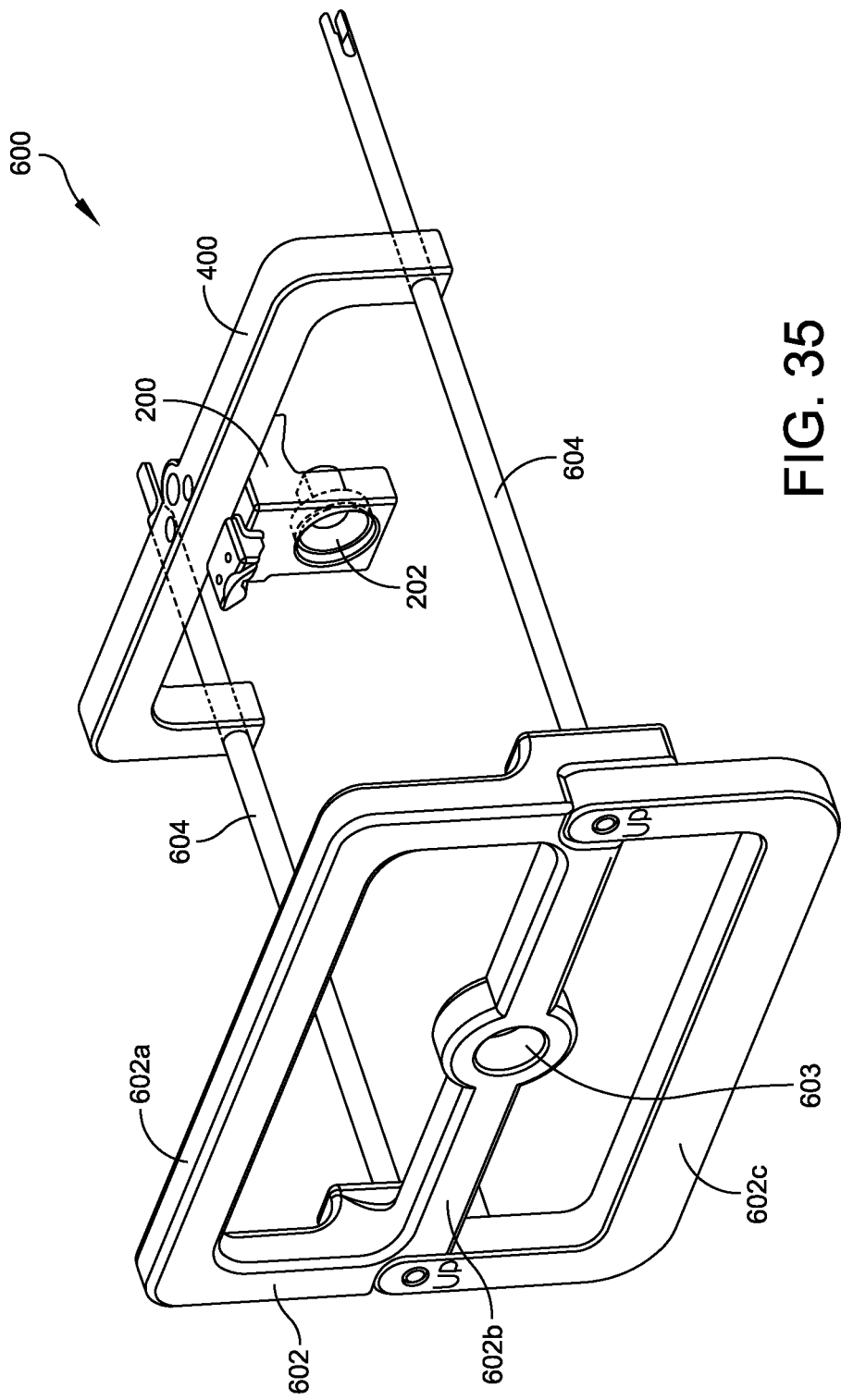
FIG. 35 is a top isometric view of another example of an alignment tool/foot holder assembly for use with the tibial drill guide mount and tibial drill guide.
Figure 36:
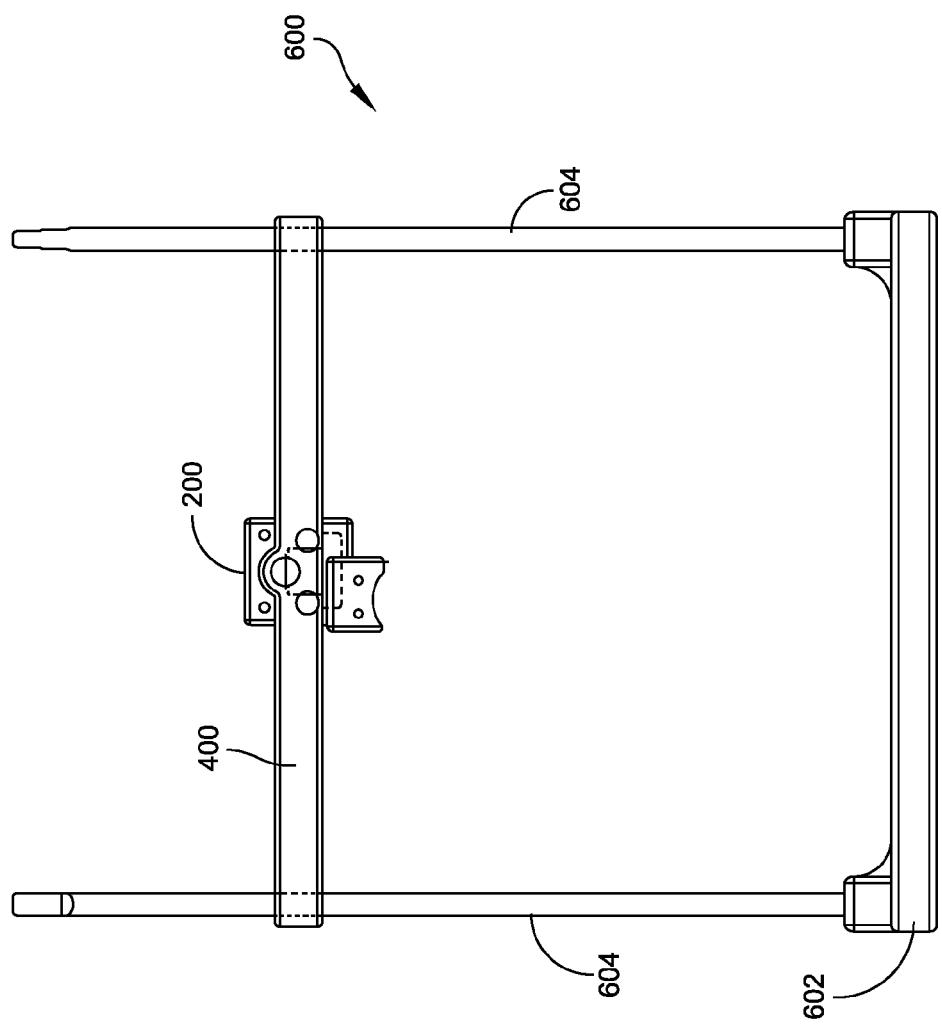
FIG. 36 is a top elevational view of the alignment tool/foot holder assembly illustrated in FIG. 35.
Figure 37:
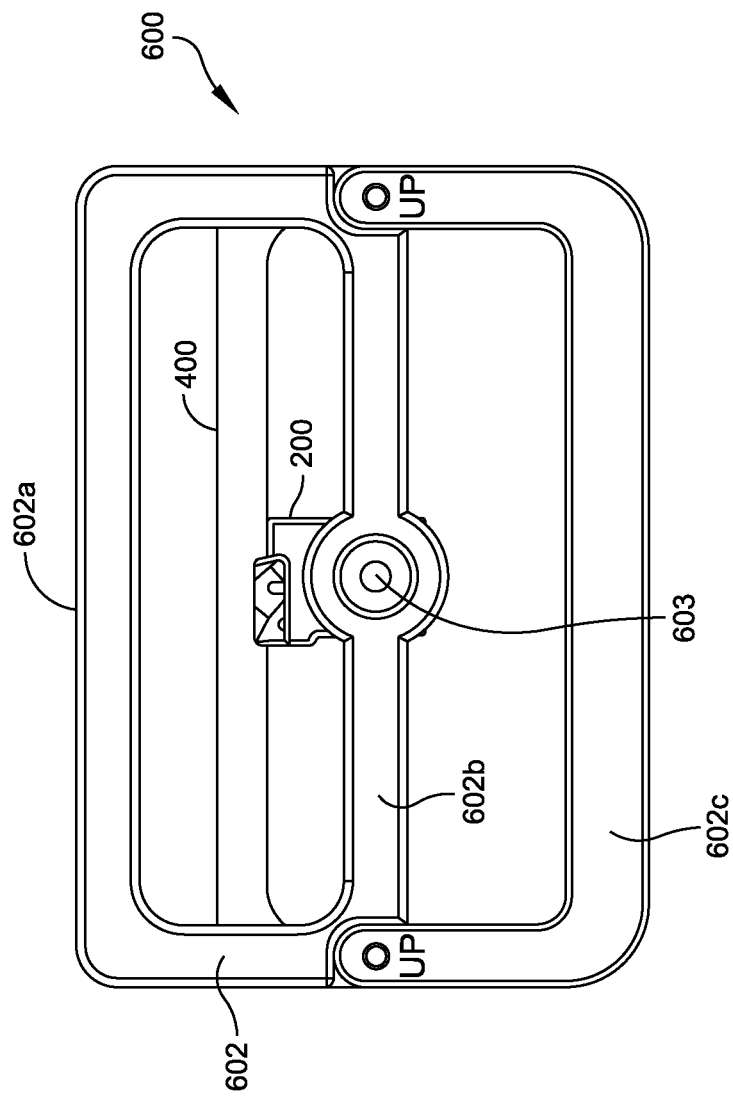
FIG. 37 is an elevational front view of the alignment tool/foot holder assembly illustrated in FIG. 35.
Figure 38:
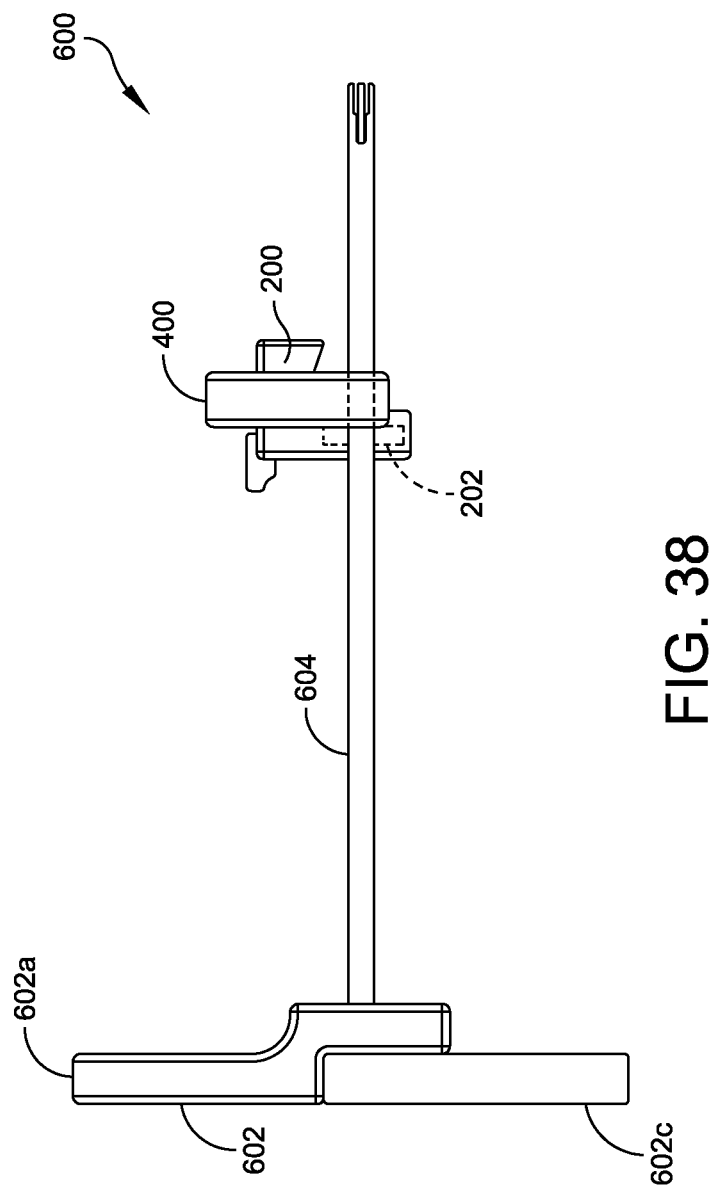
FIG. 38 is an elevational side view of the alignment tool/foot holder assembly illustrated in FIG. 35.
Figure 39:
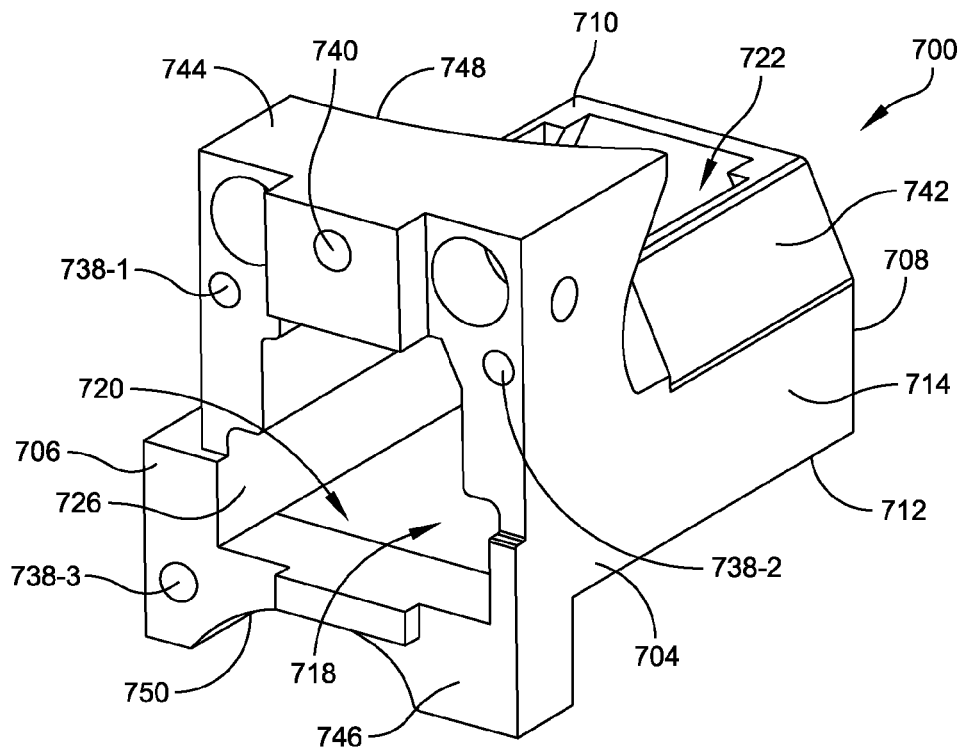
FIG. 39 is a perspective view of another example of a tibial cutting guide mount.
Figure 40:
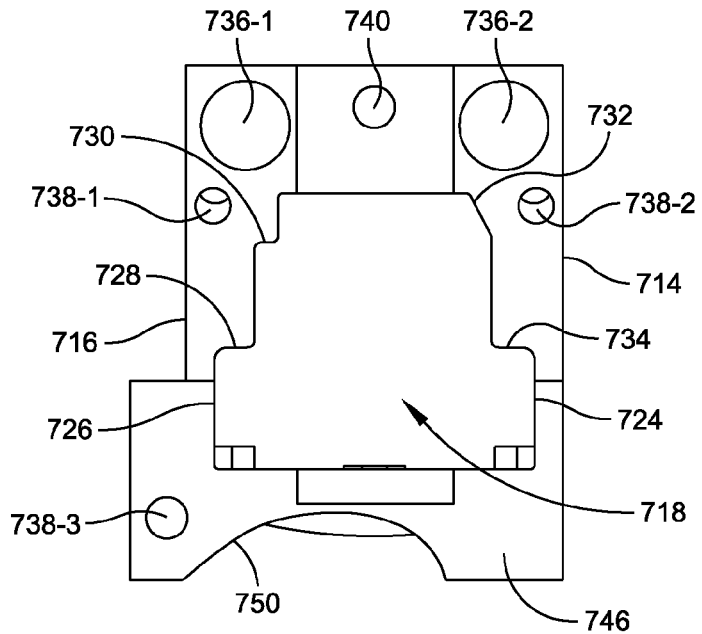
FIG. 40 is a front side elevational view of the tibial cutting guide mount illustrated in FIG. 39.
Figure 41:
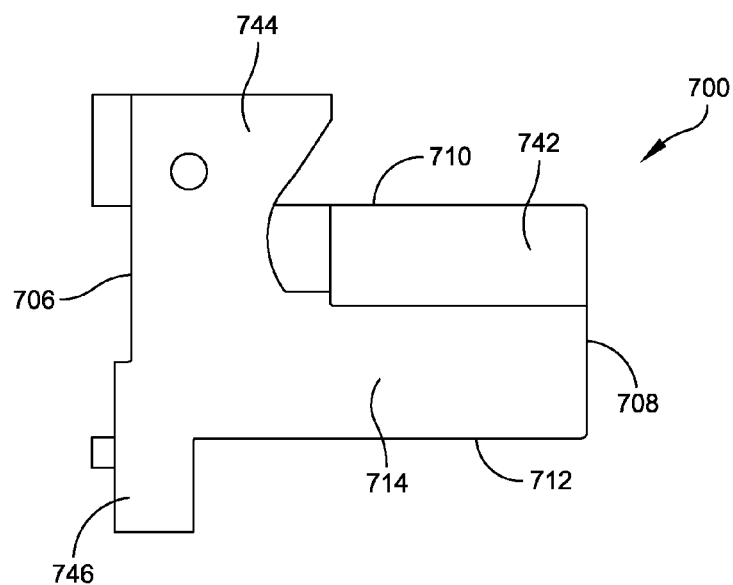
FIG. 41 is a side elevational view of the tibial cutting guide mount illustrated in FIG. 39.
Figures 42, 43:
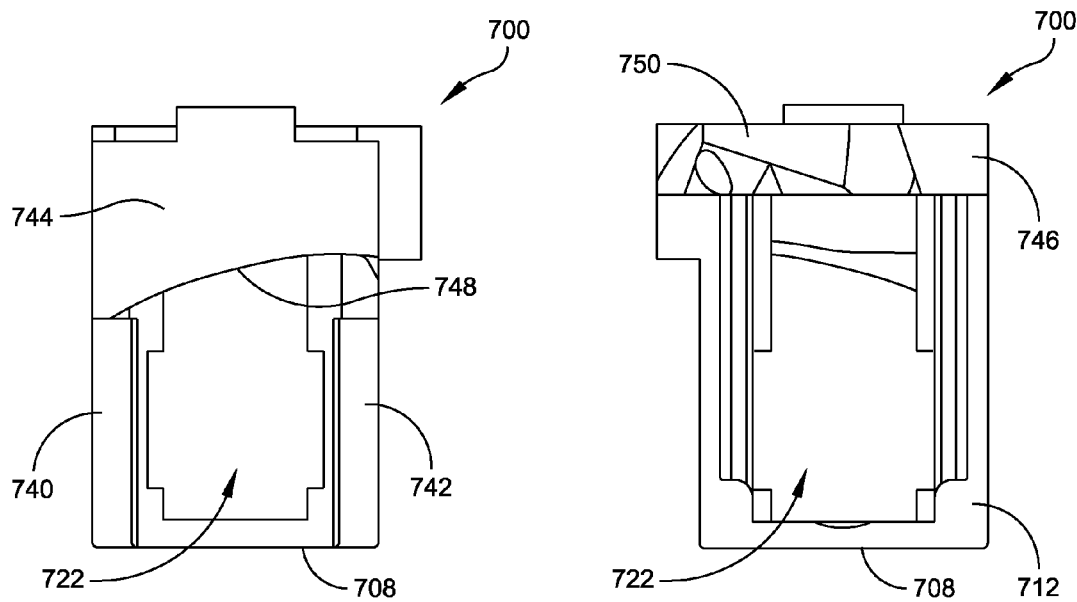
FIG. 42 is a top side view of the tibial cutting guide mount illustrated in FIG. 39.
FIG. 43 is a bottom side view of the tibial cutting guide mount illustrated in FIG. 39.

Another example of an alignment tool 600 for use with tibial drill guide mount 200 and tibial drill guide 202 is illustrated in FIGS. 35-38. As shown in FIG. 35, alignment tool 600 includes a base plate 602 comprising a plurality of bars 602a, 602b, and 602c. Although three bars 602a, 602b, and 602c are illustrated, one skilled in the art will understand that fewer or more bars may be implemented. Bar 602b defines a hole 603 sized and configured to receive a surgical tool, such as, for example, a cannulated drill. Additional elements including, but not limited to, heel clamps and/or forefoot clamps (not shown) may be coupled to the bars 602a, 602b, and 602c of base plate 602 for aiding in the positioning of a patient's foot with respect to hole 603.

Extending from base plate 602 is a pair of spaced apart alignment rods 604. One of alignment rods 604 may be disposed on a medial side of a patient's leg, and the other alignment rod 604 disposed on a lateral side of the patient's leg. Alignment rods 604, like alignment rods 318 of alignment tool 300, may be slidably receiving within holes 412, 414 of adapter bar 400.

The use of alignment tool 600 in connection with the assemblage of tibial drill guide mount 200 and tibial drill guide 202 and the adapter bar 400 is similar to the use of alignment tool 300 described above. For example, once the assembly of tibial drill guide mount 200 and tibial drill guide 202 are disposed within resected joint space 22, adapter bar 400 is coupled to alignment tool 600 by aligning holes 412 and 414 that are respectively defined by extensions 408 and 410 with alignment rods 604 of alignment tool 600. Adapter bar 400 is slid along alignment rods 604 until holes 416 of adapter bar align with holes 216 defined by body 204 of tibial drill guide 200. As described above, dowel pins are inserted into holes 416-1 and 416-2 of adapter bar 400 and 216-1 and 216-2 of tibial drill guide mount 200. With dowels disposed within holes 216-1, 216-2, 416-1, and 416-2, tibial drill guide mount 200 is properly aligned with alignment tool 600 in the medial lateral (e.g., x-direction) and superior-inferior (e.g., y-direction) directions. A screw is inserted through hole 416-3 into threaded hole 216-3, which secures tibial drill guide mount 200 to adapter bar 400 and provides proper alignment in the anterior-posterior direction (e.g., the z-direction). The surgeon may make final adjustments to the heel and forefoot clamps 508 and 510 and then create the intramedullary channel as described above.

FIGS. 39-63 illustrate another embodiment of a system for performing a surgical procedure. Specifically, FIGS. 39-43 illustrate a tibial drill guide mount 700 sized and configured to receive the tibial drill guide cartridge 702 illustrated in FIGS. 44-47. Tibial drill guide mount 700 may also receive other drill guide cartridges for use during other stages of the surgical procedures. Like tibial drill guide mount 200, tibial drill guide 700 may be fabricated from a resilient polymer material of the type that is suitable for use in connection with stereo lithography, selective laser sintering, or the like manufacturing equipment, e.g., a polyamide powder repaid prototype material is suitable for use in connection with selective laser sintering.

As shown in FIG. 39-43, tibial drill guide mount 700 has a somewhat rectangular body 704 having a front side 706, a rear side 708, top side 710, bottom side 712, and a pair of opposed sides 714 and 716. Front side 706 defines a recess 718 sized and configured to slidably receive tibial drill guide 702 therein. Recess 718 communicates with a recess 720 (FIGS. 39 and 43) defined by bottom side 712 and a recess 722 (FIGS. 39, 42, and 43) defined by top side 710 such that body 704 is substantially hollow.

The respective inner surfaces 724, 726 of sides 714, 716 have different geometries that correspond with the cross-sectional geometry of tibial drill guide cartridge 702 to ensure that tibial drill guide cartridge 702 is properly inserted into recess 718. In the embodiment illustrated in FIGS. 39-43, side 716 includes first and second ledges 728, 730 that inwardly extend into recess 718, and side 714 has an inwardly tapered upper region 732 and an inwardly extending ledge 734. One skilled in the art will understand that sides 714, 716 may include other features for ensuring proper insertion of tibial drill cartridge 702 into recess 718. In some embodiments, sides 714, 716 may have the identical geometry and tibial drill guide cartridge may be reversibly inserted into recess 718.

Front side 706 defines one or more dowel holes 736-1, 736-2 (collectively referred to as "dowel holes 736") sized and configured to receive a dowel pin 70 therein. One or more through holes 738-1, 738-2, 738-3 (collectively referred to as "through holes 738") extend through front side 706, which also defines a blind hole 740. Through holes 738 are sized and configured to receive k-wires for pinning tibial drill guide mount to a patient's bone as described below.

Top side 710 of tibial drill guide mount 700 includes a pair of chamfers 742 that are sized and configured to be mate against and reference the resected surfaces of the lower tibia 16a (FIG. 8). Tibial drill guide mount 700 also includes a tibial engagement structure 744 and a talar engagement structure 746. Tibial engagement structure 744 extends from top side 710 and includes a substantially conformal engagement surface 748. Talar engagement structure 746 extends from bottom side 712 and also includes a substantially conformal engagement surface 750.

Figure 44:
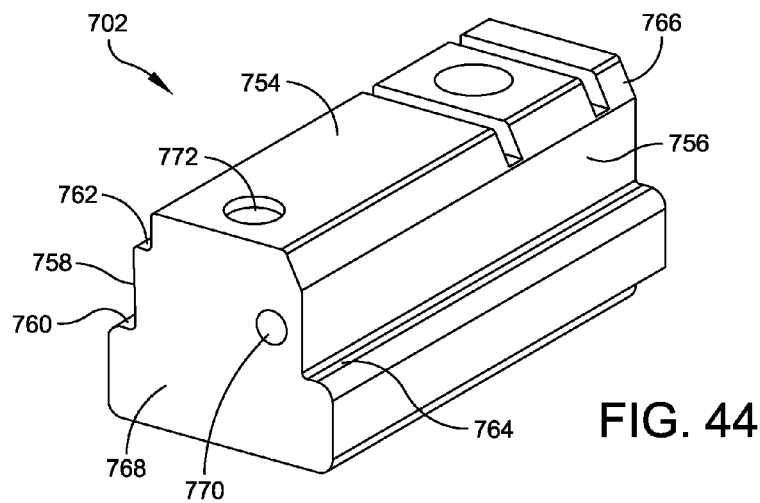
FIG. 44 is a perspective view of a tibial drill guide cartridge for use with the tibial drill guide mount illustrated in FIG. 39.
Figure 45:
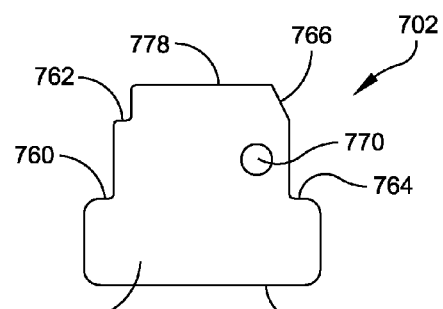
FIG. 45 is a front end view of the tibial drill guide cartridge illustrated in FIG. 44.
Figure 46:
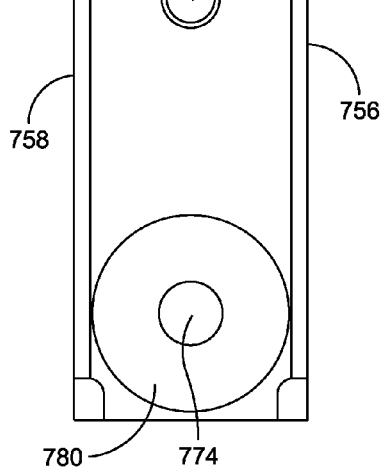
FIG. 46 is a bottom side plan view of the tibial drill guide cartridge illustrated in FIG. 44.

Tibial drill guide cartridge 702 has a substantially rectangular elongate body 754 that may be formed from a more substantial material than tibial drill guide mount 700 such as, for example, metals, ceramics, or the like. As best seen in FIGS. 44 and 45, the geometry of sides 756, 758 is respectively complementary to the sides 714, 716 of tibial drill guide mount 700. For example, side 758 includes ledges 760 and 762 that respectively correspond to ledges 728 and 730, and side 756 includes a ledge 764 and an angled section 766, which respectively correspond to ledge 734 and upper region 732 of tibial drill guide mount 700.

Figure 47:
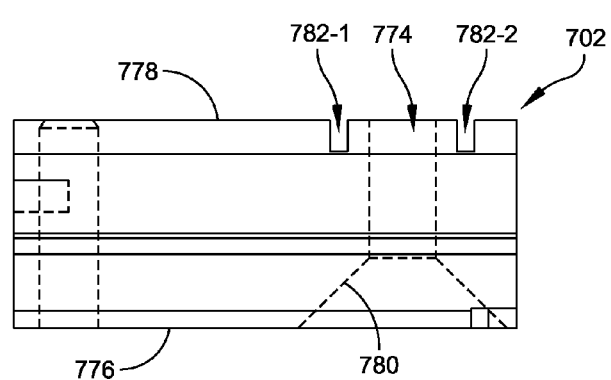
FIG. 47 is a side view of the tibial drill guide cartridge illustrated in FIG. 44.

Front side 768 of tibial drill guide cartridge 700 defines a blind hole 770, which may be threaded for reasons described below. Tibial drill guide cartridge 702 defines a pair of holes 772 and 774 that extend from bottom surface 776 to top surface 778. Hole 772 may be a reamed hole that is sized and configured to receive a ball detent therein, and hole 774 has an internal surface 780 that tapers from a larger diameter at bottom surface 776 to a smaller surface that is sized and configured to receive a surgical tool, such as a drill and/or reamer. Top surface 778 defines a pair of parallel slots 782-1, 782-2 (collectively referred to as "slots 782") that extend from side 756 to side 758. As best seen in FIGS. 44 and 47, slots 782 are disposed equidistant from a central axis defined by hole 774 to provide a visual key for a physician that wants check the alignment of hole 774 with a mechanical axis of a patient's tibia using fluoroscopy.

Figure 48:
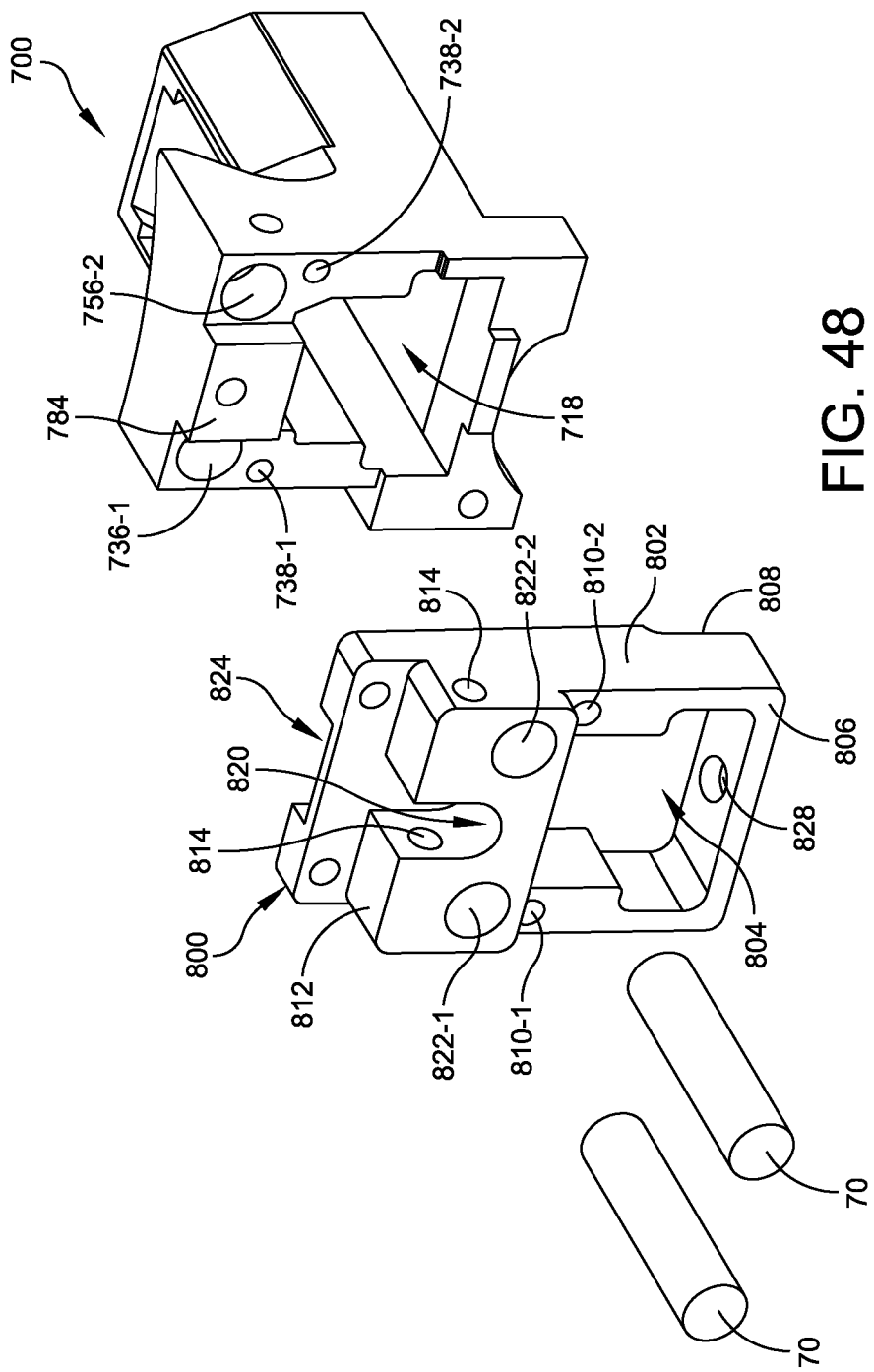
FIG. 48 is an exploded perspective view of a mounting plate and dowel pins configured to for use with the tibial drill guide mount illustrated in FIG. 39.

As illustrated in FIG. 48, a mounting plate 800 has a substantially rectangular body 802 that is fabricated from a material including, but not limited to, metals, ceramics, or the like. Body 802 defines an aperture 804 the extends from front side 806 to back side 808 and has a similar geometry of recess 718 of tibial drill guide mount 700 such that tibial drill guide cartridge 702 may be received therein. Body 802 also defines a pair of through holes 810-1, 810-2 (collectively referred to as "holes 810") that are arranged on body 802 such that they correspond to holes 738 of tibial drill guide mount 700 and are sized and configured to receive a k-wire or pin therein.

A mounting base 812 extends from front side 806 of mounting plate 800 and defines a hole 814 that extends from a first side 816 to a second side 818. Mounting base 812 defines a notch 820 and one or more dowel pin holes 822-1, 822-2 (collectively referred to as "holes 822") that are aligned with holes 736 of tibial drill guide mount 700. Notch 820 bisects hole 814. Mounting base 812 may also define one or more recesses 824 that correspond to one or more protrusions 784 that extends from front side 706 of tibial drill guide mount 700. Recesses 824 and protrusions 784 cooperate to ensure that mounting base 812 and tibial drill guide mount 700 are properly aligned. One skilled in the art will understand that other geometric features may be implemented to ensure proper alignment between mounting base 812 and tibial drill guide mount 700.

Figure 49:
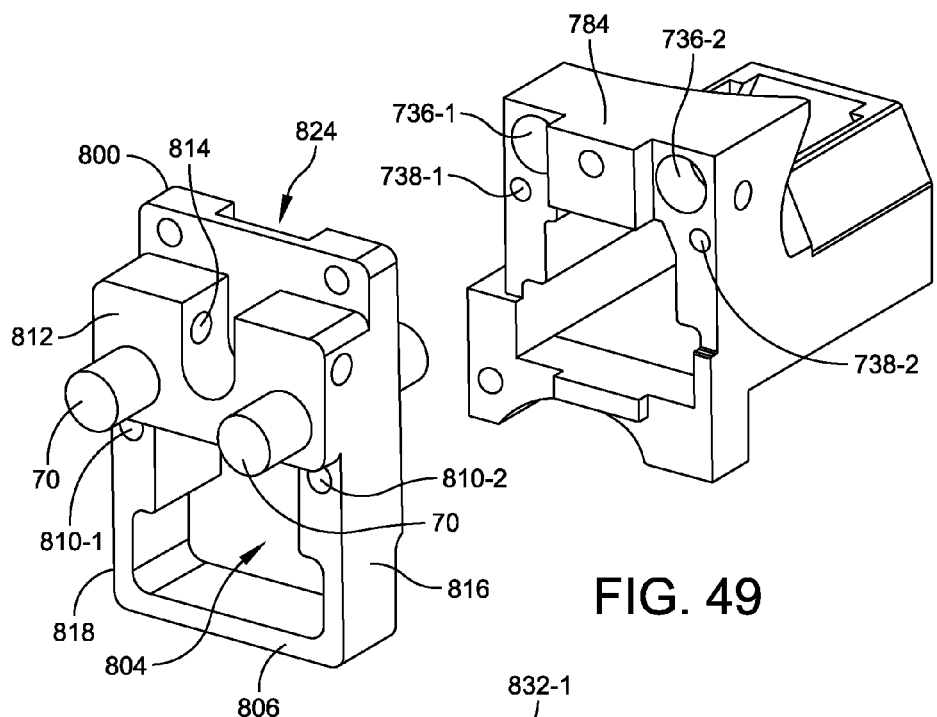
FIG. 49 is a partially exploded perspective view of a mounting plate and dowel pins configured to for use with the tibial drill guide mount illustrated in FIG. 39.
Figure 50:
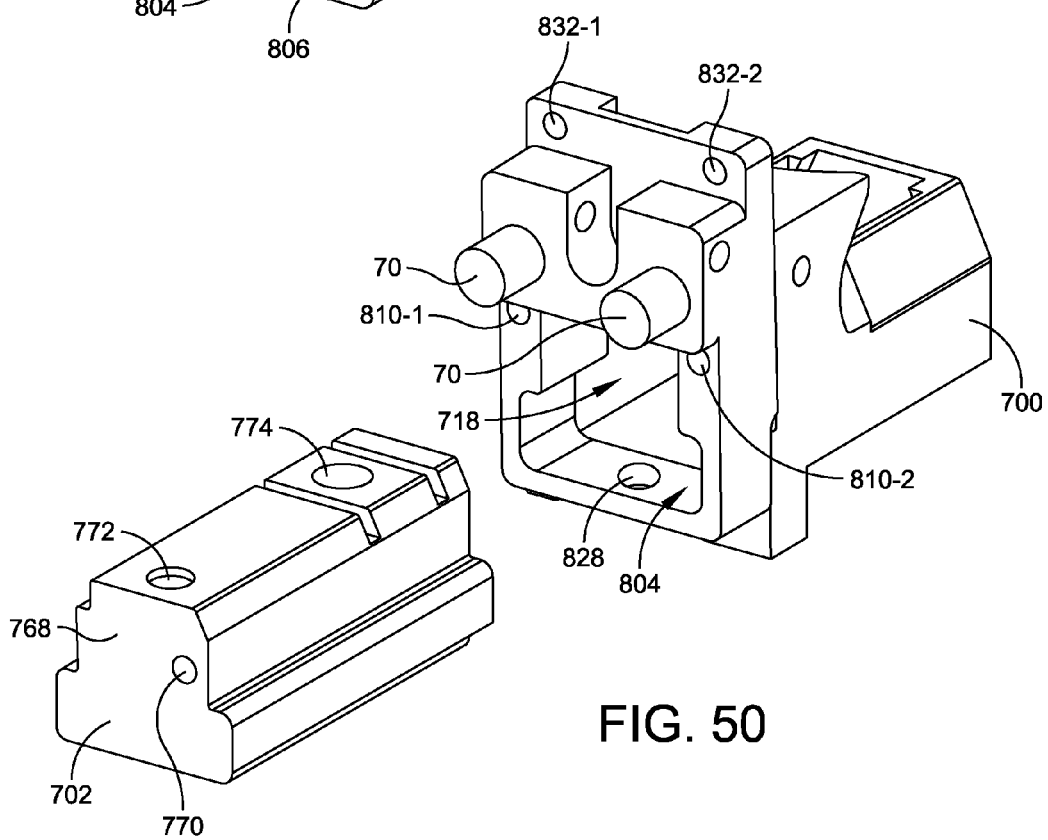
FIG. 50 is a partially exploded perspective view of a mounting plate, dowel pins, and tibial drill guide mount configured to receive a tibial drill guide cartridge in accordance with FIG. 44.
Figure 51:
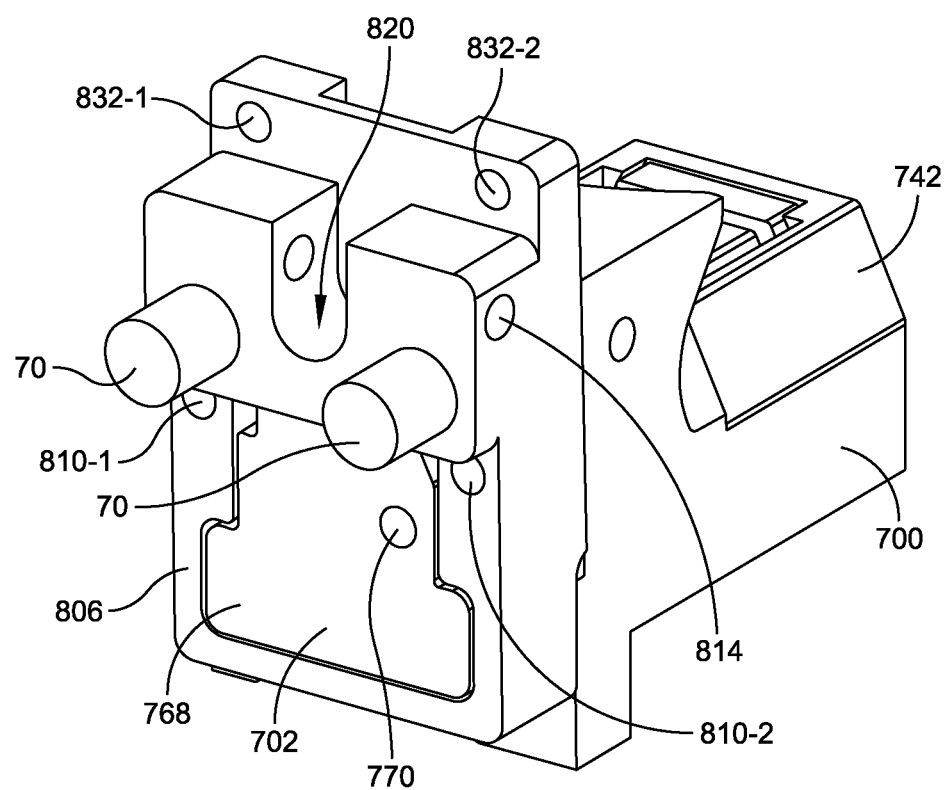
FIG. 51 is a perspective view of the tibial drill guide mount, tibial drill guide cartridge, dowel pins, and mounting plate assembled together.
Figure 52:
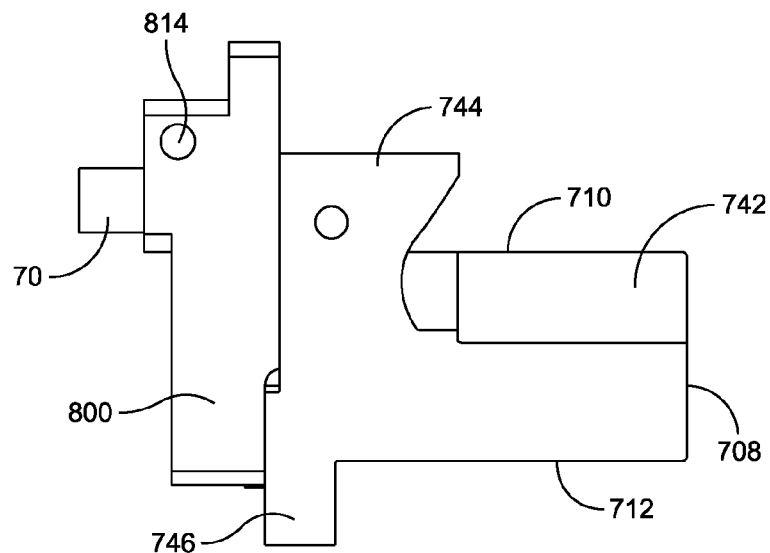
FIG. 52 is a side view of the assembly illustrated in FIG. 51.
Figure 53:
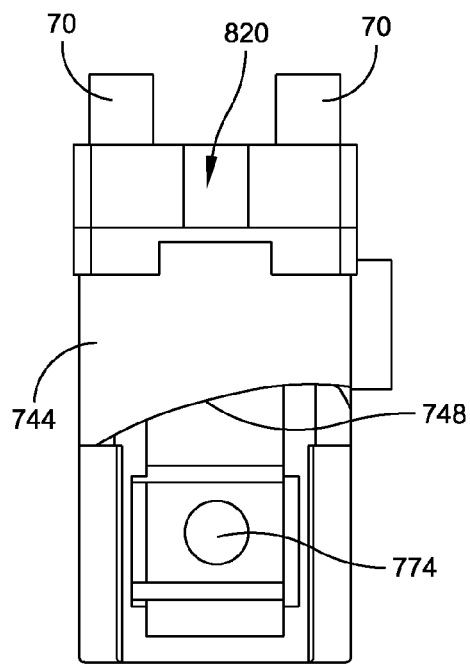
FIG. 53 is a top side plan view of the assembly illustrated in FIG. 51.
Figure 54:
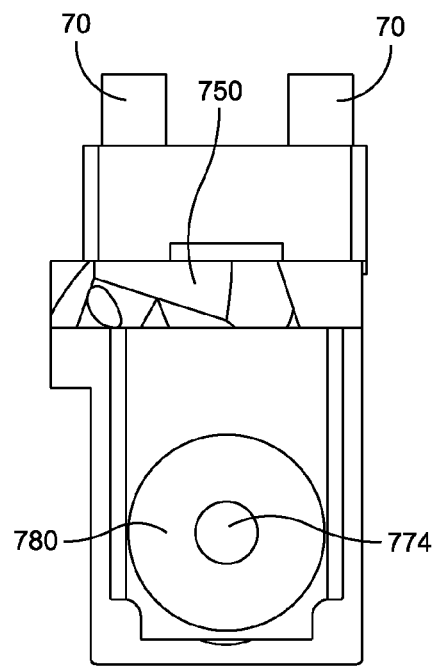
FIG. 54 is a bottom side plan view of the assembly illustrated in FIG. 51.

As illustrated in FIGS. 49-54, mounting plate 800 may be coupled to tibial drill guide mount 700 using dowel pins 70, which are received through holes 822 and 734. Tibial drill guide cartridge 702 is received through aperture 804 and recess 718 as best seen in FIG. 51. FIGS. 53 and 54 illustrate that when tibial drill guide cartridge 702 is properly inserted into the assemblage of tibial drill guide mount 700 and mounting plate 800, hole 772 aligns with hole 828 defined by mounting plate 800, which may include a ball detent (not shown) disposed therein. Consequently, the ball detent is received within hole 772 to retain tibial drill guide cartridge 702 disposed within aperture 804 and recess 718 such that hole 774 is disposed within recesses 754 and 756. A screw or other threaded object (not shown) can be inserted into threaded hole 770 and then pulled to remove tibial drill guide cartridge 702 from aperture 804 and recess 718 as illustrated in FIGS. 53 and 54.

Tibial drill guide mount 700, tibial drill guide 702, and mounting plate 800 may be used in connection with alignment tool 300, adapter bar 400, foot holder assembly 500, and alignment tool 600 as described above. Additionally, tibial drill guide mount 700, tibial drill guide 702, and mounting plate 800 may also be used in conjunction with foot holder assembly 900 illustrated in FIGS. 55-60 as can tibial drill guide mount 200 and tibial drill guide 202.

Figure 55:
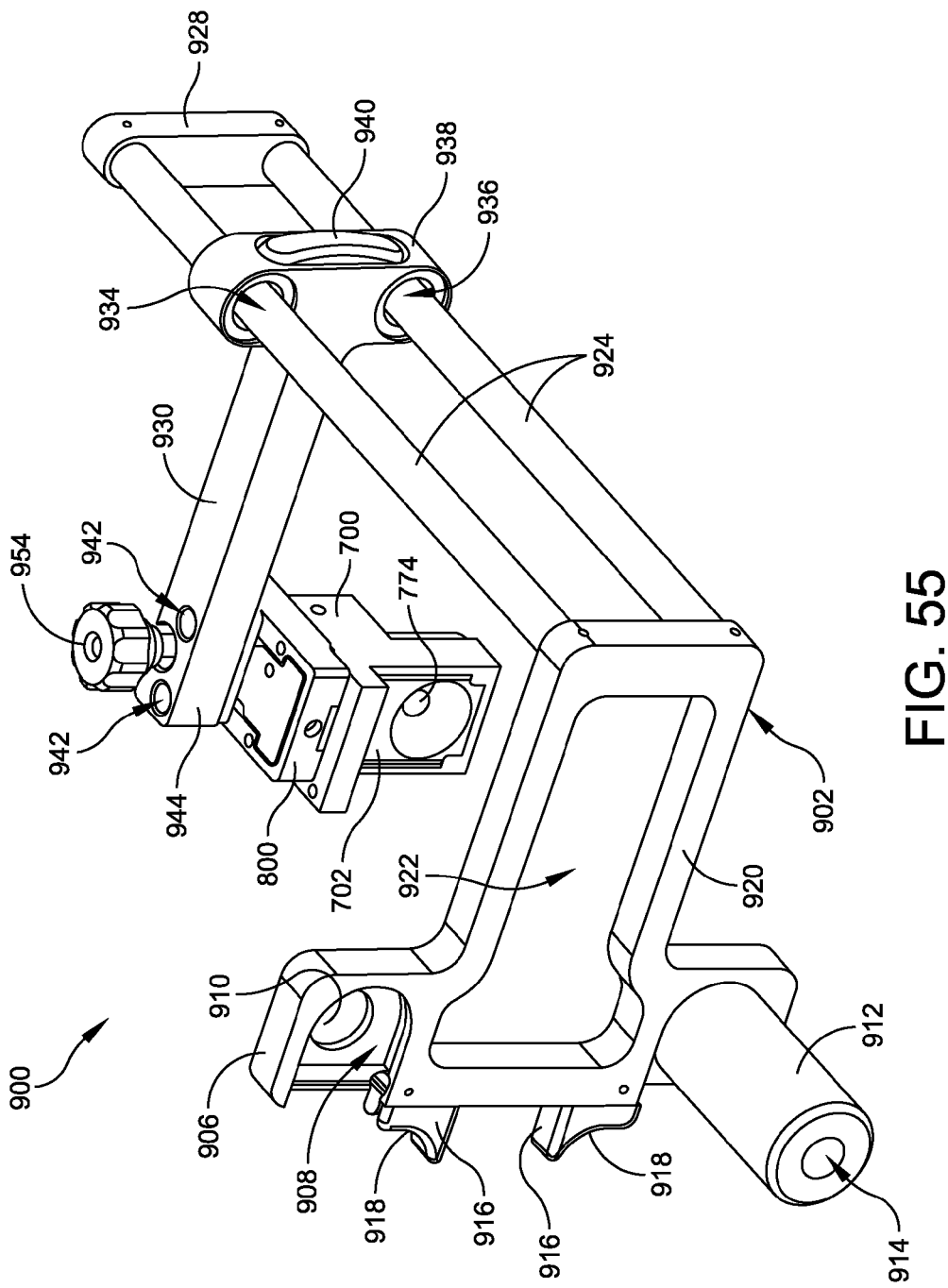
FIG. 55 is a perspective view of a foot holder assembly for use with the assembly illustrated in FIG. 51.

As shown in FIG. 55, foot holder assembly 900 includes a base plate 902 that extends from a first end 904 to a second end 906. First and second ends 904, 906 each define a pocket 908 and a hole 910. Pocket 908 is sized and configured to receive a drill bushing 912 having a cylindrical body defining hole 914 that aligns with through hole 910. Accordingly, both first end 904 and second end 906 may support an ankle or forefoot of a patient. Each pocket 908 includes a spring loaded detent 916 communicatively coupled to it that include a finger receiving surface 918 and is configured to slide relative to base plate 902 and secure drill bushing 912 within pocket 908. In some embodiments, drill bushing may be threaded and configured to be coupled to base plate 902 with complementary threads disposed on an inner surface of holes 910.

Base plate 902 also includes a medial/lateral extension 920 that extends in a substantially perpendicular direction from an approximate mid-point between first end 904 and second end 906. Base plate 902 may also define a viewing opening 922 such that a surgeon may be able to view the bottom of a patient's foot when the foot is secured to foot holder assembly 900.

Figure 56:
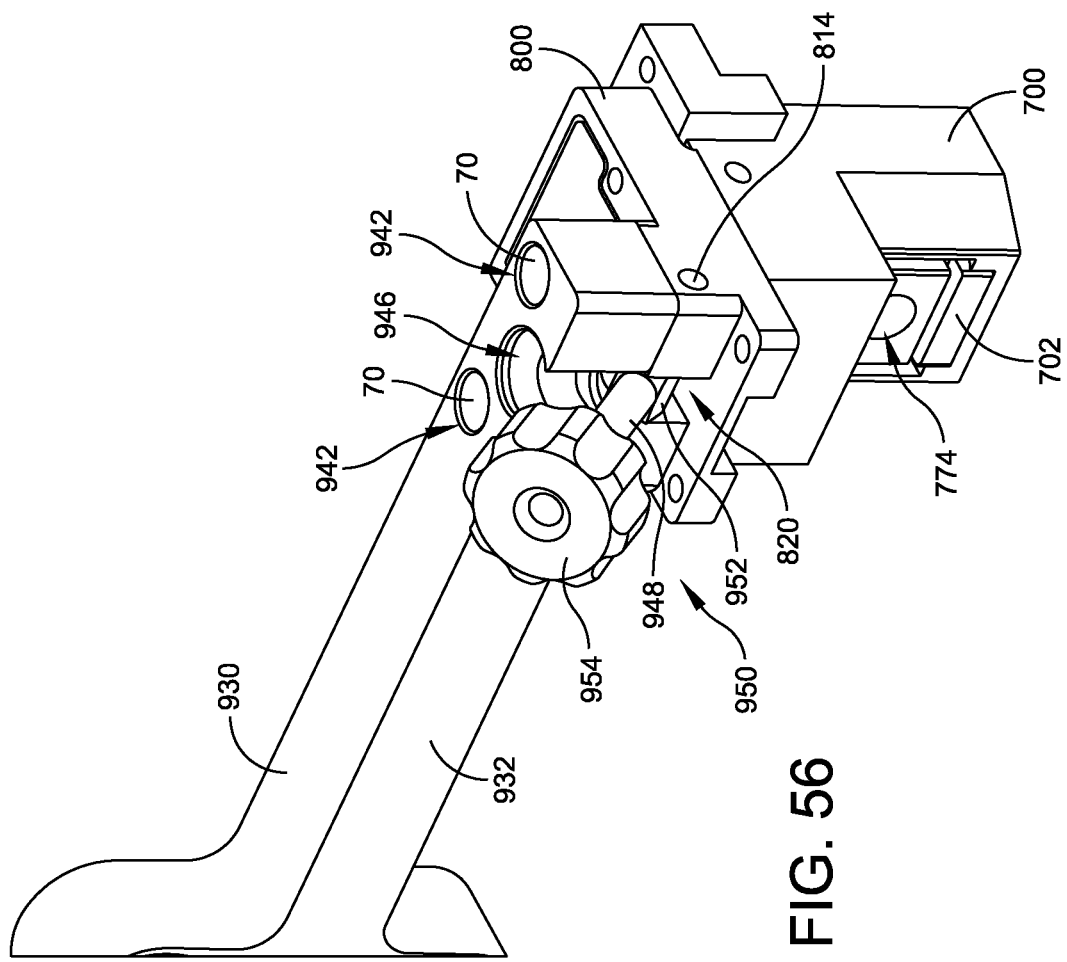
FIG. 56 is a perspective view of a pivoting arrangement used to secure the assembly illustrated in FIG. 51 to the foot holder assembly.
Figure 57:
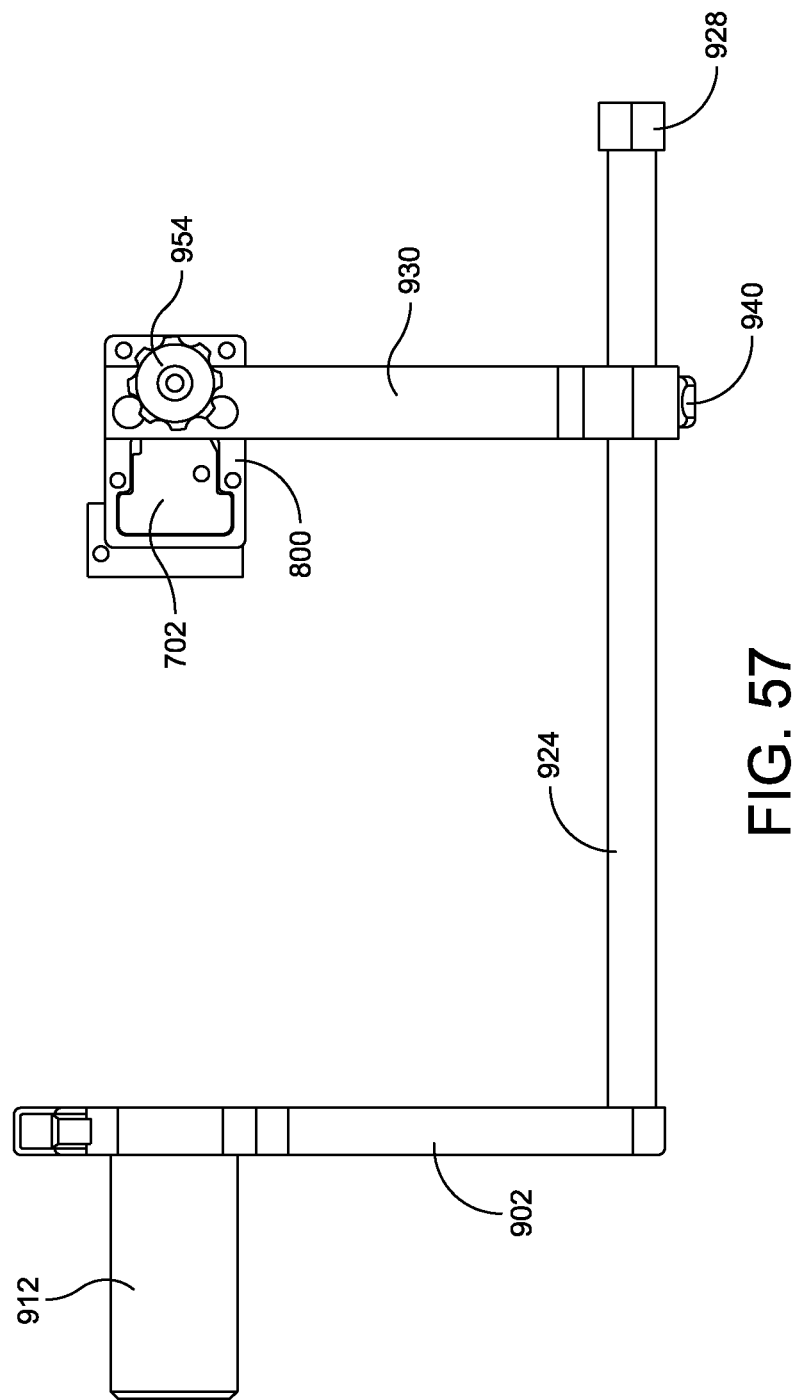
FIG. 57 is a top side plan view of the foot holder assembly illustrated in FIG. 55.
Figure 58:
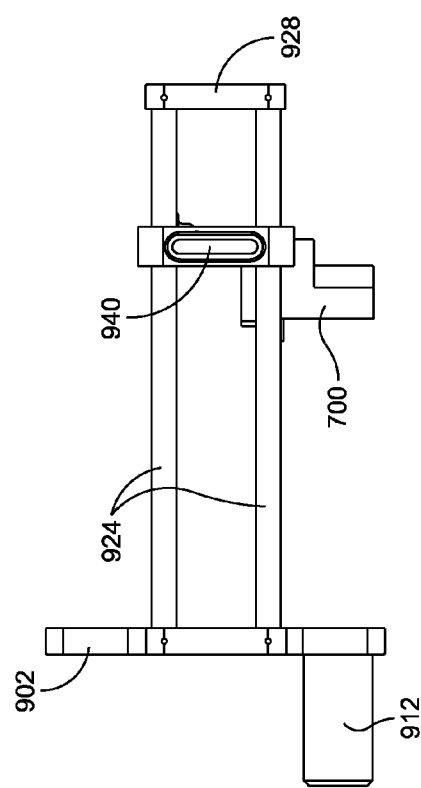
FIG. 58 is a side view of the foot holder assembly illustrated in FIG. 55.
Figure 59:
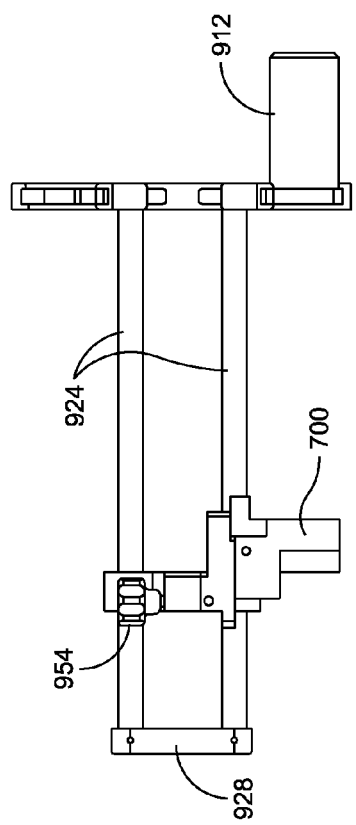
FIG. 59 is an opposite side view of the foot holder assembly illustrated in FIG. 55.
Figure 61:
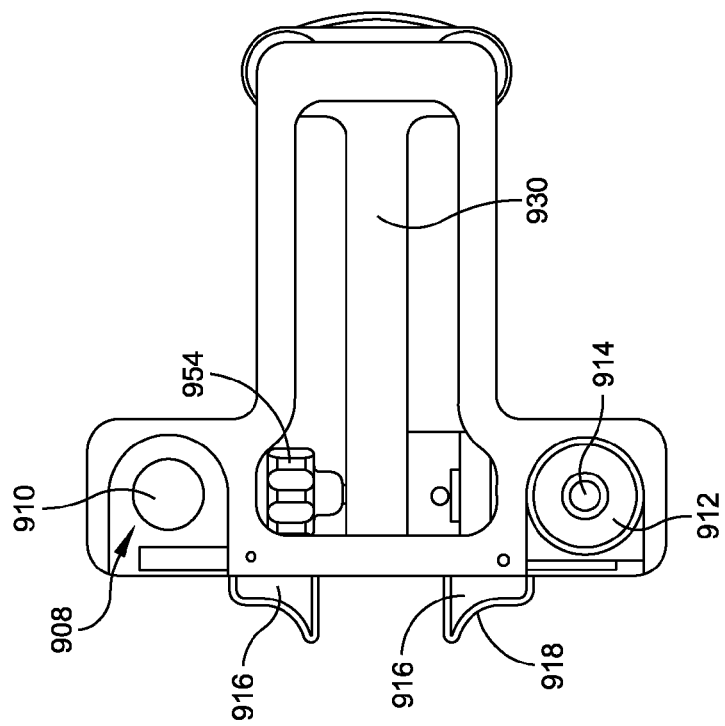
FIG. 61 is a front end view of the foot holder assembly illustrated in FIG. 55.

One or more rods 924 extend from base plate 902 in a substantially perpendicular direction with respect to an upper foot holding surface 926 (FIG. 56). Rods 924 may be secured to base plate 902 using screws or through other securing means as will be understood by one skilled in the art. A cap 928 is secured to an upper end of rods 924 and be secured to rods 924 using screws or other fixation means.

A mounting member 930 has an elongate body 932 that defines a pair of holes 934, 936 at one end 938 that slidably receive rods 924 such that mounting member 930 may be slid along rods 924 in order to position tibial drill guide mount 700 with respect to base plate 902. A spring loaded button 940 is disposed at first end 938 of mounting member 930 and is coupled to a locking mechanism (not shown) disposed within mounting member 930 for locking mounting member 930 at a position along rods 924.

Figure 60:
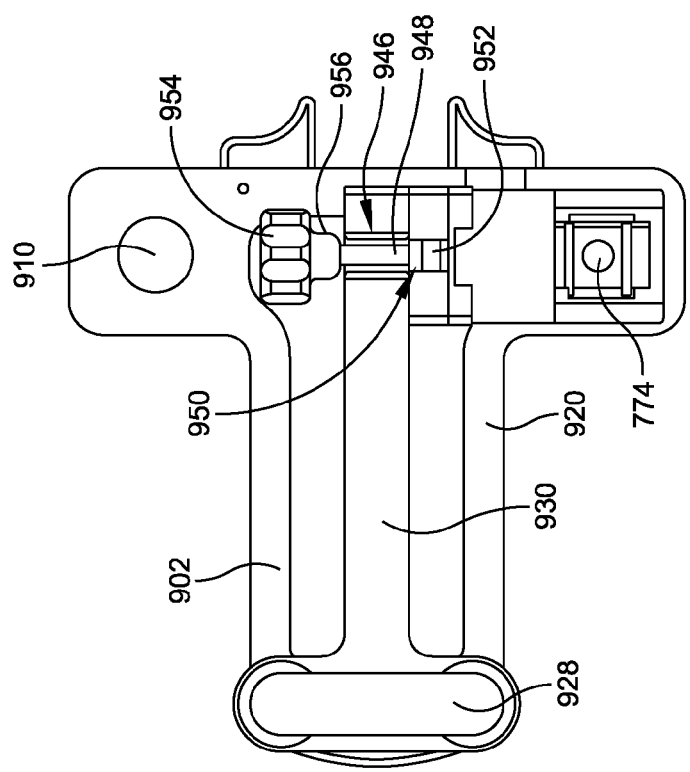
FIG. 60 is a rear end view of the foot holder assembly illustrated in FIG. 55.
Figure 62:
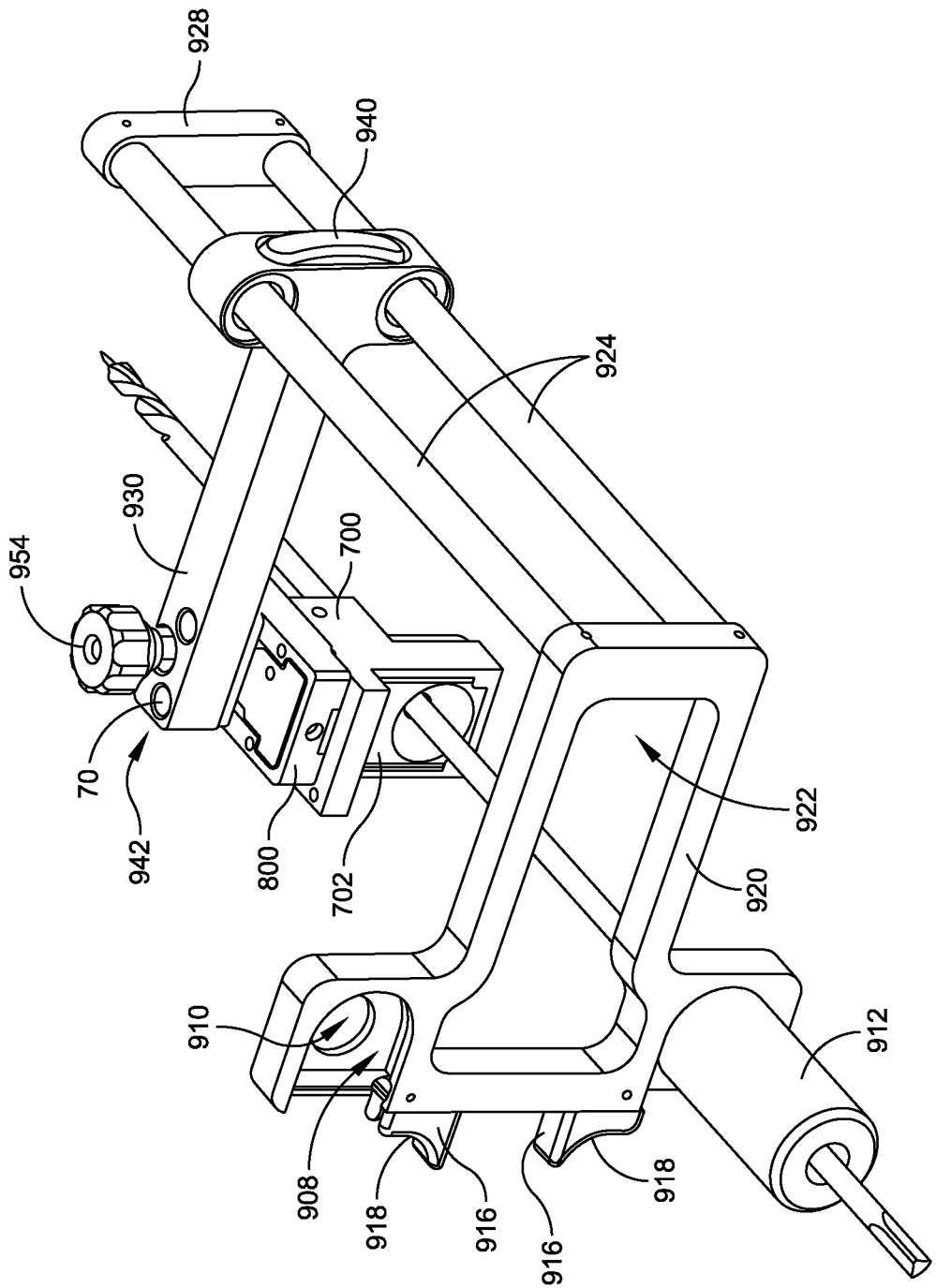
FIG. 62 is a perspective view of a drill being extended through the foot holder assembly and tibial drill guide.

One or more holes 942 are defined at the second end 944 of mounting member 930 and correspond to holes 716 of drill guide mount 700 for coupling drill guide mount 700 to foot holder assembly 900. Second end 942 also defines a slot 946, as best seen in FIGS. 56 and 60, that is sized and configured to receive an internally threaded rod 948 of a pivoting arrangement 950, which includes a lower portion 952 that is received within slot 820 of mounting plate 800 and is cross-pinned through hole 814. The cross-pinning of pivoting arrangement 950 may pivot about an axis defined by hole 814 and is configured to receive an support tightening knob 954. Bottom surface 956 (FIG. 60) of knob 954 has an outer dimension that is greater than slot 946 and is configured to engage mounting member 930 in order to secure the assemblage of mounting plate 800 and tibial drill guide mount 700, which may include tibial drill cartridge 702.

In operation, tibial drill guide mount 700 is inserted into resected joint space 22. Mounting plate 800 is connected to tibial drill guide mount 700 using dowel pins 70 as best seen in FIGS. 49 and 50. With pivoting arrangement 950 cross-pinned to mounting plate 800, the assemblage of mounting plate 800 and pivoting arrangement 948 is coupled to tibial drill guide mount with dowel pins 70, which may be press fit into holes 822 of mounting plate 800 and holes 716 of tibial drill guide mount 700 as will be understood by one skilled in the art. Tibial drill guide mount 700 and mounting plate may be secured within resected joint space 22 by inserting k-wires (not shown) into holes 736, 790 defined by tibial drill guide mount 700 and holes 830-1, 830-2 (corresponding to holes 736-1, 736-2) and 832-1, 832-2 defined by mounting plate 800.

With mounting plate 800 coupled to tibial drill guide mount 700 that is disposed within resected joint space 22, pivoting arrangement 948 is rotated such that it extends in a direction approximately parallel to a longitudinal axis defined by a patient's leg and the cartridge-style tibial drill guide 702 is inserted into aperture 804 of mounting plate 800 and recess 718 of tibial drill guide mount 700. Tibial drill guide cartridge 702 is inserted until leading end 786 of tibial drill cartridge 702 abuts rear wall 788 of tibial drill guide mount 700 at which point the ball detent disposed within hole 772 engages hole 828 defined by mounting plate 800 and the front side 768 of tibial drill guide cartridge 702 is flush with front side 806 of mounting plate 800.

Holes 940 of mounting member 930 are aligned with, and received over, dowel pins 70 that extend from front side 806 of mounting plate to couple mounting member 930 of foot holder assembly 900 to the assemblage of mounting plate 800, tibial drill guide mount 700, and tibial drill guide cartridge 702. With mounting member 903 coupled to dowel pins 70 and mounting plate 800, pivoting arrangement 948 is rotated with respect to mounting plate 800 such that rod 946 of pivoting arrangement 948 is received within slot 944 of mounting member 930. Knob 952 is then rotated about its axis (clockwise or counterclockwise) such that the bottom surface 954 of knob 952 contacts mounting member 930 to maintain engagement between mounting member 930 and the assemblage of tibial drill guide mount 700 and mounting plate 800.

Drill bushing 912 is coupled to hole 910 that is aligned with the heel of a patient's foot. As described above, drill bushing 912 may be slid into pocket 908 defined by bottom plate 902 until spring loaded detents 916 releasably lock drill bushing 912 in place. In some embodiments, drill bushing 912 may be screwed into base plate 902 by way of corresponding threads disposed on an outer surface of drill bushing 912 that engage threads defined by an inner surface of pocket 908 and/or hole 910. With drill bushing 912 in place and the patient's leg secured to foot holder assembly 900, various minimally invasive surgical techniques may be used to introduce a bottom foot cannula into the calcaneus 20, talus 14, and tibia 16 as described above.

Once access to the patent's calcaneus has been achieved, a bottom foot cannula 64 is inserted through the patient's calcaneus 20. A reamer 66 is operated through the cannula 64 to drill approximately another through the talus 14 and up into the tibia 16 to establish an intramedullary guide path through the calcaneus 20 and talus 14 leading into the tibia 16. As reamer 66 exits talus 14, the conically shaped internal surface 748 guides the tip 68 into hole 788. An axis defined by hole 788 is substantially axially aligned with a mechanical axis of tibia 16 such that as reamer 66 is extended through hole 788, it bores an intramedullary canal within tibia 16.

The disclosed system and method advantageously utilize custom manufactured surgical instruments, guides, and/or fixtures that are based upon a patient's anatomy to reduce the use of fluoroscopy during a surgical procedure. In some instances, the use of fluoroscopy during a surgical procedure may be eliminated altogether. The custom instruments, guides, and/or fixtures are created by imaging a patient's anatomy with a computer tomography scanner ("CT"), a magnetic resonance imaging machine ("MRI"), or like medical imaging technology prior to surgery and utilizing these images to create patient-specific instruments, guides, and/or fixtures.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system for establishing an intramedullary path, comprising:
 a body sized and configured to be received within a resected bone space and defining a first aperture that extends through the body, the first aperture sized and configured to receive a surgical tool therethrough;
 a first bone engaging structure extending from the body in a first direction, the first bone engaging structure including a first surface that is complementary to a surface topography of a tibia; and
 a drill guide sized and configured to be received within the first aperture defined by the body, the drill guide defining a second aperture sized and configured to receive the surgical tool therethrough,
 wherein when the first surface of the bone engaging structure engages the surface topography of the tibia to which the first surface is complementary, an axis defined by the first aperture is substantially collinear with an axis of the tibia, and
 wherein the first aperture includes a reduced diameter portion, and an outer surface of the drill guide includes a first portion having a smaller cross-sectional area than a second portion and being sized and configured to be received within the reduced diameter portion of the first aperture.

2. The system of claim 1, wherein a second bone engaging structure extends from the body in a direction that is substantially opposite the first direction, the second bone engaging structure including a second surface that is complementary to a surface topography of a second bone that is different from the tibia.

3. The system of claim 2, wherein the second bone is a talus.

4. The system of claim 1, wherein an outer surface of the drill guide includes a flat surface that is complementary to a non-rotation feature disposed within the first aperture.

5. The system of claim 1, wherein the second aperture tapers along at least part of its length.

6. The system of claim 1, wherein the body defines at least one hole for coupling the body to a coupling bar, the coupling bar configured to engage a pair of alignment rods extending from a foot holder assembly.

7. A system for establishing an intramedullary path, comprising:
 a drill guide mount including a body sized and configured to be received within a resected bone space, the body defining a first aperture that extends through the body, a first bone engaging structure extending from the body in a first direction and including a first surface that is complementary to a surface topography of a tibia; and
 a drill guide sized and configured to be received within the first aperture defined by the body of the drill guide mount, the drill guide defining a second aperture sized and configured to receive the surgical tool therethrough,
 wherein when the first surface of the bone engaging structure engages the surface topography of the first bone to which the first surface is complementary, an axis defined by the first aperture is substantially collinear with an axis of the tibia,
 wherein the first aperture includes a reduced diameter portion, and an outer surface of the drill guide includes a first portion having a smaller cross-sectional area than a second portion and being sized and configured to be received within the reduced diameter portion of the first aperture.

8. The system of claim 7, wherein a second bone engaging structure extends from the body of the drill guide mount in a direction that is substantially opposite the first direction, the second bone engaging structure including a second surface that is complementary to a surface topography of a second bone that is different from the tibia.

9. The system of claim 8, wherein the first and second bone engaging structures each include at least one hole sized and configured to receive a k-wire therethrough.

10. The system of claim 7, wherein an outer surface of the drill guide includes a flat surface that is complementary to a non-rotation feature disposed within the first aperture.

11. The system of claim 7, wherein the second aperture tapers along at least part of its length.

12. The system of claim 7, further comprising a coupling bar sized and configured to engage a pair of alignment rods extending from a foot holder assembly, the coupling bar configured to be coupled to the body of the drill guide mount for maintaining a position of the drill guide mount relative to the foot holder assembly.

13. A method comprising: inserting a first portion of a drill guide into a reduced diameter portion of an aperture defined by a drill guide mount, the first portion of the drill guide having a smaller cross-sectional area than a second portion of the drill guide, the drill guide mount including a first bone engaging structure extending from a body of the drill guide mount in a first direction and having a first surface that is complementary to a surface topography of a tibia; inserting the drill guide mount and the drill guide disposed within the first aperture of the drill guide mount into a resected bone space such that the first surface of the bone engaging structure correspondingly engages the tibia; and extending a surgical tool through a second aperture defined by the drill guide to establish an intramedullary channel within the first bone that is substantially collinear with an axis of the tibia.

14. The method of claim 13, wherein the drill guide mount includes a second bone engaging structure that extends from the body of the drill guide mount in a direction that is substantially opposite the first direction, the second bone engaging structure including a second surface that is complementary to a surface topography of a second bone that is different from the tibia.

15. The method of claim 14, wherein when the first surface of the bone engaging structure correspondingly engages the tibia, the second surface correspondingly engages the second bone.

16. The method of claim 13, further comprising:
inserting a first k-wire through a first hole defined by the first bone engaging structure and into the tibia; and
inserting a second k-wire through a second hole defined by the second bone engaging structure and into the second bone.

17. The method of claim 13, further comprising:
coupling the drill guide mount to a coupling bar; and
attaching the coupling bar to a pair of alignment rods extending from a surgical fixation assembly.

18. The method of claim 17, wherein the surgical fixation assembly is a foot holder assembly, the first bone is the tibia, and the second bone is the talus.

* * * * *